United States Patent
Corvey et al.

(10) Patent No.: US 10,065,998 B2
(45) Date of Patent: Sep. 4, 2018

(54) PROTEINS SPECIFIC FOR PYOVERDINE AND PYOCHELIN

(71) Applicant: SANOFI, Paris (FR)

(72) Inventors: Carsten Corvey, Frankfurt am Main (DE); Heike Stump, Frankfurt am Main (DE); Jochen Kruip, Frankfurt am Main (DE); Bernhard Calandra, Chilly-Mazarin (FR); Astrid Rey, Toulouse (FR); Nathalie Karst, Vitry sur Seine (FR); Michael Mourez, Toulouse (FR); Laurent Fraisse, Toulouse (FR); Christine Rothe, Freising (DE); Andrea Allersdorfer, Freising (DE); Alexander Wiedenmann, Herbrechtingen (DE); Marlon Hinner, Freising (DE); Bradley Lunde, Lebanon, NH (US); Kristian Jensen, Landshut (DE); Martin Hülsmeyer, Römerberg (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/726,577

(22) Filed: Oct. 6, 2017

(65) Prior Publication Data

US 2018/0030101 A1 Feb. 1, 2018

Related U.S. Application Data

(60) Continuation of application No. 15/602,783, filed on May 23, 2017, now Pat. No. 9,884,898, which is a division of application No. PCT/EP2016/053226, filed on Feb. 16, 2016.

(30) Foreign Application Priority Data

Feb. 18, 2015 (EP) .................................... 15305242

(51) Int. Cl.
*C07K 14/47* (2006.01)
*A61K 38/01* (2006.01)
*A61K 38/00* (2006.01)

(52) U.S. Cl.
CPC .......... *C07K 14/4703* (2013.01); *A61K 38/00* (2013.01); *A61K 38/005* (2013.01); *A61K 38/012* (2013.01); *C07K 14/47* (2013.01); *H05K 999/99* (2013.01)

(58) Field of Classification Search
None
See application file for complete search history.

(56) References Cited

U.S. PATENT DOCUMENTS 5,728,553 A 3/1998 Goodey et al.
6,177,074 B1 1/2001 Glue et al.
6,403,564 B1 6/2002 Ganguly et al.
6,500,930 B2 12/2002 Adamson
6,620,413 B1 9/2003 DeSauvage et al.
6,696,245 B2 2/2004 Winter et al.
9,884,898 B2 * 2/2018 Corvey .............. C07K 14/4703
2003/0069395 A1 4/2003 Sato et al.
2017/0029477 A1 2/2017 Corvey et al.
2017/0267734 A1 * 9/2017 Corvey .............. C07K 14/4703
2018/0030101 A1 * 2/2018 Corvey .................. A61K 38/00
2018/0037618 A1 * 2/2018 Corvey .................. A61K 38/00

FOREIGN PATENT DOCUMENTS

| EP | 0 330 451 A2 | 8/1989 |
| EP | 0 361 991 A1 | 4/1990 |
| WO | 1999/064016 A1 | 12/1999 |
| WO | 2004/060918 A1 | 7/2004 |
| WO | 2006/056464 A2 | 6/2006 |
| WO | 2007/038619 A2 | 4/2007 |
| WO | 2009/156456 A1 | 12/2009 |
| WO | 2011/149962 A1 | 12/2011 |
| WO | 2014/076321 A1 | 5/2014 |

OTHER PUBLICATIONS

Banin et al. (2005) "Iron and Pseudomonas aeruginosa biofilm formation," Proc. Natl. Acad. Sci. USA. 102 (31):11076-11081.
Brandel et al. (2011) "Pyochelin, a siderophore of Pseudomonas aeruginosa: Physicochemical characterization of the iron(III), copper(II) and zinc(II) complexes," Dalton Trans. 41:2820-2834.
Breustedt et al. (2005) "The 1.8-Å crystal structure of human tear lipocalin reveals an extended branched cavity with capacity for multiple ligands," J. Biol. Chem. 280:484-493.
Briskot et al. (1989) "Bacterial Constituents, XXXVII. Pyoverdin-Type Siderophores from Pseudomonas aeruginosa," Liebigs Ann. Chem. 1989(4):375-384.
Bruckdorfer et al. (2004) "From production of peptides in milligram amounts for research to multi-tons quantities for drugs of the future," Curr. Pharm. Biotechnol. 5:29-43.
Cornelis et al. (1989) "Evidence for different pyoverdine-mediated iron uptake systems among Pseudomonas aeruginosa strains," Infect. Immun. 57:3491-3497.
Costerton et al. (1999) "Bacterial biofilms: a common cause of persistent infections," Science. 284(5418):1318-1322.

(Continued)

*Primary Examiner* — Padmavathi Baskar
(74) *Attorney, Agent, or Firm* — Lathrope Gage LLP; James H. Velema, Esq.

(57) ABSTRACT

The present disclosure provides hNGAL muteins that bind a pyoverdine family member or pyochelin and can be used in various application including pharmaceutical applications, for example, to inhibit or reduce growth of *P. aeruginosa*. The present disclosure also concerns methods of making one or more pyoverdine- or pyochelin-binding muteins described herein as well as compositions comprising one or more of such muteins. The present disclosure further relates to nucleic acid molecules encoding such muteins and to methods for generation of such muteins and nucleic acid molecules. In addition, the application discloses therapeutic and/or diagnostic uses of these muteins as well as compositions comprising one or more of such muteins.

18 Claims, 9 Drawing Sheets

Figure 1A:
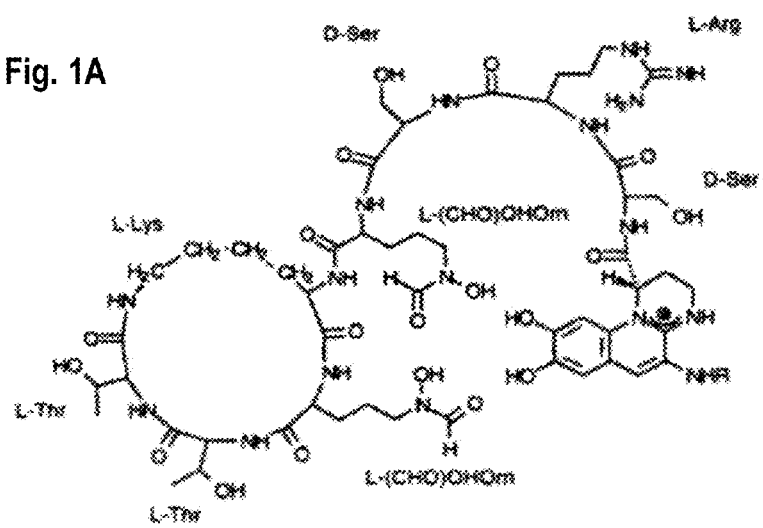

Specification includes a Sequence Listing.

(56) References Cited

OTHER PUBLICATIONS

Dennis et al. (2002) "Albumin binding as a general strategy for improving the pharmacokinetics of proteins," J. Biol. Chem. 277:35035-35043.
Flower (1996) "The lipocalin protein family: structure and function," Biochem. J. 318 (Pt 1):1-14.
Flower et al. (2000) "The lipocalin protein family: structural and sequence overview," Biochim. Biophys. Acta. 1482 (1-2):9-24.
Fluckinger et al. (2004) "Human tear lipocalin exhibits antimicrobial activity by scavenging microbial siderophores," Antimicrob. Agents Chemother. 48(9):3367-3372.
Fuertges et al. (1990) "The Clinical Efficacy of Poly(Ethylene Glycol)Modified Proteins," J. Control. Release 11:139-148.
Gipp et al.(1991) "Zwei Pyoverdine aus Pseudomonas aeruginosa R.," Z. Naturforsch. C. 46c:534-541.—Chemical Structures Only.
Heinrichs et al. (1996) "PchR, a regulator of ferripyochelin receptor gene (fptA) expression in Pseudomonas aeruginosa, functions both as an activator and as a repressor," J. Bacteriol. 178(9):2586-2592.
Holmes et al. (2005) "Siderocalin (Lcn 2) also binds carboxymycobactins, potentially defending against mycobacterial infections through iron sequestration," Structure. 13(1):29-41.
Konig et al. (1998) "Use of an albumin-binding domain for the selective immobilisation of recombinant capture antibody fragments on ELISA plates," J. Immunol. Methods. 218:73-83.
Lamont et al. (2000) "Siderophore-mediated signaling regulates virulence factor production in Pseudomonas aeruginosa," Proc. Natl. Acad. Sci. USA. 99(10):7072-7077.
Lowman (1997) "Bacteriophage display and discovery of peptide leads for drug development," Annu. Rev. Biophys. Biomol. Struct. 26:401-424.
Meyer et al. (1996) "Pyoverdin is essential for virulence of Pseudomonas aeruginosa," Infection and Immunity. 64:518-523.
Meyer et al. (1997) "Use of siderophores to type pseudomonads: the three Pseudomonas aeruginosa pyoverdine systems," Microbiology. 143(Pt 1):35-43.
Osborn et al. (2002) "Pharmacokinetic and pharmacodynamic studies of a human serum albumin-interferon-alpha fusion protein in cynomolgus monkeys," J. Pharmacal. Exp. Ther. 303:540-548.
Peek et al. (2012) "Pyoverdine, the Major Siderophore in Pseudomonas aeruginosa, Evades NGAL Recognition," Interdiscip. Perspect. Infect. Dis. 2012:843509. pp. 1-10.
Rodi et al. (1999) "Phage-display technology—finding a needle in a vast molecular haystack," Curr. Opin. Biotechnol. 10(1):87-93.
Schmidt et al. (1996) "Molecular interaction between the Strep-tag affinity peptide and its cognate target, streptavidin," J. Mol. Biol. 255:753-766.
Singh et al. (2000) "Quorum-sensing signals indicate that cystic fibrosis lungs are infected with bacterial biofilms," Nature. 407:762-764.
Takase et al. (2000) "Impact of Siderophore Production on Pseudomonas aeruginosa Infections in Immunosuppressed Mice," Infection and Immunity.68(4):1834-1839.
Tappe et al. (1993) "Structure elucidation of a Pyoverdin Produced by Pseudomonas aeruginosa ATCC 27 853," Journal fur Praktische Chemie. 335(1):83-87.
Uniprot Database [online] "UniProtKB—P80188 (NGAL_Human)," Accessible on the Internet at URL: http://www.uniprot.org/uniprot/P80188. [Last Accessed Sep. 20, 2016].
Vajo et al. (2000) "Genetically engineered insulin analogs: diabetes in the new millenium," Pharmacol. Rev. 52(1):1-9.
Venturi et al. (2002) "High level production of functional antibody Fab fragments in an oxidizing bacterial cytoplasm," J. Mol. Biol. 315:1-8.
Visca et al. (1992) "Isolation and characterization of Pseudomonas aeruginosa mutants blocked in the synthesis of pyoverdin," J. Bacteriol. 174(17):5727-5731.
Houghten et al. (1986) "Relative Importance of Position and Individual Amino Acid Residues in Peptide Antigen-Antibody Interactions: Implications in the Mechanism of Antigenic Drift and Antigenic Shift," Vaccines. 21-25.
International Search Report with Written Opinion corresponding to International Patent Application No. PCT/EP2016/053226, dated Mar. 16, 2016.
International Search Report with Written Opinion corresponding to International Patent Application No. PCT/EP2016/065899, dated Oct. 4, 2016.

\* cited by examiner

PVD group I
*P. aeruginosa* ATCC 15692 (PAO1)

PVD group II
*P. aeruginosa* ATCC 27853

PVD group III
P. aeruginosa R and Pa6

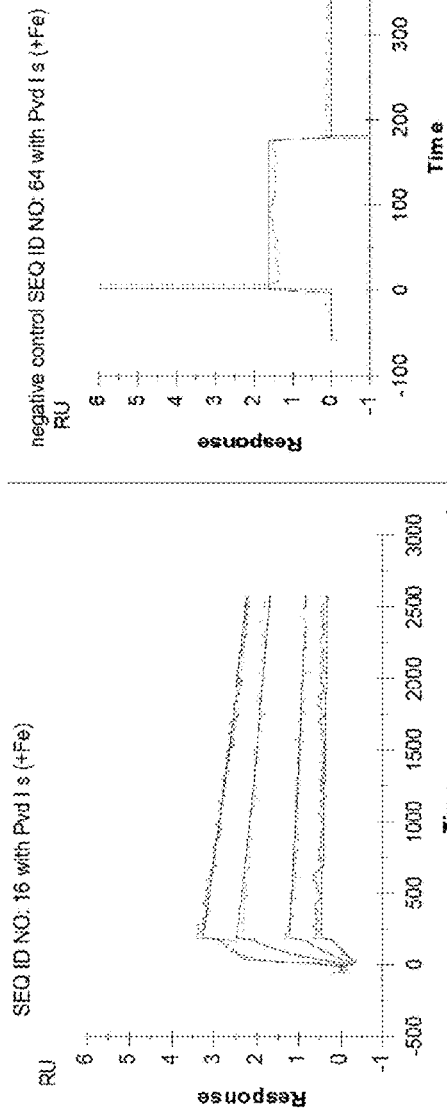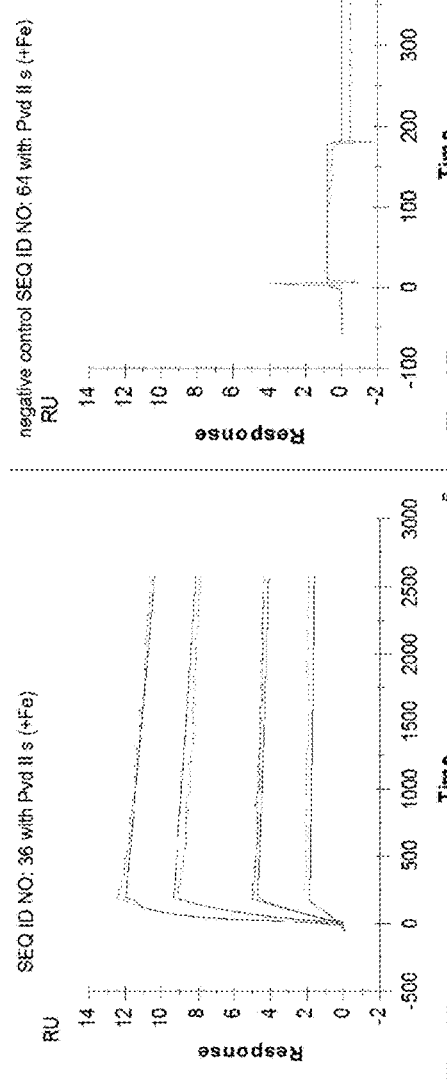

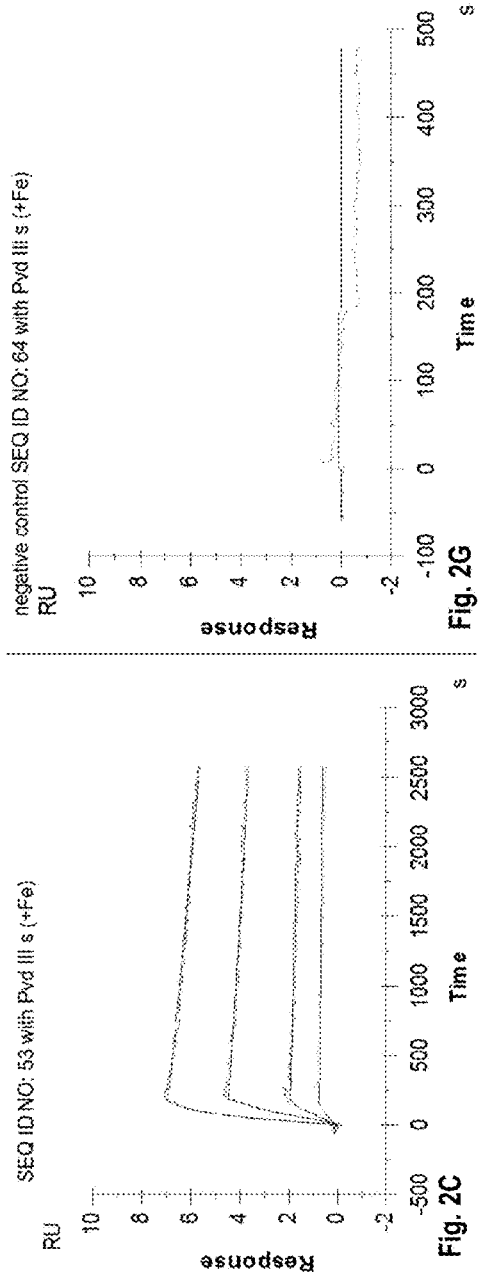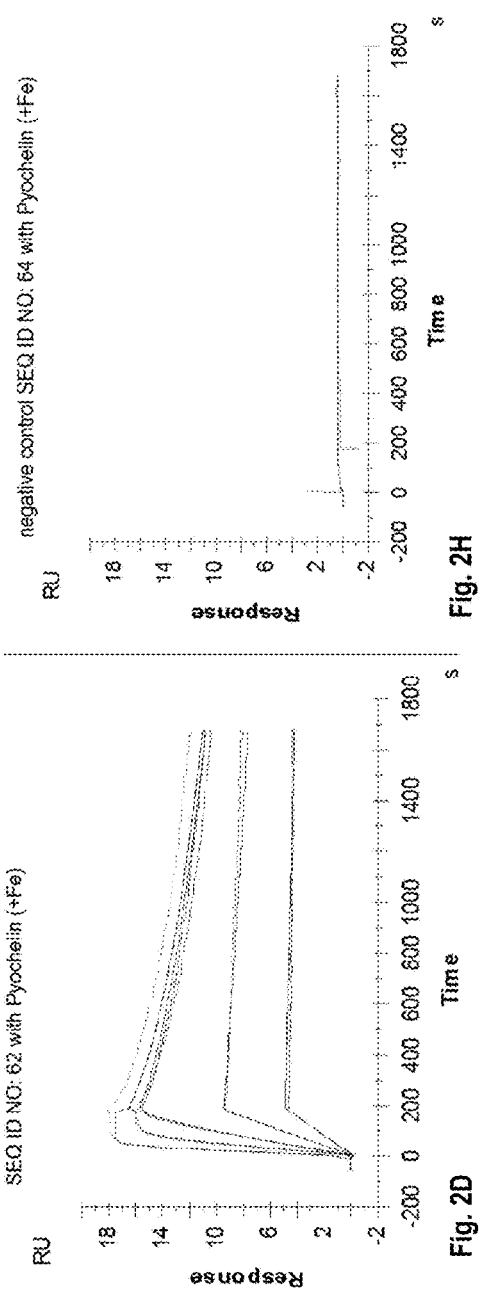

Fig. 6

The protein amino acid sequence expressed (SEQ ID NO: 129)

MKHHHHHHHDYDIPTTENLYFQGQDSTSDLIPAPPLSKVPLQQNFQDNQFHG
KWYVVGVAGNTILREDKDPGKMNATIYELKEDKSYNVTDVRFIRKKCHYYIDT
FVPGSQPGEFTLGNIKSYPGTTSQLVRVVSTNYNQHAMVFFKIVRQNREIFW
ITLYGRTKELTSELKENFIRFSKSLGLPENHIVFPVPIDQCIDG

Fig. 7

SEQ ID NO: 31 – Pvd-Fe complex structure, two SEQ ID NO: 31 molecules i.e. chain A and chain B from asymmetric unit are overlaid.

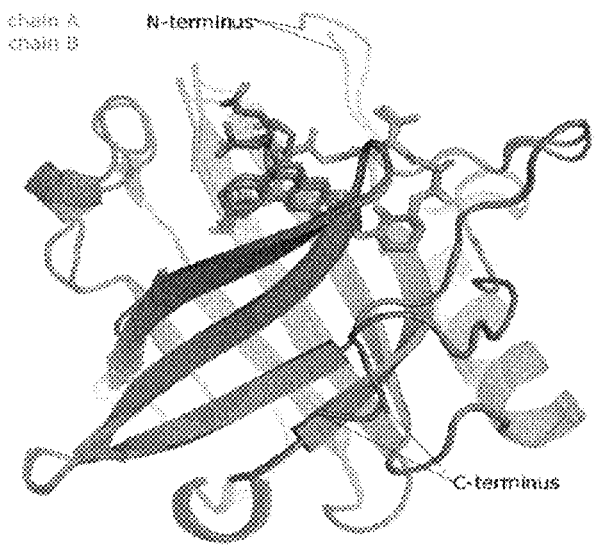

SEQ ID NO: 31 and Pvd-Fe interactions. Two molecules from asymmetric unit are overlaid.
Side chains interacting with Pvd-Fe are depicted Pvd composition, oxygen atoms involved in iron binding are boxed

PROTEINS SPECIFIC FOR PYOVERDINE AND PYOCHELIN

CROSS-REFERENCE TO RELATED APPLICATIONS

This application is a division of U.S. patent application Ser. No. 15/602,783, filed May 23, 2017, which is a continuation of International Patent Application No. PCT/EP2016/053226, filed Feb. 16, 2016, which claims priority to European Patent Application No. 15305242.8, filed Feb. 18, 2015, the entire disclosures of which are hereby incorporated herein by reference.

I. BACKGROUND

*Pseudomonas aeruginosa* (*P. aeruginosa*) is an opportunistic pathogen that causes acute infections, primarily in association with tissue injuries. *P. aeruginosa* forms biofilms on indwelling devices and on the pulmonary tissues of patients with the genetic disorder, cystic fibrosis. Biofilm infections are difficult to treat with conventional antibiotic therapies. However, research has demonstrated that iron is essential for proper biofilm formation by *P. aeruginosa*, and therefore iron-uptake systems are potential targets for anti-*Pseudomonas* therapies.

*P. aeruginosa* is able to scavenge iron from the host environment by using the secreted iron-binding siderophores, pyochelin and pyoverdine. Pyoverdine (Pvd) is a peptide-linked hydroxamate- and catecholate-type ligand, and pyochelin (Pch) a derivatized conjugate of salicylate and two molecules of cysteine and having phenol, carboxylate, and amine ligand functionalities. Both Pvd and Pch have demonstrated roles in *P. aeruginosa* virulence with some indication of synergism. Double-deficient mutants unable to make either siderophore are much more attenuated in virulence than either single-deficient mutant unable to make just one of the two siderophores (Takase et al., Infection and immunity, April 2000, p. 1834-1839). Furthermore, pyoverdine acts as a signalling molecule to control production of several virulence factors as well as pyoverdine itself; while it has been proposed that pyochelin may be part of a system for obtaining divalent metals such as ferrous iron and zinc for *P. aeruginosa*'s pathogenicity, in addition to ferric iron (Visca et al., 1992).

Three structurally different pyoverdine types or groups have been identified from several *P. aeruginosa* strains: from *P. aeruginosa* ATCC 15692 (Briskot et al., 1989, Liebigs Ann Chem, p. 375-384), from *P. aeruginosa* ATCC 27853 (Tappe et al., 1993, J. Prakt-Chem., 335, p. 83-87) and from a natural isolate, *P. aeruginosa* R (Gipp et al., 1991, Z. Naturforsch, 46c, p. 534-541). Moreover, comparative biological investigations on 88 clinical isolates and the two collection strains mentioned above revealed three different strain-specific pyoverdine-mediated iron uptake systems (Cornells et al., 1989, Infect Immun., 57, p. 3491-3497; Meyer et al., 1997, Microbiology, 143, p. 35-43) according to the reference strains: *P. aeruginosa* ATCC 15692 (Type I Pvd or Pvd I), *P. aeruginosa* ATCC 27853 (Type II Pvd or Pvd II) and the clinical isolates *P. aeruginosa* R and pa6 (Type III Pvd or Pvd III).

Each pyoverdine type has three members (subtypes) differing in the side chain which is succinyl, succinamid or α-ketoglutaryl, namely, Pvd type I succinyl, Pvd type I succinamid, Pvd type I α-ketoglutaryl, Pvd type II succinyl, Pvd type II succinamid, Pvd type II α-ketoglutaryl, Pvd type III succinyl, Pvd type III succinamid and Pvd type III α-ketoglutaryl.

Each *P. aeruginosa* strain expresses one Pvd type i.e. *P. aeruginosa* ATCC 15692 expresses Type I Pvd, *P. aeruginosa* ATCC 27853 expresses Type II Pvd and *P. aeruginosa* R and pa6 expresses Type III Pvd, whereby each Pvd type includes all three members of the respective type, and each said strain also expresses pyochelin.

In this regard, we identified the pyoverdins and pyochelin as targets which are crucial for *P. aeruginosa*'s pathogenicity and developed specific inhibitors for such targets, as disclosed here, i.e. for each type of Pvd including for every type the three members (subtypes) differing in the side chain (Pvd I s, Pvd I sa, Pvd I αKG, Pvd II s, Pvd II sa, Pvd II αKG, Pvd III s, Pvd III sa, Pvd III αKG) as well as for Pch, and in every case to the free siderophore as well as to the siderophore with bound iron without creating the strong selective pressure imposed by conventional antibiotics. In addition, we selected inhibitors that distinguish free and iron-loaded pyochelin.

The present invention was made as a result of activities undertaken on behalf of Pieris AG, Sanofi-Aventis and Sanofi-Pasteur Inc., which are parties to an existing joint research agreement, and was made within the scope of the joint research agreement.

II. DEFINITIONS

The following list defines terms, phrases, and abbreviations used throughout the instant specification. All terms listed and defined herein are intended to encompass all grammatical forms.

As used herein, "pyoverdine" means a fluorescent siderophore that is produced by the gram negative bacterium *Pseudomonas aeruginosa* under iron-deficient growth conditions and has high affinity for iron. Pyoverdines are composed of three structural parts: a dihydroxyquinoline chromophore, a side chain and a variable peptidic chain. The peptide chain moiety is involved in receptor recognition and binding. Three different Pvds, differing in their peptide chain, have been identified (types I-III). The size and amino acid composition of pyoverdine types are unique to each species, as well as the pyoverdine recognition specificity. Three *P. aeruginosa* strains can be distinguished, each producing a different pyoverdine type (type I-III, FIG. 1) and a cognate FpvA receptor.

As used herein, "pyochelin" means a thiazoline derivatized conjugate of salicylate and two molecules of cysteine and having phenol, carboxylate, and amine ligand functionalities, produced by *P. aeruginosa* and solubilizing ferric iron. Pyochelin is a structurally unique siderophore possessing phenolate, but neither a hydroxamate nor a catecholate moiety (see FIG. 1.)

As used herein, "detectable affinity" means the ability to bind to a selected target with an affinity constant of generally at least about $10^{-5}$ M or below. Lower affinities are generally no longer measurable with common methods such as ELISA and therefore of secondary importance.

As used herein, "binding affinity" of a protein of the disclosure (e.g. a mutein of human lipocalin 2) or a fusion polypeptide thereof to a selected target (in the present case, pyoverdine or pyochelin), can be measured (and thereby KD values of a mutein-ligand complex be determined) by a multitude of methods known to those skilled in the art.

Such methods include, but are not limited to, fluorescence titration, direct ELISA, competition ELISA, calorimetric methods, such as isothermal titration calorimetry (ITC), and surface plasmon resonance (BIAcore). Such methods are well established in the art and examples thereof are also detailed below.

It is also noted that the complex formation between the respective binder and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, direct ELISA, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective binder and its target/ligand) may vary within a certain experimental range, depending on the method and experimental setup that is used for determining the affinity of a particular mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold. Said term also includes fragments of a mutein and variants as described herein. Muteins of the present disclosure, fragments or variants thereof preferably retain the function of binding to pyoverdine or pyochelin as described herein.

The term "fragment" as used herein in connection with the muteins of the disclosure relates to proteins or peptides derived from full-length mature human lipocalin 2 that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature human lipocalin 2 and are usually detectable in an immunoassay of the mature human lipocalin 2. In general, the term "fragment", as used herein with respect to the corresponding protein ligand of a mutein of the disclosure or of the combination according to the disclosure or of a fusion protein described herein, relates to N-terminally and/or C-terminally shortened protein or peptide ligands, which retain the capability of the full length ligand to be recognized and/or bound by a mutein according to the disclosure.

The term "mutagenesis" as used herein means that the experimental conditions are chosen such that the amino acid naturally occurring at a given sequence position of the mature human lipocalin 2 can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild type protein. Such an insertion or deletion may be introduced independently from each other in any of the peptide segments that can be subjected to mutagenesis in the disclosure.

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Sequence identity is measured by dividing the number of identical amino acid residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any mutein of the disclosure).

The percentage of sequence homology or sequence identity can, for example, be determined herein using the program BLASTP, version blastp 2.2.5 (Nov. 16, 2002; cf. Altschul, S. F. et al. (1997) Nucl. Acids Res. 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a mutein different from the wild-type human lipocalin 2 corresponds to a certain position in the amino acid sequence of the wild-type human lipocalin 2, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, the wild-type human lipocalin 2 can serve as "subject sequence" or "reference sequence", while the amino acid sequence of a mutein different from the wild-type human lipocalin 2 described herein serves as "query sequence". The terms "reference sequence" and "wild type sequence" are used interchangeably herein.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of sequence identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, omithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

By a "native sequence" human lipocalin 2 is meant human lipocalin 2 that has the same amino acid sequence as the corresponding polypeptide derived from nature. Thus, a native sequence human lipocalin 2 can have the amino acid sequence of the respective naturally-occurring human lipocalin 2. Such native sequence polypeptide can be isolated from nature or can be produced by recombinant or synthetic means. The term "native sequence" polypeptide specifically encompasses naturally-occurring truncated or secreted forms of the human lipocalin 2, naturally-occurring variant forms such as alternatively spliced forms and naturally-occurring allelic variants of human lipocalin 2. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally a variant has at least about 70%, including at least about 80%, such as at least about 85% amino acid sequence identity, including at least about 90% amino acid sequence identity or at least about 95% amino acid sequence identity with the native sequence polypeptide.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sequence positions of one or more muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) human lipocalin 2. Similarly, the position of a given nucleotide in accordance with the present disclosure which may be substituted may vary due to deletions or additional nucleotides elsewhere in a mutein or wild type human lipocalin 2 5'-untranslated region (UTR) including the promoter and/or any other regulatory sequences or gene (including exons and introns).

Thus, for a corresponding position in accordance with the disclosure, it is preferably to be understood that the positions of nucleotides/amino acids may differ in the indicated number than similar neighbouring nucleotides/amino acids, but said neighbouring nucleotides/amino acids, which may be exchanged, deleted, or added, are also comprised by the one or more corresponding positions.

In addition, for a corresponding position in a mutein based on a reference scaffold in accordance with the disclosure, it is preferably to be understood that the positions of nucleotides/amino acids are structurally corresponding to the positions elsewhere in a mutein or wild-type human lipocalin 2, even if they may differ in the indicated number.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

The word "detect", "detection", "detectable" or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgous monkeys and etc., to name only a few illustrative examples. Preferably, the mammal herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

III. DESCRIPTIONS OF FIGURES

Figure 1B:
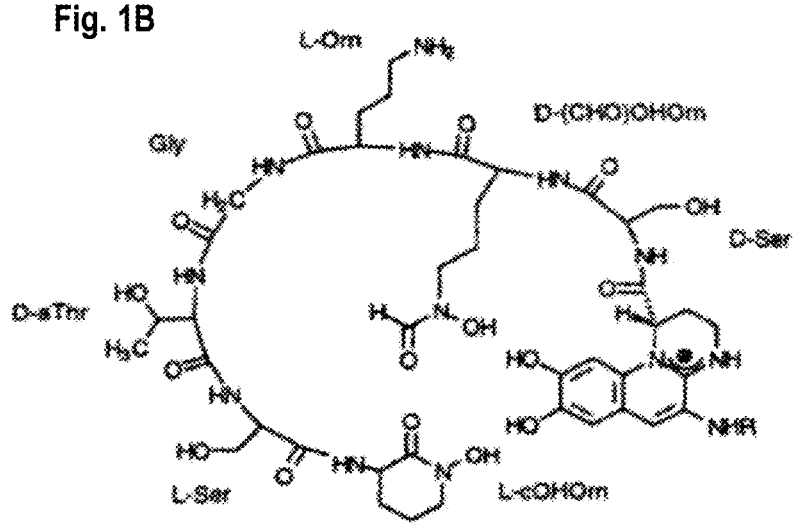
Figure 1C:
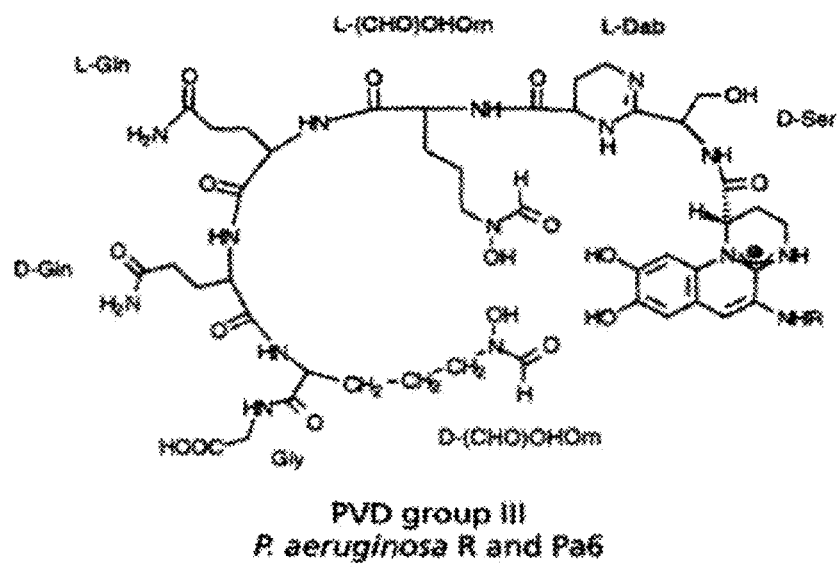
Figure 1D:
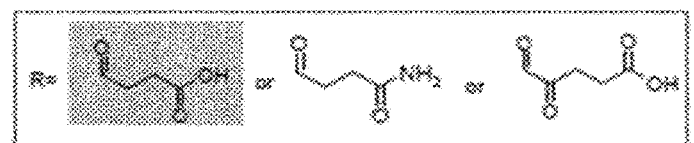
Figure 1E:
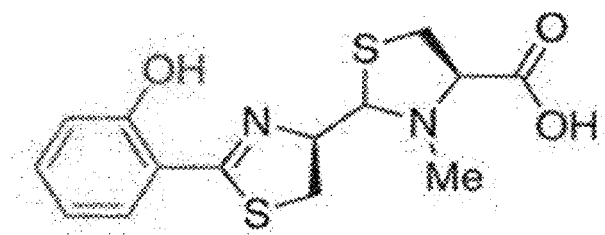

FIG. 1A-FIG. 1E: shows the structure of *P. aeruginosa* siderophores. FIG. 1A-C show the structures of the three *P. aeruginosa* pyoverdines. FIG. 1A: Structure of Pvd type I Birskot et al., 1989); FIG. 1B: Structure of Pvd type II (see Birskot et al., 1989); FIG. 1C: Structure of Pvd type III (Gipp et al., 1991); FIG. 1 D: R attached to the chromophore part can be a succinyl, succinamid or α-ketoglutaryl side chain; and FIG. 1 E: Structure of pyochelin (Brandel et al., 2011).

FIG. 2A-FIG. 2H: provides typical measurements of on-rate and off-rate by Surface Plasmon Resonance for Pvd I s (+Fe) binding to the lipocalin mutein SEQ ID NO: 16 (FIG. 2A), Pvd II s (+Fe) binding to the lipocalin mutein SEQ ID NO: 36 (FIG. 2B), Pvd III (+Fe) binding to the lipocalin mutein SEQ ID NO: 53 (FIG. 2C) and Pyochelin (+Fe) binding to SEQ ID NO: 62 (FIG. 2D). In addition, absence of binding of the respective siderophores at 1200 nM (200 nM for Pyochelin) to the negative control lipocalin SEQ ID NO: 64 is shown in FIG. 2E-FIG. 2H.

Figure 3:
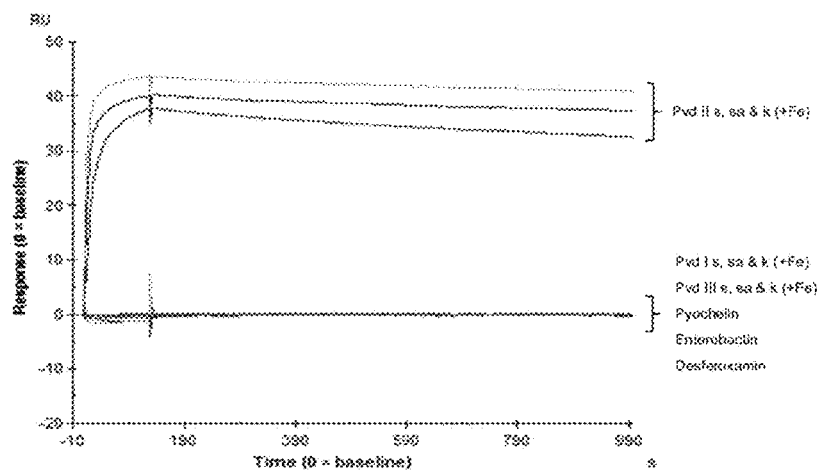

FIG. 3: shows an exemplary specificity and crossreactivity profile for the lipocalin mutein SEQ ID NO: 35 as determined by Surface Plasmon Resonance. Specific binding to Pyoverdin II succinyl, succinamid and α-ketoglutaryl is demonstrated, while absence of binding to Pyoverdines of type I and type III, Pyochelin, Enterobactin and Desferoxamin is shown. High concentrations of 2 μM are used for all analytes.

Figure 4A:
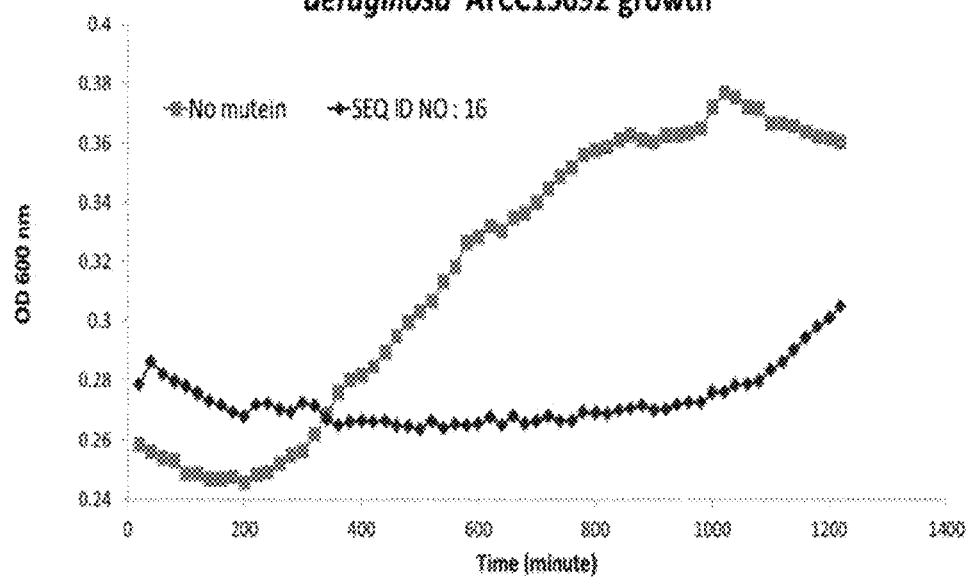
Figure 4B:
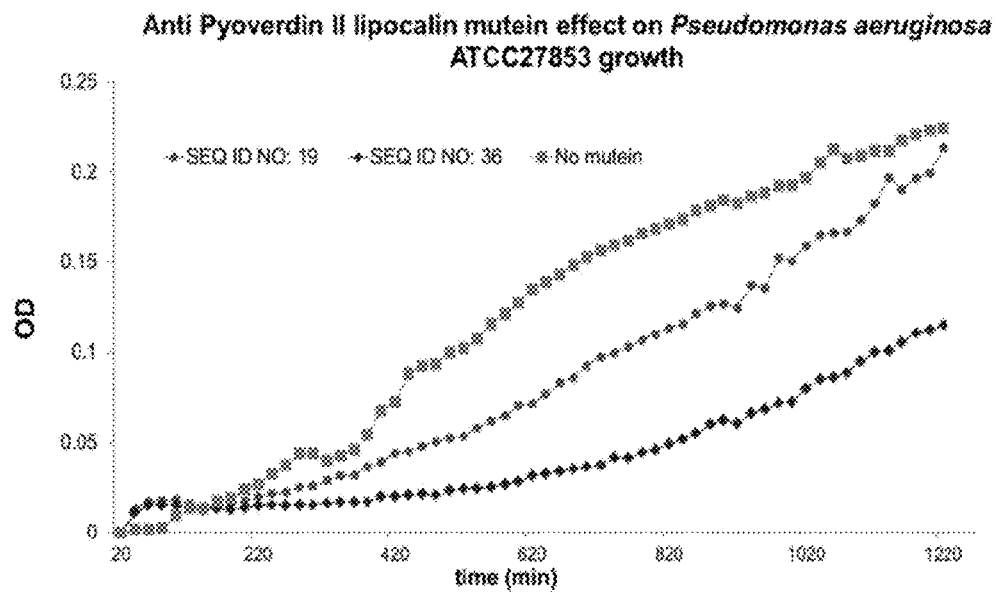
Figure 4C:
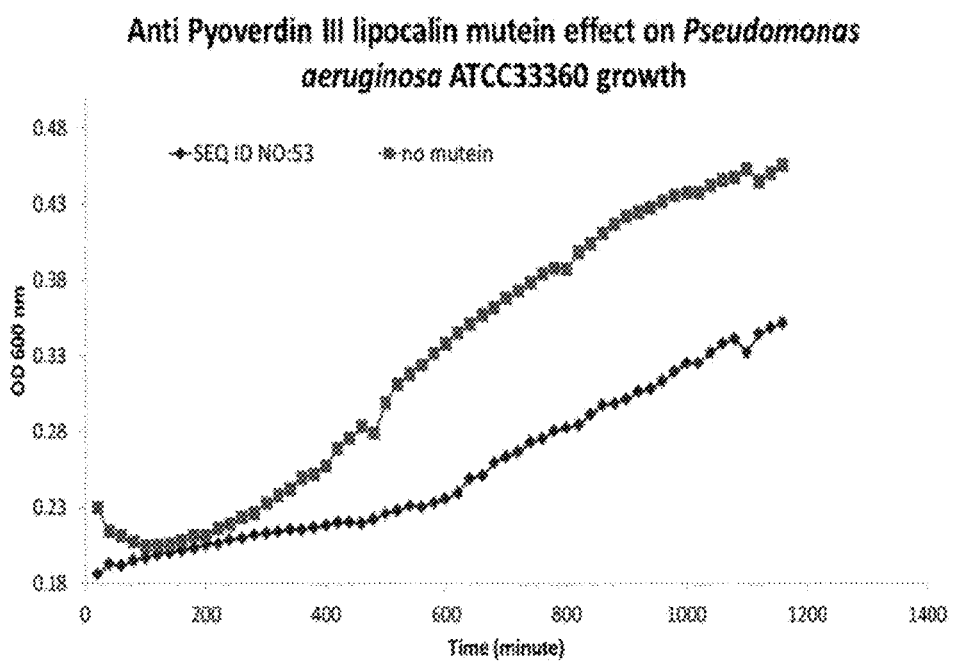
Figure 4D:
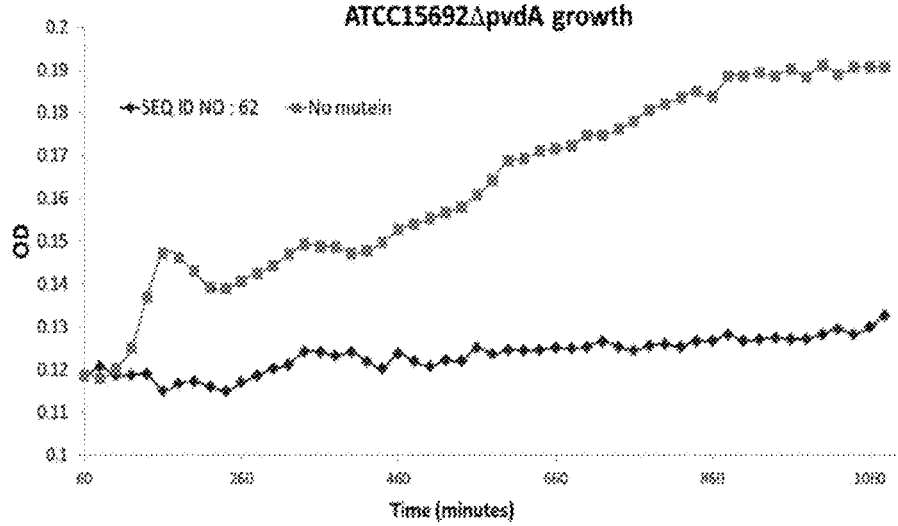

FIG. 4A-FIG. 4D: shows exemplary data from growth inhibition assay. FIG. 4A: Pvd I specific mutein SEQ ID NO: 16 shows growth inhibition of a Pvd I specific *P. aeruginosa* strain (ATCC27853) compared to the control culture growing without mutein. FIG. 4B: Pvd II specific muteins SEQ ID NOs: 19 and 36 show growth inhibition of a Pvd II specific *P. aeruginosa* strain (ATCC15692) compared to the control culture growing without mutein. SEQ ID NO: 36 has a higher binding affinity compared to SEQ ID NO: 19 and shows a greater growth inhibition. FIG. 4C: Pvd III specific mutein SEQ ID NO: 53 shows growth inhibition of a Pvd III specific *P. aeruginosa* strain (ATCC33360) compared to the control culture growing without mutein. FIG. 4D: Pch specific muteins SEQ ID NO: 62 shows growth inhibition of a Pvd I knock out *P. aeruginosa* strain (ATCC15692 ΔpvdA) relying on Pch for iron uptake compared to the control culture growing without mutein. 10 μM lipocalin muteins were applied in the assay.

Figure 5:
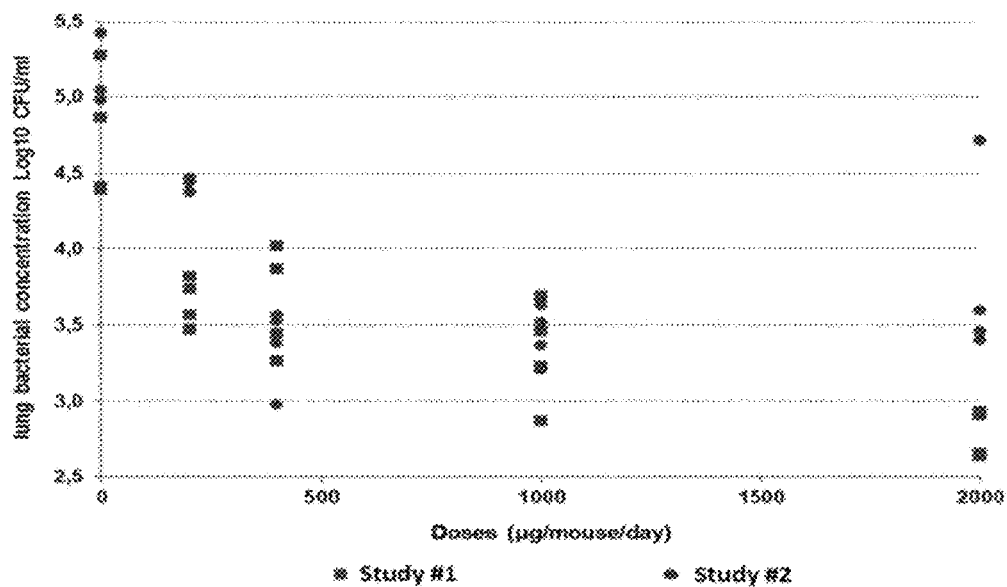

FIG. 5: shows in a *P. aeruginosa*-induced lung infection model in mice that administration of SEQ ID NO: 19, 1 hour before and at time of bacteria challenge, prevents the development of infection in mice in a dose-dependent manner. A significant prevention effect was observed starting from SEQ ID NO: 19 at 200 μg/mouse, with a maximal effect at 2000 μg/mouse.

FIG. 6: shows the amino acid sequence expressed for crystallisation including a start methionine at position 1, a lysine at position 2, a hexahistidine tag at position 3-8, a linker region of amino acids DYDIPTT at position 9-15 (SEQ ID NO: 132), the tobacco etch viral (TEV) protease cleavage site ENLYFQG at position 16-22 (SEQ ID NO: 133) followed by the amino acid sequence of the mutein of interest from position 23 onwards.

FIG. 7: shows the SEQ ID NO: 31—Pvd-Fe complex structure. An overlay of two SEQ ID NO: 31 molecules i.e. chain A and chain B from an asymmetric unit.

Figure 8:
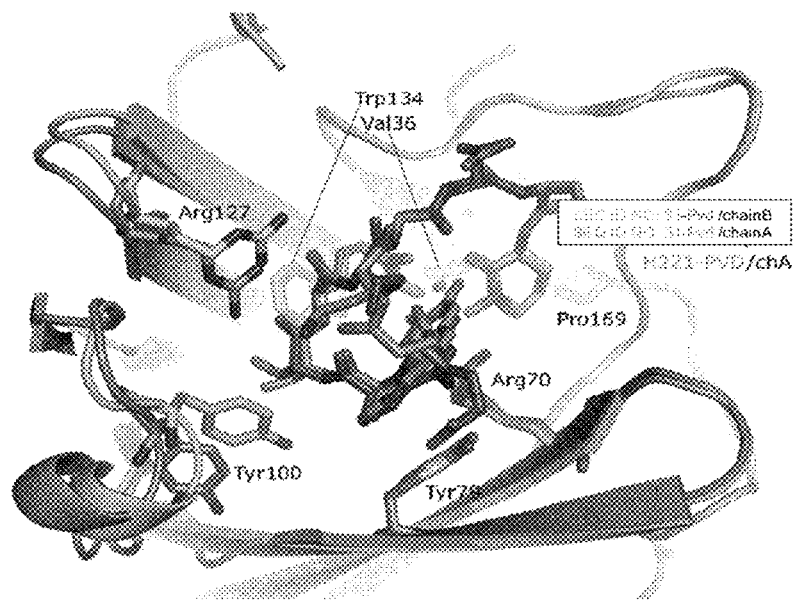

FIG. 8: shows SEQ ID NO: 31 and Pvd-Fe interactions. Two molecules from asymmetric unit are overlaid. Side chains interacting with Pvd-Fe are depicted.

Figure 9:
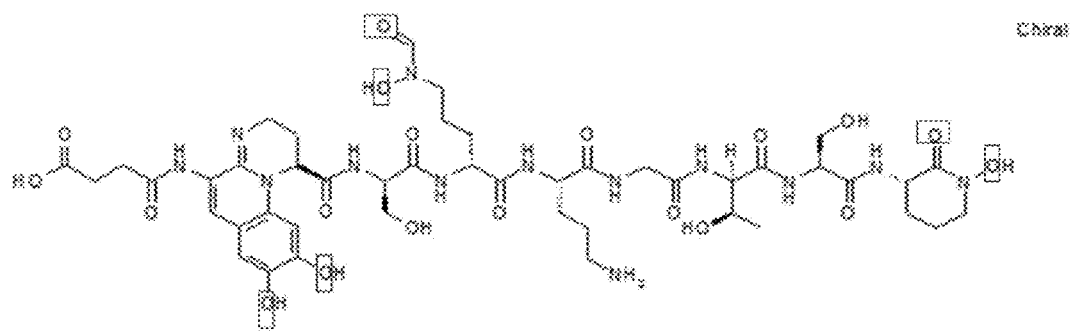

FIG. 9: shows the Pvd composition. Oxygen atoms involved in iron binding are boxed.

IV. DETAILED DESCRIPTION OF THE DISCLOSURE

The current disclosure provides a polypeptide having binding specificity for pyoverdine type I, II, III or pyochelin, wherein the polypeptide comprises an hNGAL mutein that binds pyoverdine type I, II, III or pyochelin with detectable affinity.

The term "human lipocalin 2" or "human Lcn 2" or "human NGAL" or "hNGAL" as used herein refers to the mature human neutrophil gelatinase-associated lipocalin (NGAL) with the SWISS-PROT/UniProt Data Bank Accession Number P80188. A human lipocalin 2 mutein of the disclosure may also be designated herein as "an hNGAL mutein". The amino acid sequence shown in SWISS-PROT/UniProt Data Bank Accession Number P80188 may be used as a preferred "reference sequence", more preferably the amino acid sequence shown in SEQ ID NO: 1 is used as reference sequence.

In some embodiments, an hNGAL mutein binding pyoverdine (type I, II or III) or pyochelin with detectable affinity may include at least one amino acid substitution of a native cysteine residue by another amino acid, for example, a serine residue. In some other embodiments, a mutein binding pyoverdine or pyochelin with detectable affinity may include one or more non-native cysteine residues substituting one or more amino acids of wild-type hNGAL. In a further particular embodiment, an hNGAL mutein according to the disclosure includes at least two amino acid substitutions of a native amino acid by a cysteine residue, hereby to form one or more cysteine bridges. In some embodiments, said cysteine bridge may connect at least two loop regions. The definition of these regions is used herein in accordance with Flower (Flower, 1996, supra, Flower, et al., 2000, supra) and Breustedt et al. (2005, supra).

In some embodiments, an hNGAL mutein of the disclosure does not bind to enterobactin.

In one aspect, the present disclosure includes various hNGAL muteins that bind pyoverdine or pyochelin with at least detectable affinity. In this sense, pyoverdine or pyochelin is regarded as a non-natural ligand of the reference wild-type hNGAL, where "non-natural ligand" refers to a compound that does not bind to wild-type human lipocalin 2 under physiological conditions. By engineering wild-type hNGAL with one or more mutations at certain sequence positions, the present inventors have demonstrated that high affinity and high specificity for the non-natural ligand, pyoverdine or pyochelin, is possible. In some embodiments, at 1, 2, 3, 4, 5, 6, 7, 8, 9, 10, 11, 12 or even more nucleotide triplet(s) encoding certain sequence positions on wild-type I human lipocalin 2, a random mutagenesis may be carried out through substitution at these positions by a subset of nucleotide triplets.

Further, the muteins of the disclosure may have a mutated amino acid residue at any one or more, including at least at any one, two, three, four, five, six, seven, eight, nine, ten, eleven or twelve, of the sequence positions corresponding to certain sequence positions of the linear polypeptide sequence of hNGAL, such as sequence positions 28, 34, 36, 39-42, 44-47, 49, 52, 54-55, 65, 68, 70, 72-75, 77, 79-81, 87, 96, 100, 103, 106, 108, 123, 125, 127, 132, 134, 141 and 145 of the linear polypeptide sequence of human NGAL (SEQ ID NO: 1).

A mutein of the disclosure may include the wild type (natural) amino acid sequence of the "parental" protein scaffold (such as hNGAL) outside the mutated amino acid sequence positions. In some embodiments, an hNGAL mutein according to the disclosure may also carry one or more amino acid mutations at a sequence position/positions as long as such a mutation does, at least essentially not hamper or not interfere with the binding activity and the folding of the mutein. Such mutations can be accomplished very easily on DNA level using established standard methods (Sambrook, J. et al. (2001) Molecular Cloning: A Laboratory Manual, 3rd Ed., Cold Spring Harbor Laboratory Press, Cold Spring Harbor, N.Y.). Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the human lipocalin 2 as long as these deletions or insertion result in a stable folded/functional mutein (for example, hNGAL muteins with truncated N- and C-terminus). In such mutein, for instance, one or more amino acid residues are added or deleted at the N- or C-terminus of the polypeptide. Generally such a mutein may have about at least 70%, including at least about 80%, such as at least about 85% amino acid sequence identity, with the amino acid sequence of the mature hNGAL. As an illustrative example, the present disclosure also encompasses hNGAL muteins as defined above, in which the four amino acid residues (G-N-I-K; positions 95-98; SEQ ID NO: 130) of the linear polypeptide sequence of the mature hNGAL have been deleted (e.g. SEQ ID NO: 46).

The amino acid sequence of an hNGAL mutein disclosed herein has a high sequence identity to the mature hNGAL (SEQ ID NO: 1) when compared to sequence identities with other lipocalins. In this general context, the amino acid sequence of a mutein of the disclosure is at least substantially similar to the amino acid sequence of the natural wild-type hNGAL, with the proviso that possibly there are gaps (as defined below) in an alignment that are the result of additions or deletions of amino acids. A respective sequence of a mutein of the disclosure, being substantially similar to the sequences of the mature hNGAL, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of the mature hNGAL, with the proviso that the altered position or sequence is retained and that one or more gaps are possible.

As used herein, a mutein of the disclosure "specifically binds" a target (for example, pyoverdine or pyochelin) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In one embodiment, the muteins of the disclosure are fused at its N-terminus and/or its C-terminus to a fusion partner which is a protein domain that extends the serum half-life of the mutein. In further particular embodiments, the protein domain is a Fc part of an immunoglobulin, a CH3 domain of an immunoglobulin, a CH4 domain of an immunoglobulin, an albumin binding peptide, or an albumin binding protein.

In another embodiment, the muteins of the disclosure are conjugated to a compound that extends the serum half-life of the mutein. More preferably, the mutein is conjugated to a compound selected from the group consisting of a polyalkylene glycol molecule, a hydroethylstarch, an Fc part of an immunoglobulin, a CH3 domain of an immoglobulin, a CH4 domain of an immunoglobulin, an albumin binding peptide, and an albumin binding protein.

In yet another embodiment, the current disclosure relates to a nucleic acid molecule comprising a nucleotide sequence encoding a mutein disclosed herein. The disclosure encompasses a host cell containing said nucleic acid molecule.
Muteins Specific for Pyoverdine.

Study of the *P. aeruginosa* isolates so far helped classify pyoverdine into three different types (Meyer et al., Use of Siderophores to Type Pseudomonads: The Three *Pseudomonas Aeruginosa* Pyoverdine Systems, Microbiology, 1997; vol. 143 no. 1 35-43). Roughly 42% of the *P. aeruginosa* isolates have a pyoverdine system identical to that of Pvd type I, 42% of the *P. aeruginosa* isolates behave like Pvd type II, while 16% of the *P. aeruginosa* isolates belong to Pvd type III, respectively (Cornelis et al., 1989a; Table 4). Each type has three members (subtypes) differing in the side chain which is succinyl, succinamid or α-ketoglutaryl, namely, Pvd type I succinyl, Pvd type I succinamid, Pvd type I α-ketoglutaryl, Pvd type II succinyl, Pvd type II succinamid, Pvd type II α-ketoglutaryl, Pvd type III succinyl, Pvd type III succinamid and Pvd type III a-ketoglutaryl.

To tackle *P. aeruginosa* producing different types of pyoverdine, the present disclosure provides hNGAL muteins directed against different types of pyoverdine. The disclosure also provides useful applications for such muteins, methods of making pyoverdine-binding hNGAL muteins described herein as well as compositions comprising such muteins. Pyoverdine-binding hNGAL muteins of the disclosure as well as compositions thereof may be used in methods of detecting pyoverdine in a sample or in methods of binding of pyoverdine in a subject. No such hNGAL muteins having these features attendant to the uses provided by present disclosure have been previously described.

Pyoverdine did not bind to the natural wild-type hNGAL, while hNGAL's natural ligand, enterobactin, docks into the calyx of hNGAL with high affinity. Pyoverdine, therefore, is a virulence factor and a stealth siderophore that evades hNGAL recognition, allowing *P. aeruginosa* to establish infection (Peek et al., Pyoverdine, the Major Siderophore in *Pseudomonas aeruginosa*, Evades NGAL Recognition, Interdisciplinary Perspectives on Infectious Diseases, 2012).

Accordingly, it is an object of the present disclosure to provide muteins derived from human neutrophil gelatinase associated lipocalin (NGAL), also termed as human lipocalin 2, which muteins, in contrast to nature wild-type hNGAL, have high specificity for pyoverdine.
Exemplary Muteins Specific for Pyoverdine.

In one aspect, the present disclosure relates to novel, specific-binding human lipocalin 2 (human Lcn2 or hNGAL) muteins specific for one type of pyoverdine, such as Pvd type I, Pvd type II or Pvd type III.

One embodiment of the current disclosure relates to a mutein that is capable of binding one type of pyoverdine with detectable affinity, such as an affinity measured by a $K_D$ of about 200 nM or lower, such as about 150 nM or lower.

In one aspect, the current disclosure provides an hNGAL mutein that is capable of binding Pvd type I complexed with iron with a $K_D$ of about 20 nM or lower, such as 15 nM or lower, for example, when measured by Biacore T200 instrument in an assay essentially described in Example 6.

In some further embodiments, one or more hNGAL muteins of this disclosure are capable of binding Pvd type I succinyl, Pvd type I succinamid and Pvd type I α-ketoglutaryl with and without complexed iron, with an affinity measured by an IC50 value of about 200 nM or lower, for example, when measured in an ELISA assay essentially described in Example 5.

In some embodiments, the mutein is capable of inhibiting iron uptake mediated by pyoverdine type I succinyl with an IC50 value of about 150 nM or lower in a competition ELISA format essentially described in Example 7.

In some embodiments, the mutein is capable of inhibiting bacterial growth of Pvd I strain in an assay essentially described in Example 8.

In this regard, the disclosure relates to a polypeptide, wherein said polypeptide includes an hNGAL mutein, and said hNGAL in comparison with the linear polypeptide sequence of the mature hNGAL, comprises at least 1, 2, 3, 4, 5, 6, 7, 8, 9, 10, 11, 12, 13, 14, 15, 16, 17, 18, 19, 20, 21, or even more, mutated amino acid residues at the sequence positions 28, 36, 39-41, 46, 49, 52, 54-55, 59, 65, 68, 70, 72-75, 77, 79-81, 87, 96, 100, 103, 106, 125, 127, 132, 134 and 136, and wherein said polypeptide binds Pvd type I, including Pvd type I succinyl, Pvd type I succinamid and Pvd type I α-ketoglutaryl.

In some embodiments, a Pvd-type-I-binding hNGAL mutein of the disclosure includes, at any one or more of the sequence positions 36, 40-41, 49, 52, 68, 70, 72-73, 77, 79, 81, 96, 100, 103, 106, 125, 127, 132 and 134 of the linear polypeptide sequence of the mature hNGAL (SEQ ID NO: 1), one or more of the following mutated amino acid residues: Leu 36→Asn, Thr, Val, Trp or Phe; Ala 40→Gly, Asn, Thr or Phe; Ile 41→Arg, Ala, Thr, Phe or Trp; Gln 49→Ile, Leu, Vla, Ala or Pro; Tyr 52→Met, Trp or Pro; Ser 68→Asp, Vla or Glu; Leu 70→Gln, Trp, Asp or Thr; Arg 72→Trp, Ala, Ser, Leu, Pro or Glu; Lys 73→Asp, Leu, Ala, Glu or Asn; Asp 77→Arg, Leu, Tyr, Ser, Gln, Thr, Ile or Asn; Trp 79→Gln, Asp, Ser, Arg, Met or Glu; Arg 81→Gln, Gly, Ile, Glu, His or Asp; Asn 96→His, Ile, Gly, Tyr or Asp; Tyr 100→Lys, Glu, Asn, Ser, Phe or Tyr; Leu 103→Lys, Pro, Gln, His, Asp, Tyr, Glu, Trp or Asn; Tyr 106→His, Gln or Phe; Lys 125 Arg, Ser, Trp, Tyr, Val or Gly; Ser 127→Trp, Asn, Ala, Thr, Tyr, His, Ile, Val or Asp; Tyr 132→Trp, Asn, Gly or Lys; and Lys 134→Asn, His, Trp, Gly, Gln or Asp. In some embodiments, an hNGAL mutein of the disclosure includes two or more, such as 3, 4, 5, 6, 7, 8, 9, 10, 11, 12, or even more or all mutated amino acid residues at these sequence positions of the mature hNGAL.

Additionally, a Pvd-type-I-binding hNGAL mutein according to the disclosure may also comprise the following substitution in comparison with the linear polypeptide sequence of the mature hNGAL: Gln 28→His; Lys 46→Glu; Thr 54→Vla or Ala; Ile 55→Vla; Lys 59→Arg; Asn 65→Asp or Gln; Ile 80→Thr; Cys 87→Ser or Asn; and Thr 136→Ala.

In some additional embodiments, an hNGAL mutein of the disclosure, which binds to Pvd type I, includes the following amino acid replacements in comparison with the linear polypeptide sequence of the mature hNGAL:
Gln 28→His; Leu 36→Asn; Ala 40→Gly; Ile 41→Trp; Gln 49→Ile; Tyr 52→Met; Ser 68→Val; Leu 70→Gln; Arg 72→Trp; Lys 73→Asp; Asp 77→Leu; Trp 79→Gln; Arg 81→Gln; Cys 87→Ser; Asn 96→His; Tyr 100→Lys; Leu 103→His; Tyr 106→His; Lys 125→Arg; Ser 127→Trp; Tyr 132→Trp; Lys 134→Asp;
Gln 28 His; Leu 36→Thr; Ala 40→Gly; Ile 41→Phe; Gln 49→Leu; Tyr 52→Trp; Leu 70→Trp; Arg 72→Ala; Lys 73→Leu; Asp 77→Tyr; Trp 79→Asp; Arg 81→Gly; Cys 87→Ser; Asn 96→Ile; Tyr 100→Glu; Leu 103→His; Tyr 106→Gln; Lys 125→Trp; Ser 127→Asn; Tyr 132→Asn; Lys 134→Gln;
Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Glu; Asp 77→Ser; Trp 79→Ser; Arg 81→Ile; Cys 87→Ser; Asn 96→Gly; Tyr 100→Asn; Leu 103→Lys; Tyr 106→His; Lys 125→Tyr; Ser 127→Ala; Tyr 132→Gly; Lys 134→Asn;
Gln 28→His; Leu 36→Phe; Ala 40→Asn; Ile 41→Arg; Gln 49→Pro; Tyr 52→Met; Ser 68→Asp; Leu 70→Thr; Arg 72→Glu; Lys 73→Ala; Asp 77→Arg; Trp 79→Arg; Arg 81→Ile; Cys 87→Ser; Asn 96→Tyr; Tyr 100→Lys; Leu 103→Pro; Tyr 106→Phe; Lys 125→Ser; Ser 127→Thr; Tyr 132→Trp; Lys 134→Gly;
Gln 28→His; Ala 40→Gly; Ile 41→Trp; Gln 49→Val; Tyr 52→Met; Ser 68→Val; Leu 70→Asp; Arg 72→Glu; Lys 73→Leu; Asp 77→Arg; Trp 79→Met; Arg 81→Glu; Cys 87→Ser; Asn 96→Asp; Tyr 100→Phe; Leu 103→Trp; Tyr 106→Gln; Lys 125→Gly; Ser 127→Tyr; Tyr 132→Trp; Lys 134→His;
Gln 28→His; Leu 36→Val; Ala 40→Phe; Ile 41→Phe; Gln 49→Ala; Tyr 52→Pro; Ser 68→Glu; Leu 70→Trp; Arg 72→Leu; Lys 73→Asn; Asp 77→Gln; Trp 79→Glu; Arg 81→His; Cys 87→Ser; Asn 96→Tyr; Leu 103→Tyr; Tyr 106→His; Lys 125→Val; Ser 127→His; Tyr 132→Lys; Lys 134→Trp;
Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Ile; Tyr 132→Gly; Lys 134→Asn;
Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Asp; Asp 77→Ser; Trp 79→Ser; Arg 81→Ile; Cys 87→Ser; Asn 96→Gly; Tyr 100→Asn; Leu 103→Asp; Tyr 106→His; Lys 125→Tyr; Ser 127→Val; Tyr 132→Gly; Lys 134→Asn;
Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Glu; Asp 77→Thr; Trp 79→Ser; Arg 81→Ile; Cys 87→Ser; Asn 96→Asp; Tyr 100→Asn; Leu 103→Glu; Tyr 106→His; Lys 125→Tyr; Ser 127→Asp; Tyr 132→Gly; Lys 134→Asn;
Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Asp; Asp 77→Val; Trp 79→Ser; Arg 81→Ile; Cys 87-4 Ser; Asn 96→Gly; Tyr 100→Asn; Leu 103→Asn; Tyr 106→His; Lys 125→Tyr; Ser 127→Vla; Tyr 132→Gly; Lys 134→Asn;
Gln 28→His; Ala 40→Gly; Ile 41→Trp; Gln 49→Leu; Tyr 52→Met; Ser 68→Val; Leu 70→Asp; Arg 72→Glu; Lys 73→Leu; Asp 77→Arg; Trp 79→Met; Arg 81→Glu; Cys 87→Ser; Asn 96→Asp; Tyr 100→Ser; Leu 103→Trp; Tyr 106→Gln; Lys 125→Gly; Ser 127→Tyr; Tyr 132→Trp; Lys 134→His;
Gln 28→His; Leu 36→Trp; Ala 40→Thr; Ile 41→Thr; Gln 49→Pro; Tyr 52→Pro; Thr 54→Val; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Thr; Tyr 132→Gly; Lys 134→Asn;
Gln 28→His; Ala 40→Gly; Ile 41→Trp; Lys 46→Glu; Gln 49→Leu; Tyr 52→Met; Thr 54→Ala; Ile 55→Vla; Lys 59→Arg; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87→Asn; Asn 96→Asp; Tyr 100→sER; Leu 103→Trp; Tyr 106→Gln; Lys 125→Gly; Ser 127→Tyr; Tyr 132→Trp; Lys 134→His;
Leu 36→Trp; Asn 39→Asp; Ala 40→Thr; Ile 41→Thr; Gln 49→Pro; Tyr 52→Pro; Thr 54→Val; Asn 65→Asp; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125 Tyr; Ser 127→Thr; Tyr 132→Gly; Lys 134→Asn; Thr 136→Ala;
Leu 36→Trp; Ala 40→Thr; Ile 41→Ala; Gln 49→Pro; Tyr 52→Pro; Thr 54→Val; Asn 65→Asp; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Thr; Tyr 132→Gly; Lys 134→Asn; Thr 136→Ala;

Gln 28→His; Ala 40→Gly; Ile 41→Trp; Lys 46→Glu; Gln 49→Leu; Tyr 52→Met; Thr 54→Ala; Ile 55→Vla; Lys 59→Arg; Asn 65→Asp; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87→Asn; Asn 96→Asp; Tyr 100→sER; Leu 103→Trp; Tyr 106→Gln; Lys 125→Gly; Ser 127→Tyr; Tyr 132→Trp; Lys 134→His; or

Gln 28→His; Ala 40→Gly; Ile 41→Trp; Lys 46→Glu; Gln 49→Leu; Tyr 52→Met; Thr 54→Ala; Ile 55→Vla; Lys 59→Arg; Asn 65→Gln; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87→Asn; Asn 96→Asp; Tyr 100→sER; Leu 103→Trp; Tyr 106→Gln; Lys 125→Gly; Ser 127→Tyr; Tyr 132→Trp; Lys 134→His.

In the residual region, i.e. the region differing from sequence positions 28, 36, 39-41, 46, 49, 52, 54-55, 59, 65, 68, 70, 72-75, 77, 79-81, 87, 96, 100, 103, 106, 125, 127, 132, 134 and 136, an hNGAL mutein of the disclosure may include the wild type (natural) amino acid sequence outside the mutated amino acid sequence positions.

In further particular embodiments, a mutein according to the current disclosure comprises an amino acid sequence selected from the group consisting of SEQ ID NOs: 2-18 or a fragment or variant thereof.

The amino acid sequence of a Pvd-type-I-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 2-18.

The disclosure also includes structural homologues of an hNGAL mutein having an amino acid sequence selected from the group consisting of SEQ ID NOs: 2-18, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said hNGAL mutein.

A Pvd-type-I-binding hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to Pvd type I, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

In another aspect, the current disclosure provides an hNGAL mutein that binds Pvd type II complexed with iron with a $K_D$ of about 20 nM or lower, such as 5 nM or lower, for example, when measured by Biacore T200 instrument in an assay essentially described in Example 6.

In some still further embodiments, one or more hNGAL muteins of this disclosure are capable of binding Pvd type II succinyl, Pvd type II succinamid and Pvd type II a-ketoglutaryl with and without complexed iron, with an affinity measured by an IC50 value of about 200 nM or lower, for example, when measured in an ELISA assay essentially described in Example 5.

In some embodiments, the mutein is capable of inhibiting iron uptake mediated by pyoverdine type II succinyl with an IC50 value of about 150 nM or lower in a competition ELISA format essentially described in Example 7.

In some embodiments, the mutein is capable of inhibiting bacterial growth of Pvd II strain in an assay essentially described in Example 8.

In some other embodiments, the mutein is capable of inhibiting or lessening growth of *P. aeruginosa* stains expressing pyoverdine type II in an assay essentially described in Example 10.

In this regard, the disclosure relates to a polypeptide, wherein said polypeptide includes an hNGAL mutein, and said hNGAL in comparison with the linear polypeptide sequence of the mature hNGAL, comprises at least 1, 2, 3, 4, 5, 6, 7, 8, 9, 10, 11, 12, 13, 14, 15, 16, 17, 18, 19, 20, 21, or even more, mutated amino acid residues at the sequence positions 28, 36, 40-41, 49, 52, 54, 65, 68, 70, 72-75, 77, 79, 81, 87, 96, 100, 103, 106, 125, 127, 132 and 134, and wherein said polypeptide binds Pvd type II.

In some embodiments, a Pvd-type-II-binding hNGAL mutein of the disclosure includes, at any one or more of the sequence positions 36, 40-41, 49, 52, 68, 70, 72-73, 77, 79, 81, 87, 96, 100, 103, 106, 125, 127, 132 and 134 of the linear polypeptide sequence of the mature hNGAL (SEQ ID NO: 1), one or more of the following mutated amino acid residues: Leu 36→Asn, Ile or Val; Ala 40→Glu, Gly, Asn, Thr or His; Ile 41→Arg, Val or Thr; Gln 49→Gly, Ala or Pro; Tyr 52→Asn, Gly, Trp or Pro; Ser 68→Asp, Arg or Glu; Leu 70→Arg or Trp; Arg 72→His, Ile, Ala, Ser or Gly; Lys 73→Asn, Met, Pro, Phe, Gln or Arg; Asp 77→His, Ile, Met, Lys, Gly or Asn; Trp 79→Ser, Tyr, Ala, Asp, Phe or Trp; Arg 81→Glu, Ser, Tyr or Asp; Asn 96→Met, Ile, Arg, Asp, Lys, Asn or Ala; Tyr 100→Lys, Glu, Asn, Ser, Phe or Tyr; Leu 103→Thr, Ile, Gln, Gly, Met, His, Trp or Val; Tyr 106→Met, Gln, Ala, Ile, Asn, Gly, Met or Phe; Lys 125→Ala, Ile or Asn; Ser 127→Lys, Arg, Ser, Met, Asp or Asn; Tyr 132→Met, Phe, Asn, Ala, Ile, Gly or Val; and Lys 134→Trp or Tyr. In some embodiments, an hNGAL mutein of the disclosure Includes two or more, such as 3, 4, 5, 6, 7, 8, 9, 10, 11, 12, or even more or all mutated amino acid residues at these sequence positions of the mature hNGAL.

Additionally, a Pvd-type-II-binding hNGAL mutein according to the disclosure may also comprise the following substitution in comparison with the linear polypeptide sequence of the mature hNGAL: Gln 28→His; Thr 54→Ala; Asn 65→Asp or Gln and Cys 87→Ser.

In some additional embodiments, an hNGAL mutein of the disclosure, which binds to Pvd type II, includes the following amino acid replacements in comparison with the linear polypeptide sequence of the mature hNGAL:

Gln 28→His; Leu 36→Val; Ala 40→Glu; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Tyr 100→Asn; Leu 103→Gln; Tyr 106→Met; Ser 127→Lys; Tyr 132→Gly; Lys 134→Trp;

Gln 28→His; Ala 40→Thr; Ile 41→Ile; Gln 49→Gly; Tyr 52→Asn; Ser 68→Asp; Leu 70→Arg; Arg 72→Ile; Lys 73→Met; Asp 77→His; Trp 79→Tyr; Arg 81→Glu; Cys 87→Ser; Asn 96→Ile; Tyr 100→Asn; Leu 103→Thr; Tyr 106→Gln; Lys 125→Ile; Ser 127→Arg; Tyr 132→Met; Lys 134→Trp;

Gln 28→His; Leu 36→Ile; Ala 40→Thr; Ile 41→Val; Gln 49→Gly; Tyr 52→Pro; Ser 68→Glu; Leu 70→Arg; Arg 72→Ala; Lys 73→Pro; Asp 77→Ile; Trp 79→Ser; Arg

81→Ser; Cys 87→Ser; Asn 96→Met; Tyr 100→Ser; Leu 103→Gly; Tyr 106→Ala; Lys 125→Lys; Tyr 132→Val; Lys 134→Trp;

Gln 28→His; Ala 40→Asn; Gln 49→Ala; Tyr 52→Pro; Ser 68→Glu; Leu 70→Arg; Arg 72→Ser; Lys 73→Gln; Asp 77→Met; Trp 79→Ala; Arg 81→Tyr; Cys 87→Ser; Asn 96→Arg; Tyr 100→Pro; Leu 103→Thr; Tyr 106→Ile; Lys 125→Lys; Ser 127→Met; Tyr 132→Phe; Lys 134→Trp;

Gln 28→His; Ala 40→His; Gln 49→Ala; Tyr 52→Pro; Ser 68→Glu; Leu 70→Asp; Arg 72→Gly; Lys 73→Arg; Asp 77→His; Trp 79→Trp; Arg 81→Glu; Cys 87→Ser; Asn 96→Arg; Tyr 100→Asp; Leu 103→Met; Tyr 106→Phe; Lys 125→Ala; Ser 127→Asp; Tyr 132→Asn; Lys 134→Trp;

Gln 28→His; Leu 36→Asn; Ala 40→Gly; Ile 41→Arg; Gln 49→Pro; Tyr 52→Trp; Ser 68→Arg; Leu 70→Trp; Arg 72→Asn; Lys 73→Gln; Asp 77→Lys; Trp 79→Asp; Arg 81→Glu; Cys 87→Ser; Asn 96→Asp; Tyr 100→Thr; Leu 103→Trp; Tyr 106→Asn; Lys 125→Asn; Ser 127→Met; Tyr 132→Ile; Lys 134→Tyr;

Gln 28→His; Leu 36→Vla; Ala 40→Thr; Ile 41→Thr; Gln 49→Gly; Tyr 52→Gly; Ser 68→Glu; Leu 70→Arg; Arg 72→Gly; Lys 73→Arg; Asp 77→Gly; Trp 79→Trp; Arg 81→Glu; Cys 87→Ser; Asn 96→Ala; Tyr 100→Trp; Leu 103→Ile; Tyr 106→Gly; Lys 125→Lys; Ser 127→Asn; Tyr 132→Val; Lys 134→Trp;

Gln 28→His; Leu 36→Val; Ala 40→Glu; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

Gln 28→His; Leu 36→Val; Ala 40→Thr; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Leu 103→Gln; Tyr 106→Met; Ser 127→Lys; Tyr 132→Val; Lys 134→Trp;

Gln 28→His; Leu 36→Val; Ala 40→Thr; Ile 41→Val; Gln 49→Gly; Tyr 52→Pro; Ser 68→Glu; Leu 70→Arg; Arg 72→His; Asp 77→Asn; Trp 79→Phe; Arg 81→Glu; Cys 87→Ser; Asn 96→Lys; Tyr 100→His; Leu 103→Gln; Tyr 106→Met; Ser 127→Lys; Tyr 132→Ala; Lys 134→Trp;

Gln 28→His; Leu 36→Val; Ala 40→Gly; Ile 41→Val; Gln 49→Gly; Tyr 52→Pro; Ser 68→Glu; Leu 70→Arg; Arg 72→His; Lys 73→Asn; Asp 77→Asn; Trp 79→Trp; Arg 81→Glu; Cys 87→Ser; Tyr 100→Asn; Leu 103→His; Tyr 106→Met; Ser 127→Lys; Tyr 132→Gly; Lys 134→Trp;

Gln 28→His; Leu 36→Val; Ala 40→Thr; Ile 41→Ile; Gln 49→Gly; Tyr 52→Asn; Ser 68→Asp; Leu 70→Arg; Arg 72→Ile; Lys 73→Phe; Asp 77→His; Trp 79→Tyr; Arg 81→Asp; Cys 87→Ser; Leu 103→Met; Tyr 106→Gln; Lys 125→Ile; Ser 127→Arg; Tyr 132→Ile; Lys 134→Trp;

Gln 28→His; Leu 36→Val; Ala 40→Thr; Ile 41→Ile; Gln 49→Gly; Tyr 52→Asn; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp;

Gln 28→His; Leu 36→Val; Ala 40→Glu; Ile 41→Val; Gln 49→Gly; Tyr 52→Pro; Asn 65→Asp; Ser 68→Glu; Leu 70→Arg; Arg 72→His; Lys 73→Asn; Asp 77→Asn; Trp 79→Phe; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

Gln 28→His; Leu 36→Val; Ala 40→Glu; Ile 41→Val; Gln 49→Gly; Tyr 52→Pro; Asn 65→Gln; Ser 68→Glu; Leu 70→Arg; Arg 72→His; Lys 73→Asn; Asp 77→Asn; Trp 79→Phe; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

Gln 28→His; Leu 36→Val; Ala 40→Thr; Ile 41→Ile; Gln 49→Gly; Tyr 52→Asn; Thr 54→Ala; Asn 65→Asp; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp;

Gln 28→His; Leu 36→Val; Ala 40→Thr; Ile 41→Ile; Gln 49→Gly; Tyr 52→Asn; Thr 54→Ala; Asn 65→Gln; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp;

Leu 36→Val; Ala 40→Thr; Ile 41→Ile; Gln 49→Gly; Tyr 52→Asn; Thr 54→Ala; Asn 65→Asp; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp; or

Gln 28→His; Leu 36→Val; Ala 40→Thr; Ile 41→Ile; Gln 49→Gly; Tyr 52→Asn; Asn 65→Gln; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp.

In the residual region, i.e. the region differing from sequence positions 28, 36, 40-41, 49, 52, 54, 65, 68, 70, 72-75, 77, 79, 81, 87, 96, 100, 103, 106, 125, 127, 132 and 134, an hNGAL mutein of the disclosure may include the wild type (natural) amino acid sequence outside the mutated amino acid sequence positions.

In further particular embodiments, a mutein according to the current disclosure comprises an amino acid sequence selected from the group consisting of SEQ ID NOs: 19-37 or a fragment or variant thereof.

The amino acid sequence of a Pvd-type-II-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 19-37.

The disclosure also includes structural homologues of an hNGAL mutein having an amino acid sequence selected from the group consisting of SEQ ID NOs: 19-37, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said hNGAL mutein.

A Pvd-type-II-binding hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to Pvd type I, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

In still another aspect, the current disclosure provides an hNGAL mutein that binds Pvd type III complexed with iron with a $K_D$ of about 20 nM or lower, such as 10 nM or lower, for example, when measured by Biacore T200 instrument in an assay essentially described in Example 6.

In some still further embodiments, one or more hNGAL muteins of this disclosure are capable of binding Pvd type III succinyl, Pvd type III succinamid and Pvd type II a-keto-glutaryl with and without complexed iron, with an affinity measured by an IC50 value of about 200 nM or lower, for example, when measured in an ELISA assay essentially described in Example 5.

In some embodiments, the mutein is capable of inhibiting iron uptake mediated by pyoverdine type III with an IC50 value of about 150 nM or lower in a competition ELISA format essentially described in Example 7.

In some embodiments, the mutein is capable of inhibiting bacterial growth of Pvd III strain in an assay essentially described in Example 8.

In this regard, the disclosure relates to a polypeptide, wherein said polypeptide includes an hNGAL mutein, and said hNGAL in comparison with the linear polypeptide sequence of the mature hNGAL, comprises at least 1, 2, 3, 4, 5, 6, 7, 8, 9, 10, 11, 12, 13, 14, 15, 16, 17, 18, 19, 20, 21, or even more, mutated amino acid residues at the sequence positions 28, 36, 40-42, 45-47, 49, 52, 65, 68, 70, 72-73, 77, 79, 81, 87, 96, 100, 103, 105-106, 125, 127, 132, 134 and 145, and wherein said polypeptide binds Pvd type III.

In some embodiments, a Pvd-type-III-binding hNGAL mutein of the disclosure includes, at any one or more of the sequence positions 36, 40-41, 49, 52, 68, 70, 72-73, 77, 79, 81, 96, 100, 103, 106, 125, 127, 132 and 134 of the linear polypeptide sequence of the mature hNGAL (SEQ ID NO: 1), one or more of the following mutated amino acid residues: Leu 36→Phe or Glu; Ala 40→Trp, Leu or Arg; Ile 41→Met, Arg, Ala, Leu or Trp; Gln 49→His, Ile, Arg, Lys, Met or Pro; Tyr 52→Asn, Tyr, Arg, Ser or Met; Ser 68→Asp, Asn, Glu or Gln; Leu 70→Lys, Asn or Arg; Arg 72→Leu, Arg, Gln or Tyr; Lys 73→His, Leu, Ala, Pro, Gln or Tyr; Asp 77→Ala, Ile, Lys, Gln or Arg; Trp 79→Ser or Asp; Arg 81→His, Ala, Ser or Val; Asn 96→Met, Ile, Arg, Gly, Leu or Val; Tyr 100→Ala, Ile, Asn, Pro or Asp; Leu 103→Gln, Gly, Phe or Pro; Tyr 106→Glu; Lys 125→Trp or Thr; Ser 127→Val, His, Ile, Phe or Ala; Tyr 132→Phe; and Lys 134→Trp, Gln or Glu. In some embodiments, an hNGAL mutein of the disclosure includes two or more, such as 3, 4, 5, 6, 7, 8, 9, 10, 11, 12, or even more or all mutated amino acid residues at these sequence positions of the mature hNGAL.

Additionally, a Pvd-type-III-binding hNGAL mutein according to the disclosure may also comprise the following substitution in comparison with the linear polypeptide sequence of the mature hNGAL: Gln 28→His; Leu 42→Arg; Asp 45→Gly; Lys 46→Arg; Asp 47→Asn; Asn 65→Asp; Cys 87→Ser; Ser 105→Pro and Thr 145→Pro.

In some additional embodiments, an hNGAL mutein of the disclosure, which binds to Pvd type III, includes the following amino acid replacements in comparison with the linear polypeptide sequence of the mature hNGAL:

Gln 28→His; Leu 36→Phe; Ala 40→Trp; Ile 41→Met; Gln 49→His; Tyr 52→Asn; Ser 68→Glu; Leu 70→Lys; Arg 72→Gln; Lys 73→Ala; Asp 77→Ile; Trp 79→Ser; Arg 81→His; Cys 87→Ser; Asn 96→Ile; Tyr 100→Asn; Leu 103→Gly; Tyr 106→Glu; Lys 125→Trp; Ser 127→His; Tyr 132→Phe; Lys 134→Gln;

Gln 28→His; Leu 36→Phe; Ala 40→Arg; Ile 41→Trp; Gln 49→Ile; Tyr 52→Tyr; Ser 68→Gln; Leu 70→Asn; Arg 72→Trp; Lys 73→Leu; Asp 77→Ala; Trp 79→Ser; Arg 81→Ser; Cys 87→Ser; Asn 96→Arg; Tyr 100→Ile; Leu 103→Pro; Tyr 106→Glu; Lys 125→Thr; Ser 127→Ile; Tyr 132→Phe; Lys 134→Glu;

Gln 28→His; Leu 36→Phe; Ala 40→Leu; Ile 41→Leu; Gln 49→Arg; Tyr 52→Arg; Ser 68→Asp; Leu 70→Arg; Arg 72→Leu; Lys 73→Tyr; Asp 77→Ile; Trp 79→Ser; Arg 81→Ala; Cys 87→Ser; Asn 96→Gly; Tyr 100→Ala; Leu 103→Phe; Tyr 106→Glu; Lys 125→Trp; Ser 127→Ala; Lys 134→Glu;

Gln 28→His; Leu 36→Phe; Ala 40→Trp; Ile 41→Arg; Gln 49→Pro; Tyr 52→Ser; Ser 68→Asn; Leu 70→Arg; Arg 72→Trp; Lys 73→Pro; Asp 77→Arg; Trp 79→Ser; Arg 81→Ser; Cys 87→Ser; Asn 96→Met; Tyr 100→Pro; Leu 103→Gly; Tyr 106→Glu; Lys 125→Trp; Ser 127→Phe; Tyr 132→Phe; Lys 134→Glu;

Gln 28→His; Leu 36→Glu; Ala 40→Leu; Ile 41→Ala; Gln 49→Lys; Tyr 52→Met; Ser 68→Glu; Leu 70→Arg; Lys 73→His; Asp 77→Gln; Trp 79→Asp; Arg 81→Ala; Cys 87→Ser; Asn 96→Leu; Tyr 100→Asp; Leu 103→Gln; Tyr 106→Glu; Ser 127→Val; Tyr 132→Phe; Lys 134→Trp;

Gln 28→His; Leu 36→Glu; Ala 40→Leu; Ile 41→Ala; Gln 49→Met; Tyr 52→Met; Ser 68→Glu; Leu 70→Arg; Lys 73→Gln; Asp 77→Lys; Trp 79→Asp; Arg 81→Vla; Cys 87→Ser; Asn 96→Leu; Tyr 100→Asp; Leu 103→Gln; Tyr 106→Glu; Ser 127→Val; Tyr 132→Phe; Lys 134→Trp;

Gln 28→His; Leu 36→Glu; Ala 40→Leu; Ile 41→Thr; Gln 49→Met; Tyr 52→Met; Ser 68→Glu; Leu 70→Arg; Lys 73→Arg; Asp 77→Lys; Trp 79→Asp; Arg 81→Vla; Cys 87→Ser; Asn 96→Vla; Tyr 100→Asp; Leu 103→Gln; Tyr 106→Glu; Ser 127→Val; Tyr 132→Phe; Lys 134→Trp;

Gln 28→His; Leu 36→Glu; Ala 40→Leu; Ile 41→Ala; Gln 49→Met; Tyr 52→Met; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Tyr 106→Glu; Ser 127→Val; Tyr 132→Phe; Lys 134→Trp;

Gln 28→His; Leu 36→Glu; Ala 40→Leu; Ile 41→Ala; Gln 49→Lys; Tyr 52→Met; Ser 68→Glu; Leu 70→Arg; Lys 73→Tyr; Asp 77→Gln; Trp 79→Asp; Arg 81→Vla; Cys 87→Ser; Asn 96→-; Tyr 100→Glu; Leu 103→Gln; Tyr 106→Glu; Ser 127→Val; Tyr 132→Phe; Lys 134→Trp;

Gln 28→His; Leu 36→Glu; Ala 40→Leu; Ile 41→Ala; Leu 42→Arg; Gln 49→Met; Tyr 52→Met; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

Gln 28→His; Leu 36→Glu; Ala 40→Leu; Ile 41→Ala; Asp 47→Asn; Gln 49→Met; Tyr 52→Met; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; Thr 145→Pro;

Gln 28→His; Leu 36→Glu; Ala 40→Leu; Ile 41→Ala; Asp 45→Gly; Lys 46→Arg; Gln 49→Met; Tyr 52→Met; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

Gln 28→His; Leu 36→Glu; Ala 40→Leu; Ile 41→Ala; Leu 42→Arg; Gln 49→Met; Tyr 52→Met; Asn 65→Asp; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

Gln 28→His; Leu 36→Glu; Ala 40→Leu; Ile 41→Ala; Asp 47→Asn; Gln 49→Met; Tyr 52→Met; Asn 65→Asp; Ser 68→Glu; Leu 70→Arg; Lys 73→His; Asp 77→Lys; Trp

79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; Thr 145→Pro; Gln 28→His; Leu 36→Glu; Ala 40→Leu; Ile 41→Ala; Asp 45→Gly; Lys 46→Arg; Gln 49→Met; Tyr 52→Met; Asn 65→Asp; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; or Leu 36→Glu; Ala 40→Leu; Ile 41→Ala; Leu 42→Arg; Gln 49→Met; Tyr 52→Met; Asn 65→Asp; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp.

In the residual region, i.e. the region differing from sequence positions 28, 36, 40-42, 45-47, 49, 52, 65, 68, 70, 72-73, 77, 79, 81, 87, 96, 100, 103, 105-106, 125, 127, 132, 134 and 145, an hNGAL mutein of the disclosure may include the wild type (natural) amino acid sequence outside the mutated amino acid sequence positions.

In further particular embodiments, a mutein according to the current disclosure comprises an amino acid sequence selected from the group consisting of SEQ ID NOs: 38-53 or a fragment or variant thereof.

The amino acid sequence of a Pvd-type-III-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 38-53.

The disclosure also includes structural homologues of an hNGAL mutein having an amino acid sequence selected from the group consisting of SEQ ID NOs: 38-53, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said hNGAL mutein.

A Pvd-type-III-binding hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to Pvd type I, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

Applications of Muteins Specific for Pyoverdine

Pyoverdines are the main siderophores of pseudomonads such as *P. aeruginosa*. In vitro experiments indicated a potential role of the *P. aeruginosa* pyoverdine in iron release from ferritransferrin but the ability of pyoverdine to compete for iron in vivo has only recently been demonstrated (Meyer et al., 1996, Infection and Immunity, 64, p. 518-523). It was observed using a burned-mouse model that the absence of pyoverdine production in mutants raised from a virulent parental strain correlated with a loss of virulence of these mutants and that virulence was restored when the homologous pyoverdine originating from the wild-type strain was supplemented. Furthermore, supplementation with a heterologous pyoverdine did not restore the virulence of the latter mutants. Thus, a precise knowledge of the pyoverdine-mediated iron uptake system used by a given *P. aeruginosa* isolate during infection appears a prerequisite for developing new ways of treatment of *P. aeruginosa* infections via bacterial iron metabolism, e.g., by blocking the pyoverdine biosynthesis or the pyoverdine-mediated iron transport.

Numerous possible applications for the pyoverdine-binding muteins of the disclosure, therefore, exist in medicine. In one further aspect, the disclosure relates to the use of a pyoverdine-binding mutein disclosed herein for detecting pyoverdine (type I, II or III) in a sample as well as a respective method of diagnosis.

The present disclosure also involves the use of one or more pyoverdine-binding muteins as described for complex formation with pyoverdine (type I, II or III).

Therefore, in another aspect of the disclosure, the disclosed muteins are used for the detection of pyoverdine (type I, II or III). Such use may include the steps of contacting one or more said muteins, under suitable conditions, with a sample suspected of containing pyoverdine, thereby allowing formation of a complex between the muteins and pyoverdine (type I, II or III), and detecting the complex by a suitable signal.

The detectable signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

The pyoverdine-binding muteins disclosed herein may also be used for the separation of pyoverdine (type I, II or III). Such use may include the steps of contacting one or more said muteins, under suitable conditions, with a sample supposed to contain pyoverdine (type I, II and/or III), thereby allowing formation of a complex between the muteins and pyoverdine (type I, II or III), and separating the complex from the sample.

In the use of the disclosed muteins for the detection of pyoverdine as well as the separation of pyoverdine (type I, II or III), the muteins and/or pyoverdine or a domain or fragment thereof may be immobilized on a suitable solid phase.

In still another aspect, the present disclosure features a diagnostic or analytical kit comprising a pyoverdine-binding mutein according to the disclosure.

In addition to their use in diagnostics, in yet another aspect, the disclosure encompasses the use of a pyoverdine-binding mutein of the disclosure or a composition comprising such mutein for the binding of pyoverdine (type I, II or III) in a subject and/or inhibiting or lessening growth of *P. aeruginosa* in a subject.

In still another aspect, the present disclosure features a method of binding pyoverdine (type I, II or III) in a subject, comprising administering to said subject an effective amount of one or more pyoverdine-binding muteins of the disclosure or of one or more compositions comprising such muteins.

In still another aspect, the present disclosure involves a method for inhibiting or lessening growth of *P. aeruginosa* in a subject, comprising administering to said subject an effective amount of one or more pyoverdine-binding muteins of the disclosure or of one or more compositions comprising such muteins.

Muteins Specific for Pyochelin

In addition, the present disclosure fulfills the need for alternative inhibitors of pyochelin by providing hNGAL muteins that bind pyochelin and useful applications therefor. Accordingly, the disclosure also provides methods of making and using the pyochelin-binding muteins described herein as well as compositions that may be used in methods of detecting pyochelin in a sample or in methods of binding of pyochelin in a subject. No such hNGAL muteins having these features attendant to the uses provided by present disclosure have been previously described.

Exemplary Muteins Specific for Pyochelin

In one aspect, the present disclosure relates to an hNGAL mutein that binds pyochelin complexed with iron with a $K_D$ of about 20 nM or lower, such as 1 nM or lower, for example, when measured by Biacore T200 instrument in an assay essentially described in Example 6.

In some still further embodiments, one or more hNGAL muteins of this disclosure are capable of binding pyochelin with complexed iron, with an affinity measured by an IC50 value of about 500 nM or lower, for example, when measured in an ELISA assay essentially described in Example 5.

In some still further embodiments, one or more hNGAL muteins of this disclosure are capable of binding pyochelin without complexed iron, with an affinity measured by an IC50 value of about 200 nM or lower, for example, when measured in an ELISA assay essentially described in Example 5.

In some still further embodiments, one or more hNGAL muteins of this disclosure are capable of binding pyochelin with and without complexed iron, with an affinity measured by an IC50 value of about 200 nM or lower, for example, when measured in an ELISA assay essentially described in Example 5.

In some embodiments, the mutein is capable of inhibiting iron uptake mediated by pyochelin with an IC50 value of about 150 nM or lower in a competition ELISA format essentially described in Example 7.

In some embodiments, the mutein is capable of inhibiting bacterial growth of Pvd I knock-out (ΔpvdA) in an assay essentially described in Example 8.

In this regard, the disclosure relates to a polypeptide, wherein said polypeptide includes an hNGAL mutein, and said hNGAL in comparison with the linear polypeptide sequence of the mature hNGAL, comprises at least 1, 2, 3, 4, 5, 6, 7, 8, 9, 10, 11, 12, 13, 14, 15, 16, 17, 18, 19, 20, 21, or even more, mutated amino acid residues at the sequence positions 28, 34, 36, 40-41, 44-46, 49, 52, 54, 65, 68, 70, 72-74, 77, 79-81, 87, 96, 100, 103, 106, 108, 123, 125, 127, 132, 134 and 141, and wherein said polypeptide binds pyochelin.

In some embodiments, a pyochelin-binding hNGAL mutein of the disclosure includes, at any one or more of the sequence positions 36, 40-41, 49, 52, 68, 70, 72-73, 77, 79, 81, 87, 96, 100, 103, 106, 125, 127, 132 and 134 of the linear polypeptide sequence of the mature hNGAL (SEQ ID NO: 1), one or more of the following mutated amino acid residues: Leu 36→His, Met or Val; Ala 40→Ile, Gln, Tyr or Phe; Ile 41→Leu, His or Trp; Gln 49→His, Arg, Ser or Ala; Tyr 52→Leu, Trp or Pro; Ser 68→Asp or His; Leu 70→Arg or Trp; Arg 72→His, Ile, Ala, Ser or Gly; Lys 73→Asn, Met, Pro, Phe, Gln or Arg; Asp 77→Arg, Thr, Pro or Asp; Trp 79→Ala, Arg, Lys or Asp; Arg 81→Thr, Ile or Trp; Asn 96→Met, Asn, Pro or Ala; Tyr 100→Gly, His or Glu; Leu 103→Gly, Met, His or Gln; Tyr 106→Met, Gly, Arg or Trp; Lys 125→Trp, Phe, Gly or Leu; Ser 127→Arg, Trp, Asp or Ile; Tyr 132→Ala, Glu or Thr; and Lys 134→Leu, Val, Asn or Phe. In some embodiments, an hNGAL mutein of the disclosure includes two or more, such as 3, 4, 5, 6, 7, 8, 9, 10, 11, 12, or even more or all mutated amino acid residues at these sequence positions of the mature hNGAL.

Additionally, a pyochelin-binding hNGAL mutein according to the disclosure may also comprise the following substitution in comparison with the linear polypeptide sequence of the mature hNGAL: Gln 28→His; Val 34→Leu; Glu 44→Gly; Asp 45→Gly; Lys→Arg or Tyr; Asn 65→Asp; Ile 80→Thr; Cys 87→Ser; Leu 94→Phe; Val 108→Ala; Phe 123→Ser and Thr 141 Ala.

In some additional embodiments, an hNGAL mutein of the disclosure, which binds to pyochelin, includes the following amino acid replacements in comparison with the linear polypeptide sequence of the mature hNGAL:

Gln 28→His; Ala 40→Ile; Ile 41→Leu; Gln 49→His; Tyr 52→Leu; Ser 68→His; Leu 70→Thr; Arg 72→Lys; Lys 73→Trp; Asp 77→Ile; Trp 79→Ser; Arg 81→His; Cys 87→Ser; Asn 96→Met; Tyr 100→Asn; Leu 103→His; Tyr 106→Met; Lys 125→Trp; Ser 127→Asp; Tyr 132→Glu; Lys 134→Leu;

Gln 28→His; Leu 36→His; Ala 40→Gln; Ile 41→Trp; Gln 49→Arg; Tyr 52→Trp; Ser 68→Asp; Leu 70→Asp; Arg 72→Ala; Lys 73→Ile; Asp 77→His; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe;

Gln 28→His; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Arg 81→Ile; Cys 87→Ser; Asn 96→Ala; Tyr 100→Gly; Leu 103→Met; Tyr 106→Trp; Lys 125→Gly; Ser 127→Trp; Tyr 132→Thru; Lys 134→Val;

Gln 28→His; Leu 36→Val; Ala 40→Tyr; Ile 41→Trp; Gln 49→Ala; Ser 68→Asp; Leu 70→Arg; Arg 72→Trp; Lys 73→Arg; Asp 77→Arg; Trp 79→Asp; Arg 81→Trp; Cys 87→Ser; Asn 96→Pro; Tyr 100→Glu; Leu 103→Gln; Tyr 106→Arg; Lys 125→Leu; Ser 127→Arg; Tyr 132→Ala; Lys 134→Asn; Gln 28→His; Vla 34 Leu; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Ile 80→Thr; Arg 81→Ile; Cys 87→Ser; Asn 96→Ala; Tyr 100→Gly; Leu 103→Met; Tyr 106→Trp; Phe 123→Ser; Lys 125→Gly; Ser 127→Trp; Tyr 132→Thru; Lys 134→Val; Thr 141→Ala;

Gln 28→His; Leu 36→Met; Ala 40→Phe; Ile 41→His; Gln 49→Ser; Tyr 52→Pro; Ser 68 His; Leu 70→Pro; Arg 72→Trp; Lys 73→Ala; Asp 77→Ala; Trp 79→Lys; Ile 80→Thr; Arg 81→Ile; Cys 87→Ser; Asn 96→Ala; Tyr 100→Gly; Leu 103→Met; Tyr 106→Trp; Phe 123→Ser; Lys 125→Gly; Ser 127→Trp; Tyr 132→Thru; Lys 134→Val;

Gln 28→His; Leu 36→His; Ala 40→Gln; Ile 41→Trp; Asp 45→Gly; Lys 46→Arg; Gln 49→Arg; Tyr 52→Trp; Ser 68→Asp; Leu 70→Asp; Arg 72→Ala; Lys 73→Ile; Asp 77→Leu; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe;

Gln 28→His; Leu 36→His; Ala 40→Gln; Ile 41→Trp; Glu 44→Gly; Lys 46→Tyr; Gln 49→Arg; Tyr 52→Trp; Ser 68→Asp; Leu 70→Asp; Arg 72→Ala; Lys 73→Ile; Lys 74→Glu; Asp 77→His; Trp 79→Arg; Arg 81→Thr; Cys 87→Ser; Leu 94→Phe; Tyr 100→His; Leu 103→Gly; Tyr 106→Gly; Val 108→Ala; Lys 125→Phe; Ser 127→Ile; Tyr 132→Ala; Lys 134→Phe; or

Leu 36→His; Ala 40→Gln; Ile 41→Trp; Asp 45→Gly; Lys 46→Arg; Gln 49→Arg; Tyr 52→Trp; Asn 65→Asp; Ser 68→Asp; Leu 70→Asp; Arg 72→Ala; Lys 73→Ile; Asp 77→Leu; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe.

In the residual region, i.e. the region differing from sequence positions 28, 34, 36, 40-41, 44-46, 49, 52, 54, 65, 68, 70, 72-74, 77, 79-81, 87, 96, 100, 103, 106, 108, 123, 125, 127, 132, 134 and 141, an hNGAL mutein of the disclosure may include the wild type (natural) amino acid sequence outside the mutated amino acid sequence positions.

In further particular embodiments, a mutein according to the current disclosure comprises an amino acid sequence selected from the group consisting of SEQ ID NOs: 54-63 or a fragment or variant thereof.

The amino acid sequence of a pyochelin-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 54-63.

The disclosure also includes structural homologues of an hNGAL mutein having an amino acid sequence selected from the group consisting of SEQ ID NOs: 54-63, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said hNGAL mutein.

A pyochelin-binding hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the mutein retains its capability to bind to Pvd type I, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

2. Applications of Muteins Specific for Pyochelin

Pyochelin (Pch) is one of the two major siderophores produced and secreted by *Pseudomonas aeruginosa* to assimilate iron. It chelates iron in the extracellular medium and transports it into the cell via a specific outer membrane transporter, FptA. Pch strongly chelates divalent metals such as Zn(II) (pZn=11.8 at p[H] 7.4) and Cu(II) (pCu=14.9 at p[H] 7.4) and forms predominantly 1:2 ($M^{2+}$/Pch) complexes. Siderophores are not only devoted to iron(III) shuttling but most likely display other specific biological roles in the subtle metals homeostasis in microorganisms.

Numerous possible applications for the muteins with binding-affinity for pyochelin of the disclosure, therefore, exist in medicine. In one further aspect, the disclosure relates to the use of such a mutein disclosed herein for detecting pyochelin in a sample as well as a respective method of diagnosis.

The present disclosure also involves the use of one or more muteins with binding-affinity for pyochelin as described for complex formation with pyochelin.

Therefore, in another aspect of the disclosure, the disclosed muteins are used for the detection of pyochelin. Such use may include the steps of contacting one or more said muteins, under suitable conditions, with a sample suspected of containing pyochelin, thereby allowing formation of a complex between the muteins and pyochelin, and detecting the complex by a suitable signal.

The detectable signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

The muteins disclosed herein may also be used for the separation of pyochelin. Such use may include the steps of contacting one or more said muteins, under suitable conditions, with a sample supposed to contain pyochelin, thereby allowing formation of a complex between the muteins and pyochelin, and separating the complex from the sample.

In the use of the disclosed muteins for the detection of pyochelin as well as the separation of pyochelin, the muteins and/or pyochelin or a domain or fragment thereof may be immobilized on a suitable solid phase.

Accordingly, the presence or absence of a molecule such as pyochelin, e.g., in a sample, as well as its concentration or level may be determined.

In still another aspect, the present disclosure features a diagnostic or analytical kit comprising a mutein with binding-affinity for pyochelin according to the disclosure.

In addition to their use in diagnostics, in yet another aspect, the disclosure encompasses the use of such a mutein of the disclosure or a composition comprising such mutein for the binding of pyochelin in a subject and/or inhibiting or lessening growth of *P. aeruginosa* in a subject.

In still another aspect, the present disclosure features a method of binding pyochelin in a subject, comprising administering to said subject an effective amount of one or more muteins with binding-affinity for pyochelin of the disclosure or of one or more compositions comprising such a mutein.

In still another aspect, the present disclosure involves a method for inhibiting or lessening growth of *P. aeruginosa* in a subject, comprising administering to said subject an effective amount of one or more muteins with binding-affinity for pyochelin of the disclosure or of one or more compositions comprising such a mutein.

C. Compositions Comprising Pyoverdine-Binding Mutein and/or Pyochelin-Binding Mutein and Combination of the Muteins

*P. aeruginosa* is a species of bacterium that is widely distributed in the environment and is capable of causing very severe infections in patients with predisposing conditions, such as cystic fibrosis. *P. aeruginosa* synthesizes two major siderophores, pyoverdine (Pvd) and pyochelin (Pch), to cover its needs in iron(III). The biofilm mode of growth is believed to be critical for persistent *P. aeruginosa* infections (Costerton et al., 1999; Singh et al., 2000) and the dual expression of Pvd and Pch genes is necessary for normal biofilm development (Banin et al., 2005).

Given that *P. aeruginosa* produces an impressive array of virulence factors, all playing a role in its pathogenicity, a preferred strategy to efficiently inhibit *P. aeruginosa* virulence is to target several virulence factors.

To this aim, the present disclosure encompasses use of (i) a first mutein or polypeptide thereof specific for pyoverdine type I, (ii) a second mutein or polypeptide thereof specific for pyoverdine type II, (iii) a third mutein or polypeptide thereof specific for pyoverdine type III and/or (iv) a fourth mutein or polypeptide thereof specific for pyochelin for the binding of pyoverdine type I, II, III and/or pyochelin in a subject. Such use includes a step of administering to a subject an effective amount of (i) a first mutein or polypeptide thereof specific for pyoverdine type I, (ii) a second mutein or polypeptide thereof specific for pyoverdine type II, (iii) a third mutein or polypeptide thereof specific for pyoverdine type III and/or (iv) a fourth mutein or polypeptide thereof specific for pyochelin. The present disclosure also contemplates the use of (i) a first mutein or polypeptide thereof specific for pyoverdine type I, (ii) a second mutein or polypeptide thereof specific for pyoverdine type II, (iii) a third mutein or polypeptide thereof specific for pyoverdine type III and/or (iv) a fourth mutein or polypeptide thereof specific for pyochelin for preventing or reducing iron-uptake by P. aeruginosa through pyochelin and/or pyoverdine in a subject. Similarly, the present disclosure discloses the use of (i) a first mutein or polypeptide thereof specific for pyoverdine type I, (ii) a second mutein or polypeptide thereof specific for pyoverdine type II, (iii) a third mutein or polypeptide thereof specific for pyoverdine type III and/or (iv) a fourth mutein or polypeptide thereof specific for pyochelin for the treatment or alleviation of P. aeruginosa infection and/or biofilm formation in a subject. In some further embodiments, the P. aeruginosa infection can be acute or chronic infections.

The first, second, third and/or fourth muteins or polypeptides thereof may be administered in combination, including concurrently, concomittantly or in series. In some embodiments, the first, second, third and/or fourth muteins or polypeptides thereof may be included in a composition that may be administered. The composition may include an effective amount of the first, second, third and/or fourth muteins or polypeptides thereof as active ingredients, in association with at least one pharmaceutically acceptable adjuvant, diluent or carrier. The first, second, third and/or fourth muteins or polypeptides thereof may also be administered independent from each other, including at individual intervals at independent points of time.

In some embodiments, the mutein specific for pyoverdine (type I, II or III) as used in the disclosure is able to bind pyoverdine (type I, II or III, respectively) with detectable affinity, i.e. with a dissociation constant of at least 200 nM, including about 100 nM, about 50 nM, about 25 nM or about 15 nM. In some embodiments, the mutein specific for pyochelin as used in the disclosure is able to bind pyochelin with detectable affinity, i.e. with a dissociation constant of at least 200 nM including about 100 nM, about 50 nM, about 25 nM or about 15 nM. In some further preferred embodiments, a mutein of the combination according to the disclosure binds pyoverdine (type I, II or III) or pyochelin, respectively, with a dissociation constant for pyoverdine (type I, II or III, respectively) or pyochelin of at least about 10 nM, about 1 nM, about 0.1 nM, about 10 μM, or even lower. The present disclosure, thus, provides a combination of (i) a mutein of hNGAL that has a detectable affinity to pyoverdine type I (Pvd I s, sa, αKG+/−Fe), (ii) a mutein of hNGAL that has a detectable affinity to pyoverdine type II (Pvd II s, sa, αKG+/−Fe), (iii) a mutein of hNGAL that has a detectable affinity to pyoverdine type III (Pvd III s, sa, αKG+/−Fe) and/or (iv) a mutein of hNGAL that has a detectable affinity to pyochelin (Pch+/−Fe).

Further details on hNGAL muteins with a detectable affinity for pyoverdine can be found in Section A of the current disclosure.

In a particularly preferred embodiment, a mutein that is specific for pyoverdine type I is shown in any one of SEQ ID NOs: 2-18. In a particularly preferred embodiment, a mutein that is specific for pyoverdine type II is shown in any one of SEQ ID NOs: 19-37. In a particularly preferred embodiment, a mutein that is specific for pyoverdine type III is shown in any one of SEQ ID NOs: 38-53.

Further details of hNGAL muteins with a detectable affinity for pyochelin have been disclosed in Section B of the current disclosure.

In a particular preferred embodiment, the mutein that is specific for pyochelin is shown in any one of SEQ ID NOs: 54-63.

The present disclosure also relates to a composition comprising at least one of the following: (i) a first mutein or polypeptide thereof specific for pyoverdine type I, (ii) a second mutein or polypeptide thereof specific for pyoverdine type II, (iii) a third mutein or polypeptide thereof specific for pyoverdine type III and (iv) a fourth mutein or polypeptide thereof specific for pyochelin, which composition can be used in a method of binding of pyoverdine type I, II, III and/or pyochelin.

The present disclosure relates to a combination of a first mutein or polypeptide or composition thereof, a second mutein or polypeptide or composition thereof, a third mutein or polypeptide or composition thereof, and/or a fourth mutein or polypeptide or composition thereof. One of these muteins can bind to pyoverdine (type I, II or III) as a given non-natural target with detectable affinity. One of these muteins can bind to pyochelin as a given non-natural target with detectable affinity. The respective mutein thus binds to pyoverdine type I, II, III or pyochelin, respectively, as a given non-natural target. The term "non-natural target" refers to a compound, which does not bind to the corresponding lipocalin (the wild-type hNGAL) under physiological conditions. For example, the first mutein or polypeptide or composition thereof can bind to one type of pyoverdine (type I, II or III) or pyochelin and the second, the third or the fourth mutein or polypeptide or composition thereof can bind to pyochelin or an another type of pyoverdine respectively, or vice versa. The combination of the first, the second, the third and/or the fourth muteins or polypeptides or compositions thereof may be provided in various forms and orientations.

In still another aspect, the present disclosure features a method of binding pyoverdine type I, II, III and/or pyochelin in a subject comprising administering to said subject an effective amount of a composition that comprises at least one of the following: (i) a mutein or polypeptide thereof specific for pyoverdine type I, (ii) a mutein or polypeptide thereof specific for pyoverdine type II, (iii) a mutein or polypeptide thereof specific for pyoverdine type III and (iv) a mutein or polypeptide thereof specific for pyochelin. In some embodiments, such composition comprises two or more of, e.g. three or even all of (i)-(iv).

In still another aspect, the present disclosure involves a method for inhibiting or lessening growth of P. aeruginosa in a subject comprising administering to said subject an effective amount of a composition that comprises at least one of the following: (i) a mutein or polypeptide thereof specific for pyoverdine type I, (ii) a mutein or polypeptide thereof specific for pyoverdine type II, (iii) a mutein or polypeptide thereof specific for pyoverdine type III and (iv) a mutein or polypeptide thereof specific for pyochelin. In some embodiments, such composition comprises two or more of, e.g. three or even all of (i)-(iv).

The present disclosure also involves the use of (i) a first mutein or polypeptide thereof specific for pyoverdine type I, (ii) a second mutein or polypeptide thereof specific for pyoverdine type II, (iii) a third mutein or polypeptide thereof specific for pyoverdine type III, and/or (iv) a fourth mutein or polypeptide thereof specific for pyochelin, for complex formation with pyoverdine type I, II, III and/or pyochelin.

Therefore, in another aspect of the disclosure, the disclosed muteins or polypeptides can be used for the detection of pyoverdine and pyochelin. Such use may include the steps of contacting one or more said muteins or polypeptides, under suitable conditions, with a sample suspected of containing pyoverdine and/or pyochelin, thereby allowing formation of a complex between the muteins or polypeptides and pyoverdine and/or between the muteins and pyochelin, respectively, and detecting the complex by a suitable signal.

The detectable signal can be caused by a label, as explained above, or by a change of physical properties due to the binding, i.e. the complex formation, itself. One example is surface plasmon resonance, the value of which Is changed during binding of binding partners from which one is immobilized on a surface such as a gold foil.

The muteins or polypeptides disclosed herein may also be used for the separation of pyoverdine and/or pyochelin. Such use may include the steps of contacting one or more said muteins, under suitable conditions, with a sample supposed to contain pyoverdine and/or pyochelin, thereby allowing formation of a complex between the muteins and pyoverdine and/or between the muteins and pyochelin, respectively, and separating the complex from the sample.

In the use of the disclosed muteins or polypeptides for the detection of pyoverdine and/or pyochelin as well as the separation of pyoverdine and/or pyochelin, the muteins and/or pyoverdine and pyochelin or a domain or fragment thereof may be immobilized on a suitable solid phase.

Accordingly, the presence or absence of pyoverdine and/or pyochelin, e.g., in a sample, as well as its concentration or level may be determined.

In another aspect, the disclosure provides for a kit of parts. The kit includes, in one or more containers, separately or in a mixture, a mutein or polypeptide specific for pyoverdine type I or composition thereof, a mutein or polypeptide specific for pyoverdine type II or composition thereof, a mutein or polypeptide specific for pyoverdine type III or composition thereof, and/or a mutein or polypeptide specific for pyochelin or composition thereof. In some further preferred embodiments, the kit comprises a first container that includes a first mutein or polypeptide specific for pyoverdine type I or composition thereof, a second container that includes a second mutein or polypeptide specific for pyoverdine type II or composition thereof, a third container that includes a third mutein or polypeptide specific for pyoverdine type III or composition thereof, and/or a fourth container that includes a fourth mutein or polypeptide specific for pyochelin or composition thereof. In some embodiments the kit further includes integrally thereto or as one or more separate documents, information pertaining to the contents or the kit and the use of the muteins or polypeptides thereof. The kit may include in some embodiments one or more compositions that are formulated for reconstitution in a diluent. Such a diluent, e.g. a sterile diluent, may also be included in the kit, for example within a container.

D. Muteins of the Disclosure

When used herein in the context of the muteins of the present disclosure that bind to pyoverdine or pyochelin, the term "specific for" includes that the mutein is directed against, binds to, or reacts with pyoverdine or pyochelin, respectively. Thus, being directed to, binding to or reacting with includes that the mutein specifically binds to pyoverdine or pyochelin, respectively. The term "specifically" in this context means that the mutein reacts with a pyoverdine protein or a pyochelin protein, as described herein, but essentially not with another protein. The term "another protein" includes any non-pyoverdine or non-pyochelin protein, respectively, including proteins closely related to or being homologous to pyoverdine or pyochelin against which the muteins disclosed herein are directed to. However, pyoverdine or pyochelin proteins, fragments and/or variants from species other than human such as those described in the context of the definition "subject" are not excluded by the term "another protein". The term "does not essentially bind" means that the mutein of the present disclosure does not bind another protein, i.e., shows a cross-reactivity of less than 30%, preferably 20%, more preferably 10%, particularly preferably less than 9, 8, 7, 6 or 5%. Whether the mutein specifically reacts as defined herein above can easily be tested, inter alia, by comparing the reaction of a lipocalin mutein of the present disclosure with pyoverdine or pyochelin and the reaction of said mutein with (an) other protein(s). "Specific binding" can also be determined, for example, in accordance with Western blots, ELISA-, RIA-, ECL-, IRMA-tests, FACS, IHC and peptide scans.

The amino acid sequence of a mutein according to the disclosure has a high sequence identity to human lipocalin 2 when compared to sequence identities with another lipocalin (see also above). In this general context the amino acid sequence of a mutein of the combination according to the disclosure is at least substantially similar to the amino acid sequence of the corresponding lipocalin (the wild-type hNGAL). A respective sequence of a mutein of the combination according to the disclosure, being substantially similar to the sequence of mature hNGAL, such as at at least 65%, at least 70%, at least 75%, at least 80%, at least 82%, at least 85%, at least 87%, at least 90% identity, including at least 95% identity to the sequence of mature hNGAL. In this regard, a mutein of the disclosure of course may contain, in comparison substitutions as described herein which renders the mutein capable of binding to pyoverdine type I, II, III or pyochelin, respectively. Typically a mutein of hNGAL includes one or more mutations—relative to the native sequence of hNGAL—of amino acids in the four loops at the open end of the ligand binding site of hNGAL. As explained above, these regions are essential in determining the binding specificity of a mutein for pyoverdine type I, II, III or pyochelin. A mutein derived hNGAL or a homologue thereof, may have one, two, three, four or more mutated amino acid residues at any sequence position in the N-terminal region and/or in the three peptide loops BC, DE, and FG arranged at the end of the β-barrel structure that is located opposite to the natural binding pocket.

A mutein according to the disclosure includes one or more, such as two, three, four, five, six, seven, eight, nine, ten, eleven, twelve, thirteen, fourteen, fifteen, sixteen, seventeen, eighteen, nineteen or even twenty substitutions in comparison to the corresponding native hNGAL alin, provided that such a mutein should be capable of binding to pyoverdine or pyochelin, respectively. For example, a mutein can have a substitution at a position corresponding to a distinct position (i.e. at a corresponding position) of hNGAL. In some embodiments a mutein of the combination according to the disclosure includes at least two amino acid substitutions, including 2, 3, 4, 5, ors even more, amino acid substitutions of a native amino acid by an arginine residue. Accordingly, the nucleic acid of a protein 'reference' scaffold as described herein is subject to mutagenesis with the aim of generating a mutein which is capable of binding to pyoverdine type I, II, III or pyochelin, respectively.

Also, a mutein of the present disclosure can comprise a heterologous amino acid sequence at its N- or C-Terminus, preferably C-terminus, such as a Strep-tag, e.g., Strep II tag without affecting the biological activity (binding to its target e.g. pyoverdine or pyochelin, respectively) of the mutein.

Specifically, in order to determine whether an amino acid residue of the amino acid sequence of a mutein different from wild-type hNGAL corresponds to a certain position in the amino acid sequence of wild-type hNGAL, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, wild-type hNGAL can serve as "subject sequence" or "reference sequence", while the amino acid sequence of a mutein different from the wild-type hNGAL described herein serves as "query sequence". The terms "reference sequence" and "wild type sequence" are used interchangeably herein.

In some embodiments a substitution (or replacement) is a conservative substitution. Nevertheless, any substitution—including non-conservative substitution or one or more from the exemplary substitutions listed below—is envisaged as long as the mutein retains its capability to bind to pyoverdine type I, II, III or pyochelin, respectively, and/or it has an identity to the then substituted sequence in that it is at least 60%, such as at least 65%, at least 70%, at least 75%, at least 80%, at least 85% or higher identical to the "original" sequence.

Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:

Alanine (Ala), Glycine (Gly);
Aspartic acid (Asp), Glutamic acid (Glu);
Asparagine (Asn), Glutamine (Gln);
Arginine (Arg), Lysine (Lys);
Isoleucine (Ile), Leucine (Leu), Methionine (Met), Valine (Val);
Phenylalanine (Phe), Tyrosine (Tyr), Tryptophan (Trp);
Serine (Ser), Threonine (Thr); and
Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

Substantial modifications in the biological properties of hNGAL are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, methionine, alanine, valine, leucine, iso-leucine; (2) neutral hydrophilic: cysteine, serine, threonine; (3) acidic: aspartic acid, glutamic acid; (4) basic: asparagine, glutamine, histidine, lysine, arginine; (5) residues that influence chain orientation: glycine, proline; and (6) aromatic: tryptophan, tyrosine, phenylalanine.

Non-conservative substitutions will entail exchanging a member of one of these classes for another class. Any cysteine residue not involved in maintaining the proper conformation of hNGAL also may be substituted, generally with serine, to improve the oxidative stability of the molecule and prevent aberrant crosslinking. Conversely, cysteine bond (s) may be added to improve its stability.

Any mutation, including an insertion as discussed above, can be accomplished very easily on the nucleic acid, e.g. DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of hNGAL as long as these deletions or insertion result in a stable folded/functional mutein.

Modifications of the amino acid sequence include directed mutagenesis of single amino acid positions in order to simplify sub-cloning of the mutated hNGAL gene or its parts by incorporating cleavage sites for certain restriction enzymes. In addition, these mutations can also be incorporated to further improve the affinity of a mutein for a given target such as pyoverdine or pyochelin. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. The generated thiol moiety may be used to PEGylate or HESylate the mutein, for example, in order to increase the serum half-life of a respective mutein.

It is also possible to mutate other amino acid sequence positions to cysteine in order to introduce new reactive groups, for example, for the conjugation to other compounds, such as polyethylene glycol (PEG), hydroxyethyl starch (HES), biotin, peptides or proteins, or for the formation of non-naturally occurring disulphide linkages.

In some embodiments, if one of the above moieties is conjugated to a mutein of the disclosure, conjugation to an amino acid side chain can be advantageous. Suitable amino acid side chains may occur naturally in the amino acid sequence of hNGAL or may be introduced by mutagenesis. In case a suitable binding site is introduced via mutagenesis, one possibility is the replacement of an amino acid at the appropriate position by a cysteine residue.

With respect to a mutein of human lipocalin 2, exemplary possibilities of such a mutation to introduce a cysteine residue into the amino acid sequence of a lipocalin including human lipocalin 2 mutein to include the introduction of a cysteine (Cys) residue at at least at one of the sequence positions that correspond to sequence positions 14, 21, 60, 84, 88, 116, 141, 145, 143, 146 or 158 of the wild type sequence of human NGAL. In some embodiments where a human lipocalin 2 mutein of the disclosure has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human lipocalin 2 mutein.

In another embodiment, in order to provide suitable amino acid side chains for conjugating one of the above compounds to a mutein according to the present disclosure, artificial amino acids may be introduced by mutagenesis. Generally, such artificial amino acids are designed to be more reactive and thus to facilitate the conjugation to the desired compound. One example of such an artificial amino acid that may be introduced via an artificial tRNA is para-acetyl-phenylalanine.

For several applications of the muteins disclosed herein it may be advantageous to use them in the form of fusion proteins. In some embodiments, a mutein of the disclosure is fused at its N-terminus or its C-terminus to a protein, a protein domain or a peptide, for instance, a signal sequence and/or an affinity tag.

Affinity tags such as the Strep-Tag® or Strep-Tag® II (Schmidt, T. G. M. et al. (1996) J. Mol. Biol. 255, 753-766), the myc-tag, the FLAG-tag, the His$_6$-tag or the HA-tag or proteins such as glutathione-S-transferase also allow easy detection and/or purification of recombinant proteins are further examples of suitable fusion partners. Finally, proteins with chromogenic or fluorescent properties such as the green fluorescent protein (GFP) or the yellow fluorescent protein (YFP) are suitable fusion partners for muteins of the disclosure as well.

In general, it is possible to label the muteins of the disclosure with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horse-radish peroxidase and 1-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the disclosure. The muteins of the disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The muteins of the disclosure may, however, also be conjugated with therapeutically active nucleic acids such as antisense nucleic acid molecules, small interfering RNAs, micro RNAs or ribozymes. Such conjugates can be produced by methods well known in the art.

As indicated above, a mutein of the disclosure may in some embodiments be conjugated to a moiety that extends the serum half-life of the mutein (in this regard see also PCT publication WO 2006/56464 where such conjugation strategies are described with references to muteins of human neutrophile gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, Pharmacol. Rev. 52, 1-9), an Fc part of an immunoglobulin, a CH3 domain of an immunoglobulin, a CH4 domain of an immunoglobulin, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a mutein with binding activity for albumin. Accordingly, suitable conjugation partners for extending the half-life of a mutein of the disclosure include an albumin binding protein, for example, a bacterial albumin binding domain, such as the one of streptococcal protein G (König, T., & Skerra, A. (1998) J. Immunol. Methods 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (SEQ ID NO: 131; Dennis, M. S., Zhang, M., Meng, Y. G., Kadkhodayan, M., Kirchhofer, D., Combs, D. & Damico, L. A. (2002) J Biol Chem 277, 35035-35043).

In other embodiments, albumin itself (Osbom, B. L. et al., 2002, J. Pharmacol. Exp. Ther. 303, 540-548), or a biological active fragment of albumin can be used as conjugation partner of a mutein of the disclosure. The term "albumin" includes all mammal albumins such as human serum albumin or bovine serum albumin or rat albumine. The albumin or fragment thereof can be recombinantly produced as described in U.S. Pat. No. 5,728,553 or European patent applications EP 0 330 451 and EP 0 361 991. Recombinant human albumin (Recombumin®) Novozymes Delta Ltd. (Nottingham, UK) can be conjugated or fused to a mutein of the disclosure in order to extend the half-life of the mutein.

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the disclosure, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the muteins of the disclosure, the SynFusion™ technology, commercially available from Syntonix Pharmaceuticals, Inc (MA. USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of the muteins of the disclosure is to fuse to the N- or C-terminus of the muteins long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins J. Control. Release 11, 139-148). The molecular weight of such a polymer, such as polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. No. 6,500,930 or 6,620,413, carbohydrate oligo- and polymers such as starch or hydroxyethyl starch (HES) can be conjugated to a mutein of the disclosure for the purpose of serum half-life extension.

In addition, a mutein disclosed herein may be fused to a moiety may confer new characteristics to the muteins of the disclosure such as enzymatic activity or binding affinity for other molecules. Examples of suitable fusion partners are alkaline phosphatase, horseradish peroxidase, gluthation-S-transferase, the albumin-binding domain of protein G, protein A, antibody fragments, oligomerization domains or toxins.

In particular, it may be possible to fuse a mutein disclosed herein with a separate enzyme active site such that both "components" of the resulting fusion protein together act on a given therapeutic target. The binding domain of the mutein attaches to the disease-causing target, allowing the enzyme domain to abolish the biological function of the target.

The present disclosure also relates to nucleic acid molecules (DNA and RNA) that include nucleotide sequences encoding the muteins of the disclosure. Since the degeneracy of the genetic code permits substitutions of certain codons by other codons specifying the same amino acid, the disclosure is not limited to a specific nucleic acid molecule encoding a mutein as described herein but encompasses all nucleic acid molecules that include nucleotide sequences encoding a functional mutein. In this regard, the present disclosure provides nucleotide sequences encoding some muteins of the disclosure as shown in SEQ ID NOs: 65-126.

In one embodiment of the disclosure, the method includes subjecting the nucleic acid molecule to mutagenesis at nucleotide triplets coding for at least one, or even more, of the sequence positions corresponding to the sequence positions 28, 34, 36, 39-42, 44-47, 49, 52, 54-55, 65, 68, 70, 72-75, 77, 79-81, 87, 96, 100, 103, 106, 108, 123, 125, 127, 132, 134, 141 and 145 of the linear polypeptide sequence of human NGAL (SEQ ID NO: 2).

The disclosure also includes nucleic acid molecules encoding the muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the muteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements Involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) Annu. Rev. Biophys. Biomol. Struct. 26, 401-424, or Rodi, D. J., and Makowski, L. (1999) Curr. Opin. Biotechnol. 10, 87-93).

Such cloning vehicles can include, aside from the regulatory sequences described above and a nucleic acid sequence encoding a mutein as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a mutein as described herein, and in particular a cloning vector containing the coding sequence of such a mutein can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a fusion protein of the disclosure. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g., HeLa cells or CHO cells) or primary mammalian cells.

The disclosure also relates to a method for the production of a mutein or a polypeptide thereof as described herein, wherein the mutein or polypeptide, a fragment of the mutein or polypeptide or a fusion protein of the mutein or polypeptide and another polypeptide is produced starting from the nucleic acid coding for the mutein or polypeptide by means of genetic engineering methods. The method can be carried out in vivo, the mutein or polypeptide can for example be produced in a bacterial or eukaryotic host organism and then isolated from this host organism or its culture. It is also possible to produce a protein in vitro, for example by use of an in vitro translation system.

When producing the mutein or polypeptide thereof in vivo a nucleic acid encoding such mutein or polypeptide is introduced into a suitable bacterial or eukaryotic host organism by means of recombinant DNA technology (as already outlined above). For this purpose, the host cell is first transformed with a cloning vector that includes a nucleic acid molecule encoding a mutein as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In some embodiments, a nucleic acid molecule, such as DNA, disclosed in this application may be "operably linked" to another nucleic acid molecule of the disclosure to allow expression of a fusion protein of the disclosure. In this regard, an operable linkage is a linkage in which the sequence elements of the first nucleic acid molecule and the sequence elements of the second nucleic acid molecule are connected in a way that enables expression of the fusion protein as a single polypeptide.

In addition, in some embodiments, the naturally occurring disulfide bond between Cys 76 and Cys 175 may be removed in hNGAL muteins of the disclosure. Accordingly, such muteins can be produced in a cell compartment having a reducing redox milieu, for example, in the cytoplasma of Gram-negative bacteria.

In case a mutein of the disclosure includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a mutein or polypeptide thereof of the disclosure in the cytosol of a host cell, preferably *E. coli*. In this case, the mutein or polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) J. Mol. Biol. 315, 1-8.).

However, the mutein or polypeptide as described herein may not necessarily be generated or produced only by use of genetic engineering. Rather, such mutein or polypeptide can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for pyoverdine type I, II, III or pyochelin. Methods for the solid phase and/or solution phase synthesis of proteins are well known in the art (see e.g. Bruckdorfer, T. et al. (2004) Curr. Pharm. Biotechnol. 5, 29-43).

In another embodiment, the mutein or polypeptide of the disclosure may be produced by in vitro transcription/translation employing well-established methods known to those skilled in the art.

The skilled worker will appreciate methods useful to prepare muteins or polypeptides thereof contemplated by the present disclosure but whose protein or nucleic acid sequences are not explicitly disclosed herein. As an overview, such modifications of the amino acid sequence include, e.g., directed mutagenesis of single amino acid positions in order to simplify sub-cloning of a mutated hNGAL gene or its parts by incorporating cleavage sites for certain restriction enzymes. In addition, these mutations can also be incorporated to further improve the affinity of a mutein for its target (e.g. pyoverdine or pyochelin, respectively). Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

The muteins or polypeptides thereof disclosed herein and their derivatives can be used in many fields similar to antibodies or fragments thereof. For example, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. In addition, muteins or polypeptides thereof of the disclosure can serve to detect chemical structures by means of established analytical methods (e.g., ELISA or Western Blot) or by microscopy or immunosensorics. In this regard, the detection signal can either be generated directly by use of a suitable mutein conjugate or fusion protein or indirectly by immunochemical detection of the bound mutein via an antibody.

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

V. EXAMPLES

Example 1: Purification and Biotinylation of Pseudomonas aeruginosa Siderophores P. aeruginosa produces three groups of pyoverdines i.e. pyoverdine type I, pyoverdine type II & pyoverdine type III. Each group has three forms differing in the side chain which is succinyl, succinamid or α-ketoglutaryl. In addition P. aeruginosa produces pyochelin. All ten siderophores can complex iron as $Fe^{3+}$.

For selection and screening of muteins of interest, the siderophores may be biotinylated. Biotinylation was performed for pyoverdine I succinyl variant at the succinyl side chain, for pyoverdine II succinyl variant at the L-omithine side chain and for pyoverdine III succinyl variant mainly at the glycine side chain. Pyochelin was biotinylated at the phenol ring.

Example 2: Selection of Muteins Specifically Binding to P. aeruginosa Siderophores hNGAL-based libraries, generated by random mutagenesis of mature hNGAL, were used for selection of muteins specifically binding to the different siderophores of P. aeruginosa. Biotinylated and iron loaded Pvd I succinyl, Pvd II succinyl, and Pvd III succinyl as well as biotinylated non-iron-loaded pyochelin were used in independent phage display and selection processes.

$2 \times 10^{12}$ phagemids from these libraries were incubated with 200 nM or 500 nM or 1 µM biotinylated target. Paramagnetic beads coated with neutravidin or streptavidin were used to capture target/phagemid complexes which were subsequently isolated with a magnet. Unbound phagemids were removed by washing the beads with PBST or PBS. Bound phagemids were first eluted with 300 µl 70 mM triethylamine for 10 min followed by immediate neutralization of the supernatant with 100 µl 1 M Tris-Cl pH 6.0. After one intermediate wash cycle remaining phagemids were eluted with 100 mM glycin pH2.2 for 10 min followed by immediate neutralization with 50 µl 0.5 M Tris-base. Both elution fractions were pooled and used to infect 4 ml of E. coli XL1-blue culture ($OD_{550}$ 0.45-0.6) for reamplification. After incubation for 30 min under agitation bacteria were collected by centrifugation at 5000×g for 2 min, resuspended in 1 ml 2×YT medium and plated on three big LB/Amp agar plates (10 g/l bacto tryptone, 5 g/l yeast extract, 5 g/l NaCl, pH 7.5, 15 g/l agar, 100 µg/ml ampicillin). Plates were incubated overnight at 32° C. Infected cells were scraped from the agar plates using 50 ml 2×YT medium supplemented with 100 µg/ml ampicillin (2×YT/Amp). 50 ml 2×YT/Amp medium were inoculated with the appropriate volume of bacterial suspension to reach an $OD_{550}$ of 0.08. The culture was incubated at 37° C. on a shaker (160 rpm) until an $OD_{550}$ of 0.5 was reached and then infected with helperphages ($1.5 \times 10^{11}$ pfu) by incubation for 15 min with gentle agitation and for 45 min on a shaker at 37° C. Subsequently, kanamycin was added to a final concentration of 70 µg/ml to select bacteria infected by helperphages. Finally, expression of the pIII-hNGAL muteins was induced by addition of 25 ng/ml anhydrotetracyclin.

After 15 h incubation at 24'C the supernatant of the culture was cleared by centrifugation (5000×g for 20 min). Subsequently, 20 ml supernatant were passed through a polyethersulfone membrane with a pore size of 0.22 µm. To the filtrate 5 ml of a solution containing 20% (w/v) PEG-8000 and 15% (w/v) NaCl in water was added and gently mixed. The solution was incubated for 30 min on ice before centrifugatuion for 20 min at 4° C. & 5000×g. The pellet containing the phagemids was dissolved in 1 ml buffer containing 200 mM boric acid, 160 mM NaCl and 1 mM EDTA. Unsoluble particles were removed by centrifugation (5000×g for 5 min). The supernatant was transferred to a fresh tube and mixed with 200 µl of a solution containing 20% (w/v) PEG-8000 and 15% (w/v) NaCl in water. The solution was incubated 30 min on ice and precipitated phagemids were subsequently collected by centrifugation (5000×g for 5 min). Phagemids were resuspended in PBS supplemented with 50 mM benzamidine and used for the next round of phagemid selection.

Four consecutive rounds of selection were performed. Different washing conditions were applied: i) eight times with 1 ml PBS/T 5 min incubation for each washing step in all 4 selection rounds, ii) the number of wash cycles increased from round 1 to 4 iii) fast washing steps were altered with 5 min incubation washing steps and the number of washings steps was increased from round to round.

Phagemid DNA was prepared from E. coli cells infected with the output of the fourth selection round and the hNGAL mutein cassette was isolated by digestion of the DNA with BstX1 and subsequent purification via agarose gel electrophoresis using standard methods (Sambrook et al., (1989) Molecular cloning: a laboratory manual). The hNGAL mutein cassette was inserted into the likewise cut vector, which allows bacterial production of the hNGAL muteins under the control of a tetracyclin promoter. $CaCl_2$-competent TG1-F' cells were transformed with the ligation mixture and plated on LB/Amp plates.

For optimization of Pvd I, Pvd II, Pvd III and Pch-specific muteins, additional libraries were generated based on mutein SEQ ID NO: 4, SEQ ID NO: 6, SEQ ID NO: 19, SEQ ID NO: 20, SEQ ID NO: 42, SEQ ID NO: 55, SEQ ID NO: 56 and subsequently SEQ ID NO: 8, SEQ ID NO: 12 and SEQ ID NO: 45. Libraries were generated using either a biased randomization of selected positions or error prone polymerase chain reaction (PCR) based methods. Selection of muteins was performed as described but with increased stringency.

In order to facilitate expression in eukaryotic cells, potential N-glycosylation sites (Asn-X-Ser/Thr) were removed.

Furthermore, mutations were introduced to further optimize for stability.

Example 3: Identification of Muteins Specifically Binding to the Respective P. aeruginosa Siderophores Using High-Throughput ELISA Screening Individual colonies were used to inoculate 2×YT/Amp medium and grown overnight (14-18 h) to stationary phase. Subsequently, 50 µl 2×YT/Amp were inoculated from the stationary phase cultures and incubated for 3 h at 37° C. and then shifted to 22° C. until an $OD_{595}$ of 0.6-0.8 was reached. Production of muteins was induced by addition of 10 µl 2×YT/Amp supplemented with 1.2 µg/ml anhydrotetracyclin. Cultures were incubated at 22° C. until the next day. After addition of 40 µl of 5% (w/v) BSA in PBS/T and incubation for 1 h at 25° C. cultures were ready for use in screening assays.

Specific binding of the isolated muteins to the respective siderophore targets was tested by coating a 1:1 mixture of neutravidin and streptavidin (5 µg/ml in PBS) overnight at 4° C. on microtiterplates. After blocking the plate 1 h with 2% BSA in PBST the respective biotinylated siderophore target used for selection was captured on the coated microtiterplates at a concentration of 1.5-2.5 µg/ml in PBS/T. Plates coated in the same manner with biotinylated-aldosterone were used as negative control target in the screening. Subsequently, 20 µl of BSA-blocked cultures were added to the coated microtiter plate containing either captured target or aldosterone and incubated for 1 h at 25° C. Bound muteins were detected after 1 h incubation with anti-T7 antibody conjugated with horseradish peroxidase (Merck KgaA, Darmstadt) or anti-Streptag antibody conjugated with horseradish peroxidase (IBA, Boettingen). For quantification, 20 µl of QuantaBlu fluorogenic peroxidase substrate was added and the fluorescence determined at an excitation wavelength of 320 nm and an emission wavelength of 430 nm. Muteins specifically binding to the respective siderophore targets were then sequenced.

To select for muteins with increased affinity and stability screening was performed with i) reduced antigen concentration and/or ii) competition with unbiotinylated target and/or iii) incubation of the screening supernatant at 65° C. or 70° C. before addition to the target plate and/or iv) using reverse screening formats were the muteins were captured via the Streptag on microtiter plates coated with anti-Streptag antibody and different concentrations of biotinylated target was added and detected via extravidin-HRP (Sigma Aldrich, St. Louis, Mo.).

Example 4: Expression of Muteins

Unique muteins were expressed with C-terminal sequence SAWSHPQFEK (SEQ ID NO: 127; including the SA linker and the Strep-Tag® II, WSHPQFEK (SEQ ID NO: 128) in E. coli in 2YT-Amp media to purify the muteins after expression using Streptactin affinity chromatography and preparative size exclusion chromatography were applicable.

Example 5: Affinity of Muteins to Soluble P. aeruginosa Siderophores Determined in an ELISA Based Setting Solution binding of muteins was assayed by a "Solution binding ELISA", the principle of which was as follows: a constant concentration of the tested mutein was incubated with variable concentrations of ligands (Pvd I s, sa, αKG+/−Fe/Pvd II s, sa, αKG+/−Fe/Pvd III s, sa, αKG+/−Fe/Pch+/−Fe) for 1 h. After this pre-incubation in solution, an aliquot of the mutein/ligand mixture was transferred to an ELISA plate with biotinalyted Pvd I s (+Fe), Pvd II s (+Fe), Pvd III s (+Fe) or Pch immobilized via Neutravidin to measure the remaining concentration of free muteins. The concentration of free (non ligand-bound) muteins was determined via a quantitative ELISA setup.

In detail, a 384-well plate suitable for fluorescence measurements (Greiner FLUOTRAC™ 600, black flat bottom, high-binding) was coated with 20 µl of Neutravidin at a concentration of 5 µg/ml in PBS over night at 4 C. After washing, the Neutravidin-coated wells were blocked with 100 µl blocking buffer containing 0.1% Tween 20 and 2% BSA (PBS-T/BSA) for 1 h at room temperature. After washing again, 20 µl biotinylated pyoverdine or pyochelin in blocking buffer at a concentration of 1 µg/mL were added for 1 h at room temperature and excess reagent was removed.

A fixed concentration of muteins was incubated in solution with varying concentrations of ligand (Pvd I s, sa, αKG+/−Fe/Pvd II s, sa, αKG+/−Fe/Pvd III s, sa, αKG+/−Fe/Pch+/−Fe), using a suitable starting concentration which was serially diluted at a 1:3 ratio down to the picomolar range in PBS-T/BSA. After 1 h incubation at room temperature, 20 µl of the reaction mixture was transferred to the 384-well plate upon which biotinylated pyoverdin or pyochelin was immobilized to capture unbound (free) muteins for 20 min at RT. To allow for transformation of ELISA readout results Into absolute free mutein concentrations, a standard curve containing varying concentrations of muteins was prepared in PBS-T/BSA and incubated for 20 min on the same ELISA plate as well.

The residual supernatants were discarded and 20 µl HRP-labeled anti-hNGAL antibody was added at a predetermined optimal concentration in PBS-T/BSA and incubated for 1 h at RT. The anti-hNGAL antibody had been obtained by immunization of rabbits with a mixture of muteins, and was subsequently coupled to HRP using a kit (EZ-link Plus Activated Peroxidase, Thermo Scientific) according to the manufacturer's instructions, to obtain the antibody-HRP conjugate. After washing, 20 µl fluorogenic HRP substrate (QuantaBlu, Thermo) was added to each well, and the reaction was allowed to proceed for 15 to 60 minutes. The fluorescence intensity of every well on the plate was read using a fluorescence microplate reader (Tecan or Molecular Devices). To evaluate the data, free mutein concentration, $c(mutein)_{free}$, was calculated based on the standard curve results, and plotted versus ligand concentration, c(Ligand). To obtain the ligand concentration at which formation the ligand/mutein complex was blocked by 50% (IC50), the curves were fitted by nonlinear regression with a single-sites binding model according to $c(mutein)_{free}=c(mutein)_{tot}/(1+c(Ligand)/IC50))$, with the total tracer concentration $c(mutein)_{tot}$ and the IC50 value as free parameters. Curve fitting was performed using GraphPad Prism 4 software.

The resulting IC$_{50}$ values are summarized in Tables 1A-D. Muteins selected against biotinylated and iron loaded Pvd I succinyl, Pvd II succinyl and Pvd III succinyl, respectively bound to all subtypes of the respective Pvd group i.e. muteins selected against biotinylated and iron loaded Pvd I succinyl bound with similar affinity to Pvd I succinyl, -succinamid, -α-ketoglutaryl with or without complexed iron ion, muteins selected against biotinylated and iron loaded Pvd II succinyl bound with similar affinity to Pvd II succinyl, -succinamid, -α-ketoglutaryl with or without complexed iron ion and muteins selected against biotinylated and iron loaded Pvd III succinyl bound with similar affinity to Pvd III succinyl, -succinamid, -α-ketoglutaryl with or without complexed iron ion. Most of the selected muteins bound with comparable affinity to all subtypes of the respective group with or without complexed iron ion.

The selection against biotinylated non-iron-loaded pyochelin resulted in lipocalin muteins binding preferably to non iron-loaded pyochelin, such as lipocalin muteins SEQ ID NO: 56 and 57 binding with two- to three digit nM affinity to iron-loaded Pch and with weak affinity or not at all to non-iron loaded Pch, and in lipocalin muteins such as SEQ ID NO: 55 binding preferably to iron-loaded pyochelin.

Affinity optimization of SEQ ID NO: 56 resulted in lipocalin muteins binding with improved affinity to non-iron loaded Pch and still with no or weak affinity to iron loaded Pch, whereas affinity optimization of SEQ ID NO: 55 resulted in lipocalin muteins binding with more than 75 fold improved affinity to non-iron loaded Pch but also with single digit nM affinity to iron loaded Pch.

Thus, with lipocalin mutein selection and optimization it was accomplished that only four different muteins are sufficient to bind all 10 subtypes of *P. aeruginosa* siderophores with and without complexed iron ion (Pvd I s, sa, αKG+/−Fe; Pvd II s, sa, αKG+/−Fe; Pvd III s, sa, αKG+/−Fe; Pch+/−Fe).

TABLE 1A

Binding of muteins to *P. aeruginosa* siderophore pyoverdine I succinyl, -succinamid, -α-ketoglutaryl +/− Fe$^{3+}$ in solution

| | Solution binding ELISA IC50: nM | | | | | |
|---|---|---|---|---|---|---|
| | Pvd I s (+Fe) | Pvd I sa (+Fe) | Pvd I aKG (+Fe) | Pvd I s (−Fe) | Pvd I sa (−Fe) | Pvd I aKG (−Fe) |
| SEQ ID NO: 2 | 24 | 19 | 13 | 26 | 19 | 13 |
| SEQ ID NO: 4 | 97 | 43 | 91 | 57 | 28 | 50 |
| SEQ ID NO: 5 | 97 | 49 | 73 | 57 | 32 | 42 |
| SEQ ID NO: 6 | 44 | 30 | 37 | 48 | 31 | 36 |
| SEQ ID NO: 7 | 173 | 126 | 59 | 290 | 129 | 53 |
| SEQ ID NO: 8 | 2.38 | 1.33 | 2.15 | 2.3 | 0.98 | 1.8 |
| SEQ ID NO: 9 | 3.3 | 1.37 | 2.4 | 3.7 | 1.6 | 2.9 |
| SEQ ID NO: 10 | 3.4 | 1.1 | 2.87 | 3.8 | 0.92 | 2.9 |
| SEQ ID NO: 11 | 2.97 | 1.9 | 2.57 | 4 | 2 | 3.1 |
| SEQ ID NO: 12 | 6.8 | 4.7 | 6.4 | 6.9 | 4.8 | 5.6 |
| SEQ ID NO: 13 | 0.5 | 0.27 | 0.37 | 0.36 | 0.2 | 0.24 |
| SEQ ID NO: 14 | 2.4 | 1.7 | 3.1 | 2.4 | 1.1 | 2.2 |
| SEQ ID NO: 15 | 1.1 | 0.59 | 1.2 | 0.86 | 0.42 | 0.69 |
| SEQ ID NO: 16 | 1.3 | 0.84 | 1.6 | 1 | 0.63 | 0.83 |
| SEQ ID NO: 18 | 5.3 | 2.2 | 3.9 | 2.8 | 1.8 | 2.5 |

TABLE 1B

Binding of muteins to soluble *P. aeruginosa* siderophore pyoverdine II succinyl, -succinamid, -α-ketoglutaryl +/− Fe3+ in solution

| | Solution binding ELISA IC50: nM | | | | | |
|---|---|---|---|---|---|---|
| | Pvd II s (+Fe) | Pvd II sa (+Fe) | Pvd II aKG (+Fe) | Pvd II s (−Fe) | Pvd II sa (−Fe) | Pvd II aKG (−Fe) |
| SEQ ID NO: 19 | 30 | 36 | 21 | 23 | 42 | 34 |
| SEQ ID NO: 20 | 48 | 40 | 85 | 63 | 40 | 89 |
| SEQ ID NO: 26 | 0.34 | 0.39 | 1.3 | 0.45 | 0.45 | 0.75 |
| SEQ ID NO: 27 | 0.78 | 1.53 | 1.97 | 1.02 | 1.12 | 1.4 |
| SEQ ID NO: 28 | 0.91 | 1.75 | 2.25 | 1.14 | 1.5 | 1.65 |
| SEQ ID NO: 29 | 0.68 | 1.5 | 1.9 | 0.95 | 1.2 | 1.6 |
| SEQ ID NO: 30 | 0.29 | 0.53 | 3 | 0.4 | 0.3 | 2.85 |
| SEQ ID NO: 31 | 0.29 | 0.29 | 1.1 | 0.38 | 0.35 | 0.64 |
| SEQ ID NO: 32 | 0.27 | 0.32 | 1.25 | 0.42 | 0.37 | 0.72 |
| SEQ ID NO: 33 | 0.28 | 0.32 | 1.3 | 0.4 | 0.32 | 0.7 |
| SEQ ID NO: 34 | 0.29 | 0.32 | 1.6 | 0.27 | 0.32 | 1.2 |
| SEQ ID NO: 35 | 0.33 | 0.39 | 0.76 | 0.34 | 0.42 | 0.99 |
| SEQ ID NO: 36 | 0.33 | 0.39 | 0.76 | 0.34 | 0.42 | 0.99 |
| SEQ ID NO: 37 | 0.19 | 0.28 | 2.1 | 0.2 | 0.3 | 1.4 |

TABLE 1C

Binding of muteins to *P. aeruginosa* siderophore pyoverdine III succinyl, -succinamid, -α-ketoglutaryl +/− Fe3+ in solution

| | Solution binding ELISA IC50: nM | | | | | |
|---|---|---|---|---|---|---|
| | Pvd III s (+Fe) | Pvd III sa (+Fe) | Pvd III aKG (+Fe) | Pvd III s (−Fe) | Pvd III sa (−Fe) | Pvd III aKG (−Fe) |
| SEQ ID NO: 39 | 146 | 147 | 23 | 95 | 94 | 23 |
| SEQ ID NO: 42 | 35 | 15 | 78 | 25 | 7.2 | 69 |
| SEQ ID NO: 43 | 0.31 | 0.25 | 1.4 | 0.6 | 0.46 | 1.90 |
| SEQ ID NO: 44 | 0.35 | 0.26 | 0.93 | 0.35 | 0.21 | 1.10 |
| SEQ ID NO: 45 | 0.75 | 0.43 | 1.50 | 0.41 | 0.46 | 1.70 |
| SEQ ID NO: 46 | 0.69 | 0.30 | 1.02 | 0.44 | 0.30 | 1.20 |
| SEQ ID NO: 47 | 0.37 | 0.30 | 0.82 | 0.17 | 0.28 | 0.58 |
| SEQ ID NO: 48 | 0.28 | 0.22 | 0.95 | 0.29 | 0.24 | 0.64 |
| SEQ ID NO: 49 | 0.32 | 0.27 | 0.79 | 0.21 | 0.27 | 0.62 |
| SEQ ID NO: 50 | 0.29 | 0.35 | 0.95 | 0.29 | 0.37 | 0.82 |
| SEQ ID NO: 51 | 0.37 | 0.37 | 0.97 | 0.35 | 0.34 | 1.1 |
| SEQ ID NO: 52 | 0.32 | 0.31 | 1 | 0.31 | 0.31 | 1 |
| SEQ ID NO: 53 | 0.21 | 0.25 | 0.54 | 0.19 | 0.63 | 0.33 |

TABLE 1D

Binding of muteins to *P. aeruginosa* siderophore pyochelin +/− Fe3+ in solution

| | Solution binding ELISA IC50: nM | |
|---|---|---|
| | pch (+Fe) | pch (−Fe) |
| SEQ ID NO: 55 | 361 | N/A |
| SEQ ID NO: 56 | N/A | 51 |
| SEQ ID NO: 57 | N/A | 147 |
| SEQ ID NO: 58 | N/A | 10 |
| SEQ ID NO: 59 | N/A | 11 |
| SEQ ID NO: 60 | 8.6 | 45 |
| SEQ ID NO: 61 | 5.1 | 42 |
| SEQ ID NO: 62 | 4.7 | 26 |
| SEQ ID NO: 63 | 5.6 | 26 |

For high throughput affinity ranking, the same assay was used however with less different concentrations of ligand.

Example 6: Affinity of Muteins Binding to P. aeruginosa Siderophores Determined in Biacore In a Surface Plasmon Resonance (SPR) based assay a Biacore T200 instrument (GE Healthcare) was used to measure the binding affinity of muteins to pyoverdine I succinyl, -succinamid, -α-ketoglutaryl with complexed iron ion or to pyoverdine II succinyl, -succinamid, -α-ketoglutaryl with complexed iron ion or to pyoverdine III succinyl, -succinamid, -α-ketoglutaryl with complexed iron ion. Muteins selected for binding to pyoverdines and negative control (SEQ ID NO: 64) were biotinylated for 2 h at room temperature applying an appropriate excess of EZ-Link NHS-PEG4-Biotin (Thermo, Cat#21329) followed by separation of non-reacted Biotin using a Zeba Spin Desalting Plate (Thermo, Cat#21329) according to the manufactures instructions.

In the SPR affinity assay, biotinylated muteins and negative control were captured on a sensor chip CAP using the Biotin CAPture Kit (GE Healthcare): Sensor Chip CAP is pre-immobilized with an ssDNA oligo. Undiluted Biotin CAPture Reagent (streptavidin conjugated with the complementary ss-DNA oligo) was applied at a flow rate of 2 µl/min for 300 s. Subsequently, 1 µg/ml to 100 µg/mL of biotinylated muteins or negative control were applied for 300 s at a flow rate of 5 µl/min. The reference channel was loaded with Biotin CAPture Reagent only.

To determine the binding affinity, four to five dilutions of the respective Pvd representatives (Pvd I, II, III, including succinyl, succinamid, -α-ketoglutaryl+Fe) at a concentration in the range of 5-2000 nM were prepared in HBS-EP+ buffer (GE Healthcare) and applied to the prepared chip surface. Applying a flow rate of 30 µl/min, a single cycle or multi cycle kinetics approach was used with a sample contact time of 120-180 s and a dissociation time of 900-2400 s. Absence of binding to the negative control SEQ ID NO: 64 was confirmed using a high concentration (e.g. 1200 nM) of the respective Pvd. After ligand immobilization, for analysis using single cycle kinetics all 4-5 concentrations of Pvd were applied consecutively in ascending order before the dissociation was monitored. For analysis using multi cycle kinetics 4 dilutions of Pvd were applied, each followed a dissociation phase. All measurements were performed at 25° C. Regeneration of the Sensor Chip CAP surface was achieved with an injection of 6 M Gua-HCl with 0.25 M NaOH followed by an extra wash with running buffer and a stabilization period of 120 s. Data were evaluated with Biacore T200 Evaluation software (V 1.0). Double referencing was used. A 1:1 Binding model was used to fit the raw data.

The resulting kinetic constants for a selection of lipocalin muteins are summarized in Tables 2A-C. Lipocalin muteins could be generated for each Pvd group binding in the subnM to low single digit nM range to all suptypes of the respective Pvd group. The natural ligand of wild type hNGAL Fe-enterobactin, however, is not bound by the Pvd specific lipocalin muteins.

TABLE 2A

Kinetic constants of Pvd I specific lipocalin muteins to Pvd I succinyl, −succinamid, and −α-ketoglutaryl complexed with $Fe^{3+}$.

| | Pvd I s (+Fe) | | | Pvd I sa (+Fe) | | | Pvd I k (+Fe) | | | Fe-Enterobactin |
|---|---|---|---|---|---|---|---|---|---|---|
| SEQ ID | $k_{on}$ [1/Ms] | $k_{off}$ [1/s] | $K_D$ [nM] | $k_{on}$ [1/Ms] | $k_{off}$ [1/s] | $K_D$ [nM] | $k_{on}$ [1/Ms] | $k_{off}$ [1/s] | $K_D$ [nM] | $K_D$ [nM] |
| SEQ ID NO: 8 | 5.37E+04 | 1.79E−04 | 3.33 | 1.11E+05 | 1.20E−04 | 1.08 | 4.74E+04 | 2.35E−04 | 4.95 | no bdg. |
| SEQ ID NO: 9 | 3.31E+04 | 3.30E−04 | 9.97 | 8.02E+04 | 2.57E−04 | 3.20 | 3.80E+04 | 5.32E−04 | 14.03 | no bdg. |
| SEQ ID NO: 10 | 3.47E+04 | 4.78E−04 | 13.78 | 8.63E+04 | 3.04E−04 | 3.52 | 5.02E+04 | 6.31E−04 | 12.57 | no bdg. |
| SEQ ID NO: 11 | 2.84E+04 | 4.04E−04 | 14.22 | 6.76E+04 | 2.97E−04 | 4.40 | 3.48E+04 | 5.86E−04 | 16.84 | no bdg. |
| SEQ ID NO: 13 | 1.17E+05 | 6.15E−05 | 0.53 | 1.65E+05 | 4.24E−05 | 0.26 | 9.51E+04 | 8.37E−05 | 0.88 | no bdg. |
| SEQ ID NO: 16 | 3.56E+04 | 1.88E−04 | 5.28 | 5.43E+04 | 1.56E−04 | 2.87 | 3.14E+04 | 2.54E−04 | 8.10 | no bdg. |

TABLE 2B

Kinetic constants of Pvd II specific lipocalin muteins to Pvd II succinyl, −succinamid, and −α-ketoglutaryl complexed with $Fe^{3+}$.

| | Pvd II s (+Fe) | | | Pvd II sa (+Fe) | | | Pvd II k (+Fe) | | | Fe-Enterobactin |
|---|---|---|---|---|---|---|---|---|---|---|
| SEQ ID | $k_{on}$ [1/Ms] | $k_{off}$ [1/s] | $K_D$ [nM] | $k_{on}$ [1/Ms] | $k_{off}$ [1/s] | $K_D$ [nM] | $k_{on}$ [1/Ms] | $k_{off}$ [1/s] | $K_D$ [nM] | $K_D$ [nM] |
| SEQ ID NO: 32 | 1.15E+06 | 1.09E−03 | 0.94 | 1.37E+06 | 9.55E−04 | 0.7 | 1.09E+05 | 3.74E−04 | 3.44 | no bdg. |
| SEQ ID NO: 33 | 1.23E+06 | 1.25E−03 | 1.02 | 1.41E+06 | 1.04E−03 | 0.74 | 9.93E+04 | 4.16E−04 | 4.19 | no bdg. |
| SEQ ID NO: 35 | 1.31E+05 | 4.59E−05 | 0.35 | 2.48E+05 | 4.58E−05 | 0.18 | 4.35E+04 | 1.49E−04 | 3.42 | no bdg. |
| SEQ ID NO: 36 | 1.10E+05 | 4.30E−05 | 0.39 | 1.38E+05 | 3.67E−05 | 0.27 | 2.86E+04 | 5.62E−05 | 1.97 | no bdg. |

TABLE 2C

Kinetic constants of Pvd III specific lipocalin muteins to Pvd III succinyl, –succinamid, and –α-ketoglutaryl complexed with $Fe^{3+}$.

| | Pvd III s (+Fe) | | | Pvd III sa (+Fe) | | | Pvd III k (+Fe) | | | Fe-Enterobactin |
|---|---|---|---|---|---|---|---|---|---|---|
| SEQ ID | $k_{on}$ [1/Ms] | $k_{off}$ [1/s] | $K_D$ [nM] | $k_{on}$ [1/Ms] | $k_{off}$ [1/s] | $K_D$ [nM] | $k_{on}$ [1/Ms] | $k_{off}$ [1/s] | $K_D$ [nM] | $K_D$ [nM] |
| SEQ ID NO: 43 | 7.05E+04 | 1.58E−04 | 2.24 | 3.52E+04 | 1.07E−04 | 3.04 | 5.73E+04 | 3.03E−04 | 5.29 | n.d. |
| SEQ ID NO: 44 | 5.62E+04 | 1.42E−04 | 2.53 | 3.03E+04 | 8.90E−05 | 2.94 | 4.82E+04 | 2.71E−04 | 5.64 | n.d. |
| SEQ ID NO: 45 | 5.90E+04 | 1.59E−04 | 2.70 | 3.27E+04 | 9.91E−05 | 3.03 | 4.73E+04 | 3.30E−04 | 6.99 | n.d. |
| SEQ ID NO: 46 | 8.32E+04 | 1.66E−04 | 2.00 | 4.36E+04 | 6.90E−05 | 1.58 | 7.67E+04 | 2.41E−04 | 3.15 | n.d. |
| SEQ ID NO: 47 | 7.89E+04 | 7.91E−05 | 1.00 | 1.28E+05 | 2.52E−05 | 0.20 | 2.92E+04 | 2.62E−04 | 8.97 | n.d. |
| SEQ ID NO: 48 | 6.70E+04 | 1.06E−04 | 1.58 | 1.48E+05 | 9.51E−05 | 0.64 | 2.72E+04 | 1.58E−04 | 5.81 | n.d. |
| SEQ ID NO: 49 | 6.88E+04 | 1.05E−04 | 1.52 | 1.34E+05 | 1.12E−04 | 0.84 | 2.81E+04 | 4.29E−05 | 1.53 | n.d. |
| SEQ ID NO: 53 | 5.10E+04 | 4.19E−05 | 0.82 | 6.73E+04 | 3.90E−05 | 0.58 | 3.88E+04 | 1.40E−04 | 3.60 | no bdg. |

In addition, absence of binding to various siderophores not belonging to the respective pyoverdine subgroup (I, II, III) and to MMP-9 was confirmed using the assay described above by applying high concentrations (≥1 μM) of the following analytes to the immobilized mutein: Fe-enterobactin, desferoxamine, pyochelin, pyoverdines from the respective other subgroups, MMP-9 proform and activated MMP-9. An overview of this analysis is provided in Table 3.

For determination of kinetic constants and resulting KD for the interaction of mutein SEQ ID NO: 62 with Pch+Fe the mutein or the negative control SEQ ID NO: 64 was immobilized to the surface of a CM5 chip using standard amine chemistry: The surface of the chip was activated using EDC and NHS. Subsequently, 5 μg/mL of mutein or the negative control solution in 10 mM acetate pH 4.0 was applied at a flow rate of 10 μl/min until a high immobilization level of approximately 2000 RU was achieved. Residual activated groups were quenched with ethanolamine. The reference channels were treated with EDC/NHS following ethanolamine (blank immobilization).

To determine the affinity, five dilutions of pyochelin (+Fe), were prepared in HBS-P+ buffer and applied to the prepared chip surface. The binding assay was carried out with a contact time of 180 s, dissociation times of 1200-1800 s and applying a flow rate of 30 μl/min. Measurements were performed at 25° C. Regeneration of the immobilized mutein surface was achieved by three consecutive injections of 10 mM Gly-HCl pH 1.5 (120 s) followed by an extra wash with running buffer and a stabilization period. Data were evaluated with Biacore T200 Evaluation software (V 1.0). Double referencing was used. The 1:1 Binding model was used to fit the raw data.

The resulting kinetic constant for SEQ ID NO: 62 is shown in Table 2D.

Using the same assay, absence of binding to siderophores different from pyochelin and to MMP-9 was confirmed by applying high concentrations (≥1 μM) of the following analytes to the immobilized mutein SEQ ID NO: 62: Fe-enterobactin, desferoxamine, pyoverdine, MMP-9 proform and activated MMP-9. An overview of the results is shown in Table 3.

TABLE 2D

Kinetic constants of pyochelin specific lipocalin mutein SEQ ID NO: 62 to pyochelin complexed with $Fe^{3+}$.

| | pch (+Fe) | | |
|---|---|---|---|
| SEQ ID | $k_{on}$ [1/Ms] | $k_{off}$ [1/s] | $K_D$ [nM] |
| SEQ ID NO: 62 | 2.25E+06 | 6.43E−04 | 0.29 |

TABLE 3

Specificity of lipocalin muteins binding to Pvd I, Pvd II, Pvd III or pyochelin.

| | Pvd I s (+Fe) | Pvd II s (+Fe) | Pvd III s (+Fe) | pch (+Fe) | Enterobactin (+Fe) | Desferoxamin | proform MMP-9 | activated MMP-9 |
|---|---|---|---|---|---|---|---|---|
| SEQ ID NO: 16 | + | − | − | − | − | − | − | − |
| SEQ ID NO: 36 | − | + | − | − | − | − | − | − |
| SEQ ID NO: 53 | − | − | + | − | − | − | − | − |
| SEQ ID NO: 62 | − | − | − | + | − | − | − | − |
| SEQ ID NO: 64 | − | − | − | − | + | − | − | − |

Example 7: Functional Testing of Muteins Binding to *P. aeruginosa* Siderophores; Inhibition of Iron Uptake To determine the functional iron uptake inhibition in living bacteria, a dose range concentration of the lipocalin muteins binding to *P. aeruginosa* siderophore are incubated for 1 hour with 100 nM radioactive iron loaded siderophore in a Tris.HCl 50 mM pH 8.0 buffer before being incubated for 30 minutes with bacteria at a final concentration of OD=1 at 595 nm in a 96 well plate. Subsequently bacteria are filtered with a cell harvester through a 96 well plate GF/B filter preincubated with a Poly Ethylene Imine solution at 5% and washed 3 times with Tris buffer. After filtering and drying, 30 µl of scintillant cocktail are added in each filter well before counting. To iron load pyoverdine, siderophore is incubated for 15 minutes with 55Fe—Cl3 in Tris buffer with a 4 to 1 ratio of pyoverdine and iron in a 200 µM final solution. For loading pyochelin with radioactive iron, a 40 µl solution of 55FeCl3 at 0.25 mM in HCl 0.5 N is added to a methanol solution of pyochelin at 1 mM. After a 15 minutes incubation time, 940 µl Tris HCl 50 mM pH 8.0 is added to obtain a 20 µM 55Fe-Pch solution with a 2 to 1 ratio between pyochelin and iron. The bacteria are prepared as follow: 10 ml of an overnight culture in Mueller Hinton Medium inoculated with an isolated clone is centrifuged and the washed pellet is resuspended in 25 ml of succinate medium and incubated under shaking for 2 hours. In parallel, 20 ml of Mueller Hinton Medium are inoculated with 5 ml of the overnight culture and incubated under shaking for 2 hours to be used as background iron uptake level. The 25 ml bacteria cultures are then centrifuged and washed with the corresponding medium before the pellet is resuspended in Tris.HCL 50 mM pH8.0 buffer and the OD at 595 nm measured to have a final concentration in the assay of OD=1.

Percentage of incorporation is calculated for each concentration point and the inhibition is calculated with in-house software. For this calculation, the maximum level of iron uptake is based on the value obtained in Minimum Succinate Medium without any lipocalin mutein, and the background value is obtained in the rich Mueller Hinton Medium where the siderophore receptor is not expressed.

TABLE 4

Lipocalin muteins block iron uptake of *P. aeruginosa* as exemplarily shown for lipocalin muteins SEQ ID NO: 16, 37, 53 and 62.

| SEQ ID | Iron uptake IC50: nM | | |
|---|---|---|---|
| SEQ ID NO: 16 | Pvd I s<br>121 | Pvd I sa<br>123 | Pvd I aKG<br>183 |
| SEQ ID NO: 37 | Pvd II s<br>118 | Pvd II sa<br>107 | Pvd II aKG<br>51 |
| SEQ ID NO: 53 | Pvd III s<br>74 | Pvd III sa<br>32 | Pvd III aKG<br>8 |
| SEQ ID NO: 62 | | | Pch<br>54 |

Example 8: Functional Testing of Muteins Binding to *P. aeruginosa* Siderophores; Growth Inhibition Bacterial growth inhibition is determined by incubating the muteins binding to *P. aeruginosa* siderophores in the Chelex treated Succinate Medium complemented with a Trace Element Solution and 0.1 mg/ml BSA with a MS bacterial culture diluted at a final OD of 0.05 at 595 nm in a black 96 well plate with transparent bottom. The plate is incubated over night at 37° C. with an every 20 minutes shaking and OD reading at 595 nm in an IEMS Reader MF from Thermo Labsystem. Growth inhibition is exemplarily shown for a Pvd I strain and Pvd I specific mutein SEQ ID NO: 16 in FIG. 4A, for a Pvd II strain and Pvd II specific mutein SEQ ID NO: 19, and SEQ ID NO: 36 in FIG. 4B, for a Pvd III strain and Pvd III specific mutein SEQ ID NO: 53 in FIG. 4C and for a Pvd I knock-out (ΔpvdA) strain relying on pyochelin for iron uptake to grow and pyochelin specific mutein SEQ ID NO: 62 in FIG. 4D. Control is bacterial growth without lipocalin mutein.

Example 9: Stability Assessment of Muteins

To determine melting temperatures as a general indicator for overall stability, siderophore-specific muteins (SEQ ID NOs: 13-18; 26, 31-36; 47-53; 58-62) at a protein concentration of 1 mg/ml in PBS (Gibco) were scanned (25-100° C.) at 1° C./min using a capillary nanoDSC instrument (CSC 6300, TA Instruments). The melting temperature (Tm) was calculated from the displayed thermogram using the integrated Nano Analyze software.

The resulting melting temperatures as well as the onset of melting for the lipcalin muteins (SEQ ID NOs: 13-18; 26, 31-36; 47-53; 58-62) are listed in Tables 5A-D below. For all Pvd groups as well as for pch lipocalin muteins with Tms in the range of 70° C., best lipocalin mutein for each Pvd type and pch ranging from 68 to 74° C., could be selected indicating good stability of the molecules.

TABLE 5A

Tm and onset of melting as determined by nanoDSC of Pvd I specific lipocalin muteins

| | nanoDSC | |
|---|---|---|
| SEQ ID | Tm ° C. | onset |
| SEQ ID NO: 13 | 59 | 51 |
| SEQ ID NO: 14 | 61 | 51 |
| SEQ ID NO: 15 | 68 | 59 |
| SEQ ID NO: 16 | 69 | 60 |
| SEQ ID NO: 17 | 61 | 53 |
| SEQ ID NO: 18 | 61 | 54 |

TABLE 5B

Tm and onset of melting as determined by nanoDSC of Pvd II specific lipocalin muteins

| | nanoDSC | |
|---|---|---|
| SEQ ID | Tm ° C. | onset |
| SEQ ID NO: 26 | 65 | 58 |
| SEQ ID NO: 31 | 67 | 60 |
| SEQ ID NO: 32 | 64 | 56 |
| SEQ ID NO: 33 | 67 | 61 |
| SEQ ID NO: 34 | 67 | 56 |
| SEQ ID NO: 35 | 71 | 63 |
| SEQ ID NO: 36 | 70 | 61 |

TABLE 5C

Tm and onset of melting as determined by nanoDSC of Pvd III specific lipocalin muteins

| | nanoDSC | |
|---|---|---|
| SEQ ID | Tm ° C. | onset |
| SEQ ID NO: 47 | 62 | 53 |
| SEQ ID NO: 48 | 64 | 55 |
| SEQ ID NO: 49 | 59 | 50 |
| SEQ ID NO: 50 | 61 | 52 |
| SEQ ID NO: 51 | 62 | 53 |
| SEQ ID NO: 52 | 59 | 49 |
| SEQ ID NO: 53 | 68 | 59 |

TABLE 5D

Tm and onset of melting as determined by nanoDSC of pch specific lipocalin muteins

| | nanoDSC | |
|---|---|---|
| SEQ ID | Tm ° C. | onset |
| SEQ ID NO: 58 | 63 | 51 |
| SEQ ID NO: 59 | 60 | 54 |
| SEQ ID NO: 60 | 68 | 56 |
| SEQ ID NO: 61 | 69 | 63 |
| SEQ ID NO: 62 | 74 | 63 |

To assess storage and freeze/thaw stability muteins at a conc. of 1 mg/ml in PBS were incubated for 1 week at 37° C. or underwent three freeze/thaw cycles. Active mutein was measured in a quantitative ELISA setting. Monomeric protein was measured in an analytical size exclusion chromatography. Exemplary data for SEQ ID NO: 16, 36, 53, 62 are shown in Table 6.

For assaying protein activity the following ELISA was applied: A 384-well plate suitable for fluorescence measurements (Greiner FLUOTRAC™ 600, black flat bottom, high-binding) was coated with 20 μL of Neutravidin (Thermo Scientific) at a concentration of 5 μg/ml in PBS overnight at 4° C. After washing, the Neutravidin-coated wells were blocked with 100 μl blocking buffer (2% w/v BSA in PBS containing 0.1% v/v Tween-20) for 1 h. After washing again, 20 μl of biotinylated and iron loaded pyoverdin I succinyl, pyoverdin II succinyl, pyoverdin III succinyl or biotinylated pyocheline at a concentration of 1 μg/ml in blocking buffer were added. The plate was washed and 20 μl of appropriately diluted protein standard, unstressed reference sample or stressed sample was transferred to the ELISA plate and incubated. To quantitate plate-bound protein, the ELISA plate was washed, residual supernatants were discarded and 20 μl HRP-labeled anti-hNGAL antibody was added at a predetermined optimal concentration in blocking buffer and incubated. After washing, 20 μl fluorogenic HRP substrate (QuantaBlu, Pierce) was added to each well, and the reaction was allowed to proceed for 20-30 minutes. The fluorescence intensity of every well on the plate was read using a fluorescence microplate reader (Tecan).

Unless otherwise stated all incubation steps were performed at for 1 h at room temperature and after each incubation step the plate was washed with 100 μl PBS-T buffer (PBS, 0.05% Tween 20) for five times using a Biotek ELx405 select CW washer.

For the ELISA described above, a calibration curve including 11 dilutions typically ranging from 0.008-500 ng/mL was prepared and three different, independent dilutions within the linear range of the calibration curve were prepared for each sample. Blocking buffer optionally supplemented with 1% human or murine plasma was used for the dilutions.

The calibration curve was fit using a 4 Parameter Logistic (4PL) nonlinear regression model and used to calculate active protein concentrations for the tested samples. The determined active protein concentrations were referenced against an unstressed sample stored at the same concentration and in the same matrix.

Analytical size exclusion chromatography was performed on an Agilent HPLC system with two Superdex 75 5/150 GL columns (GE Healthcare) in a row using PBS (Gibco) as an eluent at a flow rate of 0.3 mL/min.

To assess storage stability in plasma muteins at a conc. of 0.5 mg/ml were incubated for 1 week at 37° C. in human, mouse and rat plasma. Active mutein was measured in a quantitative ELISA setting as described.

All tested lipocalin muteins proved to be stable under all tested conditions.

TABLE 6

Stability after 3 freeze/thaw cycles (F/T); 1 week storage in PBS at 37° C. and 1 week storage in human (hu), mouse (mu) or rat plasma assessed by recovery of activity in qELISA and monomer content in analytical SEC: stable in qELISA = 100 +/− 15%; stable in aSEC = 100 +/− 5% (recovery of monomer peak area compared to non-stressed reference sample); for all samples including references a monomer content of 100 area percent has been detected.

| | | 3xF/T, −20° C. 1 mg/ml | | 1 week PBS, 37° C., 1 mg/ml | | 1 week | | |
|---|---|---|---|---|---|---|---|---|
| Mutein | siderophore | % recovery of activity in qELISA | % monomer in aSEC | % recovery of activity in qELISA | % monomer in aSEC | hu plasma, 37° C. | 1 week mu plasma, 37° C. | 1 week rat plasma, 37° C. |
| | | | | | | % recovery of activity in qELISA | | |
| SEQ ID NO: 16 | Pvd I | 102 | 98 | 86 | 98 | 86 | 100 | 100 |
| SEQ ID NO: 36 | Pvd II | 99 | 101 | 104 | 98 | 93 | 91 | 110 |
| SEQ ID NO: 53 | Pvd III | 98 | 99 | 107 | 102 | 92 | 83 | 101 |
| SEQ ID NO: 62 | pch | 107 | 100 | 95 | 104 | 97 | 102 | 95 |

Example 10: In Vivo Potency of Lipocalin Muteins in Mouse Model

The prophylactic effect of SEQ ID NO: 19 following intravenous (i.v.) administration in a *P. aeruginosa*-induced pulmonary infection in mice was studied.

SEQ ID NO: 19 was administered 1 hour before infection and at time of infection. Lung bacteria load was evaluated 24 h after infection.

The strain used in this study was *P. aeruginosa* (ATCC27853). Starting from *P. aeruginosa* stored at −80° C. in PBS/15% Glycerol, an overnight culture was conducted at 37° C. under shaking in Mueller-Hinton broth, and followed by additional subculture (100 µl overnight culture+100 ml of MHB) until end of logarithmic phase of growth. The culture was washed twice and resuspended in phosphate-buffer saline before to be frozen at 1E+09 CFU/ml. For each experiment a fresh vial was thawed and inoculum verified by viable counts.

7 to 8 weeks-old Male Swiss mice (5 animals/group) purchased from Janvier laboratories, (Route des chênes secs, 53940 Le Genest Saint Ile, France), were allowed at least 5 days acclimatization prior to use. Animals were maintained at temperature of 22±2° C. with relative humidity of 40-70% and 12-15 air fresh changes/hour. Light cycle 12/12 hours: light 7 a.m. to 7 p.m. (normal cycle). Temperature and relative humidity derivations are recorded continuously. Animals were housing 5 per cages and they allowed access to water and standard diet (AO4 C standard diet (SAFE)) ad libitum. All experiments were performed with approval of the ethic committee of Sanofi R&D (CEPAL).

Lung Infection was Induced by intranasal challenge of male Swiss mice with 1.E+07 CFU/mouse of *P. aeruginosa* in 50 µl NaCl 0.9%.

SEQ ID NO: 19 at concentrations of 200, 400, 1000 or 2000 µg/mouse was administered 1 h before infection and at time of infection, with i.v. bolus.

Twenty four hours after infection, animals were euthanized and bacterial count from lung homogenates were determined and expressed in log 10 CFU/ml as mean±sem.

Statistical analysis was performed using SAS v9.2. The Excel software 2003 was used for figure presentations. Comparisons on SEQ ID NO: 19 doses versus vehicle were evaluated with a one-way analysis of variance followed by Dunnett's test (ZAR J. H., «Biostatistical Analysis», Prentice Hall International Editions, 4ème édition, 1999; C. W. Dunnett, "A multiple comparison procedure for comparing several treatments with a control", J. Amer. Statist. Assoc., 50 (1955), pp. 1096-1121, 1955).

In a *P. aeruginosa*-induced lung infection model in mice, SEQ ID NO: 19 was administrated 1 hour before and at time of bacteria challenge and SEQ ID NO: 19 prevented the development of infection in mice in a dose-dependent manner. A significant prevention effect was observed for SEQ ID NO: 19 starting at 200 µg/mouse, with a maximal effect at 2000 µg/mouse.

Example 11: Crystallisation

To determine the three dimensional structure of SEQ ID NO: 31 protein in complex with Pvd-Fe the following procedure was applied.

The protein sequence depicted in FIG. 6 was cloned in the pET-24a plasmid and expressed as N-terminally tagged 6His-TEV protease recognition site construct.

The plasmid was used to transform BL21(DE3) Star *E. coli* cells and the resulted clones were inoculated in Overnight Express Instant TB Medium (Novagen) and the cells were harvested after 47 hours of incubation at 18° C. with 200 RPM agitation at final OD600 4.7. The cell pellet was resuspended in buffer containing 500 mM NaCl, 10 mM Imidazole, 1 mM $MgCl_2$, 1 mM TCEP, 5% glycerol and 20 mM Tris pH 7.4 and lysed by standard ultra-sonication procedure. The resulted extract was cleared by low speed centrifugation and supernatant was filtered throw 22 nm membrane before loading to Ni NTA (Qiagen) 5 ml column pre-equilibrated with 100 mM NaCl, 10 mM Imidazole, 100 mM HEPES pH 8 buffer. The protein was eluted by linear gradient of imidazole 10 mM to 300 mM and further dialyzed overnight to 100 mM NaCl, 10 mM Imidazole, 100 mM HEPES pH 8 buffer. The protein was concentrated to 20 mg/ml and loaded to Gel filtration Superdex 75 column (GE). The resulted protein was dialyzed to 100 mM NaCl, 10 mM HEPES pH 8 buffer overnight in the presence of TEV protease (1/50 ratio) to remove 6His N-terminal tag following by negative Ni NTA purification step as described above to separate the cleaved protein. Final protein was concentrated to 12 mg/ml in 100 mM NaCl, 50 mM HEPES pH 7.5 aliquoted, snap frozen in liquid nitrogen and stored at −80° C. for further use.

For crystallization the protein was incubated with 10× times higher molar concentration of Pvd-Fe overnight and plated for crystallization screening carried out in SBS format plates where 100 nL protein drops were mixed with 100 nL of crystallization screening solution in vapor diffusion sitting drops format experiments at 20° C. and 4° C. A number of crystallization hits were detected and crystallization conditions were further optimized in order to obtain well diffracting x-ray quality crystals.

The crystals diffraction quality was assessed using synchrotron x-ray source and the best diffracting crystals were obtained under 20% PEG3350 and 0.2M $LiSO_4$ conditions at 20° C. The best crystals were cryoprotected by increasing PEG3350 concentration to 35% than snap frozen in liquid nitrogen and 1.8 Å data set was collected at 100K temperature.

X-ray data were processed by MOSFLM and the protein structure was determined by molecular replacement method using pdb 1LKE as a search model and the structural model was further refined to Rfree=0.233−R=0.200 quality in P41212 with 2 ternary protein complexes per asymmetric unit.

The protein structure presents classical lipocalin scaffold with Pvd-Fe bound to both mutein proteins present in the asymmetric unit, FIG. 7. The amino acid residues involved in the Pvd-Fe binding analysed and presented on FIG. 8. The oxygens of the Pvd directly binding Fe are identified and presented on FIG. 9.

The present invention pertains to a polypeptide having binding specificity for pyoverdine type I, II, III or pyochelin, wherein the polypeptide comprises an hNGAL mutein that binds pyoverdine type I, II, III or pyochelin with detectable affinity.

In one embodiment the hNGAL mutein comprises a mutated amino acid residue at one or more positions corresponding to positions 28, 34, 36, 39-42, 44-47, 49, 52, 54-55, 65, 68, 70, 72-75, 77, 79-81, 87, 96, 100, 103, 106, 108, 123, 125, 127, 132, 134, 141 and 145 of the linear polypeptide sequence of the mature hNGAL (SEQ ID NO: 1).

In another embodiment said mutein is capable of binding pyoverdine type I complexed with iron with a $K_D$ of about 20 nM or lower when measured by Biacore T200 instrument in an assay essentially described in Example 6.

In another embodiment said hNGAL mutein is capable of binding Pvd type I succinyl, Pvd type I succinamid and Pvd type I a-ketoglutaryl with and without complexed iron, with an affinity measured by an IC50 value of about 200 nM or lower, when measured in an ELISA assay essentially described in Example 5.

In another embodiment the hNGAL mutein is capable of inhibiting iron uptake mediated by pyoverdine type I with an IC50 value of about 150 nM or lower in a competition ELISA format essentially described in Example 7.

In another embodiment the hNGAL mutein is capable of inhibiting bacterial growth of Pvd I strain in an assay essentially described in Example 8.

In another embodiment the hNGAL mutein comprises a mutated amino acid residue at one or more positions corresponding to positions 28, 36, 39-41, 46, 49, 52, 54-55, 59, 65, 68, 70, 72-75, 77, 79-81, 87, 96, 100, 103, 106, 125, 127, 132, 134 and 136 of the linear polypeptide sequence of the mature hNGAL (SEQ ID NO: 1).

In another embodiment the amino acid sequence of the hNGAL mutein comprises at least one of the following mutated amino acid residues in comparison with the linear polypeptide sequence of the mature hNGAL: Leu 36→Asn, Thr, Val, Trp or Phe; Ala 40→Gly, Asn, Thr or Phe; Ile 41→Arg, Ala, Thr, Phe or Trp; Gln 49→Ile, Leu, Vla, Ala or Pro; Tyr 52→Met, Trp or Pro; Ser 68→Asp, Vla or Glu; Leu 70→Gln, Trp, Asp or Thr; Arg 72→Trp, Ala, Ser, Leu, Pro or Glu; Lys 73→Asp, Leu, Ala, Glu or Asn; Asp 77→Arg, Leu, Tyr, Ser, Gln, Thr, Ile or Asn; Trp 79→Gln, Asp, Ser, Arg, Met or Glu; Arg 81→Gln, Gly, Ile, Glu, His or Asp; Asn 96→His, Ile, Gly, Tyr or Asp; Tyr 100→Lys, Glu, Asn, Ser, Phe or Tyr; Leu 103→Lys, Pro, Gln, His, Asp, Tyr, Glu, Trp or Asn; Tyr 106→His, Gln or Phe; Lys 125→Arg, Ser, Trp, Tyr, Val or Gly; Ser 127→Trp, Asn, Ala, Thr, Tyr, His, Ile, Val or Asp; Tyr 132→Trp, Asn, Gly or Lys; and Lys 134→Asn, His, Trp, Gly, Gln or Asp.

In another embodiment the amino acid sequence of the hNGAL mutein comprises the following substitution in comparison with the linear polypeptide sequence of the mature hNGAL: Gln 28→His; Lys 46→Glu; Thr 54→Vla or Ala; Ile 55→Vla; Lys 59→Arg; Asn 65→Asp or Gln; Ile 80→Thr; Cys 87→Ser or Asn; and Thr 136→Ala.

In another embodiment the hNGAL mutein comprises at least 1, 2, 3, 4, 5, 6, 7, 8, 9, 10, 11, 12, 13, 14, 15, 16, 17, 18, 19, 20 or 21 mutated amino acid residues at the sequence positions 28, 36, 39-41, 46, 49, 52, 54-55, 59, 65, 68, 70, 72-75, 77, 79-81, 87, 96, 100, 103, 106, 125, 127, 132, 134 and 136 of the linear polypeptide sequence of the mature human NGAL (SEQ ID NO: 1).

In another embodiment the hNGAL mutein comprises one of the following sets of amino acid substitutions in comparison with the linear polypeptide sequence of the mature hNGAL:

Gln 28→His; Leu 36→Asn; Ala 40→Gly; Ile 41→Trp; Gln 49→Ile; Tyr 52→Met; Ser 68→Val; Leu 70→Gln; Arg 72→Trp; Lys 73→Asp; Asp 77→Leu; Trp 79→Gln; Arg 81→Gln; Cys 87→Ser; Asn 96→His; Tyr 100→Lys; Leu 103→His; Tyr 106→His; Lys 125→Arg; Ser 127→Trp; Tyr 132→Trp; Lys 134→Asp;

Gln 28→His; Leu 36→Thr; Ala 40→Gly; Ile 41→Phe; Gln 49→Leu; Tyr 52→Trp; Leu 70→Trp; Arg 72→Ala; Lys 73→Leu; Asp 77→Tyr; Trp 79→Asp; Arg 81→Gly; Cys 87→Ser; Asn 96→Ile; Tyr 100→Glu; Leu 103→His; Tyr 106→Gln; Lys 125→Trp; Ser 127→Asn; Tyr 132→Asn; Lys 134→Gln;

Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Glu; Asp 77→Ser; Trp 79→Ser; Arg 81→Ile; Cys 87→Ser; Asn 96→Gly; Tyr 100→Asn; Leu 103→Lys; Tyr 106→His; Lys 125→Tyr; Ser 127→Ala; Tyr 132→Gly; Lys 134→Asn;

Gln 28→His; Leu 36→Phe; Ala 40→Asn; Ile 41→Arg; Gln 49→Pro; Tyr 52→Met; Ser 68→Asp; Leu 70→Thr; Arg 72→Glu; Lys 73→Ala; Asp 77→Arg; Trp 79→Arg; Arg 81→Ile; Cys 87→Ser; Asn 96→Tyr; Tyr 100→Lys; Leu 103→Pro; Tyr 106→Phe; Lys 125→Ser; Ser 127→Thr; Tyr 132→Trp; Lys 134→Gly;

Gln 28→His; Ala 40→Gly; Ile 41→Trp; Gln 49→Val; Tyr 52→Met; Ser 68→Val; Leu 70→Asp; Arg 72→Glu; Lys 73→Leu; Asp 77→Arg; Trp 79→Met; Arg 81→Glu; Cys 87→Ser; Asn 96→Asp; Tyr 100→Phe; Leu 103→Trp; Tyr 106→Gln; Lys 125→Gly; Ser 127→Tyr; Tyr 132→Trp; Lys 134→His;

Gln 28→His; Leu 36→Val; Ala 40→Phe; Ile 41→Phe; Gln 49→Ala; Tyr 52→Pro; Ser 68→Glu; Leu 70→Trp; Arg 72 Leu; Lys 73→Asn; Asp 77→Gln; Trp 79→Glu; Arg 81→His; Cys 87→Ser; Asn 96→Tyr; Leu 103→Tyr; Tyr 106→His; Lys 125→Val; Ser 127→His; Tyr 132→Lys; Lys 134→Trp;

Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Ile; Tyr 132→Gly; Lys 134→Asn;

Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Asp; Asp 77→Ser; Trp 79→Ser; Arg 81→Ile; Cys 87→Ser; Asn 96→Gly; Tyr 100→Asn; Leu 103→Asp; Tyr 106→His; Lys 125→Tyr; Ser 127→Val; Tyr 132→Gly; Lys 134→Asn;

Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Glu; Asp 77→Thr; Trp 79→Ser; Arg 81→Ile; Cys 87→Ser; Asn 96→Asp; Tyr 100→Asn; Leu 103→Glu; Tyr 106→His; Lys 125→Tyr; Ser 127→Asp; Tyr 132→Gly; Lys 134→Asn;

Gln 28→His; Leu 36→Trp; Ala 40→Thr; Ile 41→Thr; Gln 49→Pro; Tyr 52→Pro; Ser 68→Asp; Leu 70→Gln; Arg 72→Ser; Lys 73→Asp; Asp 77→Val; Trp 79→Ser; Arg 81→Ile; Cys 87→Ser; Asn 96→Gly; Tyr 100→Asn; Leu 103→Asn; Tyr 106→His; Lys 125→Tyr; Ser 127→Vla; Tyr 132→Gly; Lys 134→Asn;

Gln 28→His; Ala 40→Gly; Ile 41→Trp; Gln 49→Leu; Tyr 52→Met; Ser 68→Val; Leu 70→Asp; Arg 72→Glu; Lys 73→Leu; Asp 77→Arg; Trp 79→Met; Arg 81→Glu; Cys 87→Ser; Asn 96→Asp; Tyr 100→Ser; Leu 103→Trp; Tyr 106→Gln; Lys 125→Gly; Ser 127→Tyr; Tyr 132→Trp; Lys 134→His;

Gln 28→His; Leu 36→Trp; Ala 40→Thr; Ile 41→Thr; Gln 49→Pro; Tyr 52→Pro; Thr 54→Val; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Thr; Tyr 132→Gly; Lys 134→Asn;

Gln 28→His; Ala 40→Gly; Ile 41→Trp; Lys 46→Glu; Gln 49→Leu; Tyr 52→Met; Thr 54→Ala; Ile 55→Vla; Lys 59→Arg; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87→Asn; Asn 96→Asp; Tyr 100→sER; Leu 103→Trp; Tyr 106→Gln; Lys 125→Gly; Ser 127→Tyr; Tyr 132→Trp; Lys 134→His;

Leu 36→Trp; Asn 39→Asp; Ala 40→Thr; Ile 41→Thr; Gln 49→Pro; Tyr 52→Pro; Thr 54→Val; Asn 65→Asp; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Thr; Tyr 132→Gly; Lys 134→Asn; Thr 136→Ala;

Leu 36→Trp; Ala 40→Thr; Ile 41→Ala; Gln 49→Pro; Tyr 52→Pro; Thr 54→Val; Asn 65→Asp; Ser 68→Asp; Leu 70→Gln; Arg 72→Ser; Lys 73→Glu; Lys 75→Glu; Asp 77→Ser; Trp 79→Ser; Ile 80→Thr; Arg 81→Ile; Cys 87→Ser; Asn 96→Gly; Tyr 100→Ser; Leu 103→Gln; Tyr 106→His; Lys 125→Tyr; Ser 127→Thr; Tyr 132→Gly; Lys 134→Asn; Thr 136→Ala;

Gln 28→His; Ala 40→Gly; Ile 41→Trp; Lys 46→Glu; Gln 49→Leu; Tyr 52→Met; Thr 54→Ala; Ile 55→Vla; Lys 59→Arg; Asn 65→Asp; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87→Asn; Asn 96→Asp; Tyr 100→sER; Leu 103→Trp; Tyr 106→Gln; Lys 125→Gly; Ser 127→Tyr; Tyr 132→Trp; Lys 134→His; or

Gln 28→His; Ala 40→Gly; Ile 41→Trp; Lys 46→Glu; Gln 49→Leu; Tyr 52→Met; Thr 54→Ala; Ile 55→Vla; Lys 59→Arg; Asn 65→Gln; Ser 68→Val; Leu 70→Asp; Arg 72→Glu; Lys 73→Leu; Lys 74→Glu; Lys 75→Glu; Asp 77→Arg; Trp 79→Met; Ile 80→Thr; Arg 81→Glu; Ser 87→Asn; Asn 96→Asp; Tyr 100→sER; Leu 103→Trp; Tyr 106→Gln; Lys 125→Gly; Ser 127→Tyr; Tyr 132→Trp; Lys 134→His.

In another embodiment the hNGAL mutein comprises an amino acid sequence selected from the group consisting of SEQ ID NOs: 2-18 or a fragment or variant thereof.

In another embodiment said hNGAL mutein is capable of binding pyoverdine type II complexed with iron with a $K_D$ of about 20 nM or lower when measured by Biacore T200 instrument in an assay essentially described in Example 6.

In another embodiment said hNGAL mutein is capable of binding Pvd type II succinyl, Pvd type II succinamid and Pvd type II a-ketoglutaryl with and without complexed iron, with an affinity measured by an IC50 value of about 200 nM or lower, when measured in an ELISA assay essentially described in Example 5.

In another embodiment the hNGAL mutein is capable of inhibiting iron uptake mediated by pyoverdine type II with an IC50 value of about 150 nM or lower in a competition ELISA format essentially described in Example 7.

In another embodiment the hNGAL mutein is capable of inhibiting bacterial growth of Pvd II strain in an assay essentially described in Example 8.

In another embodiment said hNGAL mutein is capable of inhibiting growth of *P. aeruginosa* stains expressing pyoverdine type II in an assay essentially described in Example 9.

In another embodiment the hNGAL mutein comprises a mutated amino acid residue at one or more positions corresponding to positions 28, 36, 40-41, 49, 52, 54, 65, 68, 70, 72-75, 77, 79, 81, 87, 96, 100, 103, 106, 125, 127, 132 and 134 of the linear polypeptide sequence of the mature hNGAL (SEQ ID NO: 1).

In another embodiment the amino acid sequence of the hNGAL mutein comprises at least one of the following mutated amino acid residues in comparison with the linear polypeptide sequence of the mature hNGAL: Leu 36→Asn, Ile or Val; Ala 40→Glu, Gly, Asn, Thr or His; Ile 41→Arg, Val or Thr; Gln 49→Gly, Ala or Pro; Tyr 52→Asn, Gly or Pro; Ser 68→Asp, Arg or Glu; Leu 70→Arg or Trp; Arg 72→His, Ile, Ala, Ser or Gly; Lys 73→Asn, Met, Pro, Phe, Gln or Arg; Asp 77→His, Ile, Met, Lys, Gly or Asn; Trp 79→Ser, Tyr, Ala, Asp, Phe or Trp; Arg 81→Glu, Ser, Tyr or Asp; Asn 96→Met, Ile, Arg, Asp, Lys, Asn or Ala; Tyr 100→Lys, Glu, Asn, Ser, Phe or Tyr; Leu 103→Thr, Ile, Gln, Gly, Met, His, Trp or Val; Tyr 106→Met, Gln, Ala, Ile, Asn, Gly, Met or Phe; Lys 125→Ala, Ile or Asn; Ser 127→Lys, Arg, Ser, Met, Asp or Asn; Tyr 132→Met, Phe, Asn, Ala, Ile, Gly or Val; and Lys 134→Trp or Tyr.

In another embodiment the amino acid sequence of the hNGAL mutein comprises the following substitution in comparison with the linear polypeptide sequence of the mature hNGAL: Gln 28→His; Thr 54→Ala; Asn 65→Asp or Gln and Cys 87→Ser.

In another embodiment the hNGAL mutein comprises at least 1, 2, 3, 4, 5, 6, 7, 8, 9, 10, 11, 12, 13, 14, 15, 16, 17, 18, 19, 20 or 21 mutated amino acid residues at the sequence positions 28, 36, 40-41, 49, 52, 54, 65, 68, 70, 72-75, 77, 79, 81, 87, 96, 100, 103, 106, 125, 127, 132 and 134 of the linear polypeptide sequence of the mature human NGAL (SEQ ID NO: 1).

In another embodiment the hNGAL mutein comprises one of the following sets of amino acid substitutions in comparison with the linear polypeptide sequence of the natural wildtype hNGAL:

Gln 28→His; Leu 36→Val; Ala 40→Glu; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Tyr 100→Asn; Leu 103→Gln; Tyr 106→Met; Ser 127→Lys; Tyr 132→Gly; Lys 134→Trp;

Gln 28→His; Ala 40→Thr; Ile 41→Ile; Gln 49→Gly; Tyr 52→Asn; Ser 68→Asp; Leu 70→Arg; Arg 72→Ile; Lys 73→Met; Asp 77→His; Trp 79→Tyr; Arg 81→Glu; Cys 87→Ser; Asn 96→Ile; Tyr 100→Asn; Leu 103→Thr; Tyr 106→Gln; Lys 125→Ile; Ser 127→Arg; Tyr 132→Met; Lys 134→Trp;

Gln 28→His; Leu 36→Ile; Ala 40→Thr; Ile 41→Val; Gln 49→Gly; Tyr 52→Pro; Ser 68→Glu; Leu 70→Arg; Arg 72→Ala; Lys 73→Pro; Asp 77→Ile; Trp 79→Ser; Arg 81→Ser; Cys 87→Ser; Asn 96→Met; Tyr 100→Ser; Leu 103→Gly; Tyr 106→Ala; Lys 125→Lys; Tyr 132→Val; Lys 134→Trp;

Gln 28→His; Ala 40→Asn; Gln 49→Ala; Tyr 52→Pro; Ser 68→Glu; Leu 70→Arg; Arg 72→Ser; Lys 73→Gln; Asp 77→Met; Trp 79→Ala; Arg 81→Tyr; Cys 87→Ser; Asn 96→Arg; Tyr 100→Pro; Leu 103→Thr; Tyr 106→Ile; Lys 125→Lys; Ser 127→Met; Tyr 132→Phe; Lys 134→Trp;

Gln 28→His; Ala 40→His; Gln 49→Ala; Tyr 52→Pro; Ser 68→Glu; Leu 70→Asp; Arg 72→Gly; Lys 73→Arg; Asp 77→His; Trp 79→Trp; Arg 81→Glu; Cys 87→Ser; Asn 96→Arg; Tyr 100→Asp; Leu 103→Met; Tyr 106→Phe; Lys 125→Ala; Ser 127→Asp; Tyr 132→Asn; Lys 134→Trp;

Gln 28→His; Leu 36→Asn; Ala 40→Gly; Ile 41→Arg; Gln 49→Pro; Tyr 52→Trp; Ser 68→Arg; Leu 70→Trp; Arg 72→Asn; Lys 73→Gln; Asp 77→Lys; Trp 79→Asp; Arg 81→Glu; Cys 87→Ser; Asn 96→Asp; Tyr 100→Thr; Leu 103→Trp; Tyr 106→Asn; Lys 125→Asn; Ser 127→Met; Tyr 132→Ile; Lys 134→Tyr;

Gln 28→His; Leu 36→Vla; Ala 40→Thr; Ile 41→Thr; Gln 49→Gly; Tyr 52→Gly; Ser 68→Glu; Leu 70→Arg; Arg 72→Gly; Lys 73→Arg; Asp 77→Gly; Trp 79→Trp; Arg 81→Glu; Cys 87→Ser; Asn 96→Ala; Tyr 100→Trp; Leu 103→Ile; Tyr 106→Gly; Lys 125→Lys; Ser 127→Asn; Tyr 132→Val; Lys 134→Trp;

Gln 28→His; Leu 36→Val; Ala 40→Glu; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg

81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

Gln 28→His; Leu 36→Val; Ala 40→Thr; Ile 41→Val; Gln 49→Gly; Tyr 52→Pro; Ser 68→Glu; Leu 70→Arg; Arg 72→His; Lys 73→Asn; Asp 77→Asn; Trp 79→Ser; Arg 81→Glu; Cys 87→Ser; Leu 103→Gln; Tyr 106→Met; Ser 127→Lys; Tyr 132→Val; Lys 134→Trp;

Gln 28→His; Leu 36→Val; Ala 40→Thr; Ile 41→Val; Gln 49→Gly; Tyr 52→Pro; Ser 68→Glu; Leu 70→Arg; Arg 72→His; Asp 77→Asn; Trp 79→Phe; Arg 81→Glu; Cys 87→Ser; Asn 96→Lys; Tyr 100→His; Leu 103→Gln; Tyr 106→Met; Ser 127→Lys; Tyr 132→Ala; Lys 134→Trp;

Gln 28→His; Leu 36→Val; Ala 40→Gly; Ile 41→Val; Gln 49→Gly; Tyr 52→Pro; Ser 68→Glu; Leu 70→Arg; Arg 72→His; Lys 73→Asn; Asp 77→Asn; Trp 79→Trp; Arg 81→Glu; Cys 87→Ser; Tyr 100→Asn; Leu 103→His; Tyr 106→Met; Ser 127→Lys; Tyr 132→Gly; Lys 134→Trp;

Gln 28→His; Leu 36→Val; Ala 40→Thr; Ile 41→Ile; Gln 49→Gly; Tyr 52→Asn; Ser 68→Asp; Leu 70→Arg; Arg 72→Ile; Lys 73→Phe; Asp 77→His; Trp 79→Tyr; Arg 81→Asp; Cys 87→Ser; Leu 103→Met; Tyr 106→Gln; Lys 125→Ile; Ser 127→Arg; Tyr 132→Ile; Lys 134→Trp;

Gln 28→His; Leu 36→Val; Ala 40→Thr; Ile 41→Ile; Gln 49→Gly; Tyr 52→Asn; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp;

Gln 28→His; Leu 36→Val; Ala 40→Glu; Ile 41→Val; Gln 49→Gly; Tyr 52→Pro; Asn 65→Asp; Ser 68→Glu; Leu 70→Arg; Arg 72→His; Lys 73→Asn; Asp 77→Asn; Trp 79→Phe; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

Gln 28→His; Leu 36→Val; Ala 40→Glu; Ile 41→Val; Gln 49→Gly; Tyr 52→Pro; Asn 65→Gln; Ser 68→Glu; Leu 70→Arg; Arg 72→His; Lys 73→Asn; Asp 77→Asn; Trp 79→Phe; Arg 81→Glu; Cys 87→Ser; Asn 96→Lys; Tyr 100→Asn; Leu 103→Val; Tyr 106→Met; Lys 125→Asn; Ser 127→Lys; Tyr 132→Gly; Lys 134→Trp;

Gln 28→His; Leu 36→Val; Ala 40→Thr; Ile 41→Ile; Gln 49 Gly; Tyr 52 Asn; Thr 54→Ala; Asn 65 Asp; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp;

Gln 28→His; Leu 36→Val; Ala 40→Thr; Ile 41→Ile; Gln 49→Gly; Tyr 52→Asn; Thr 54→Ala; Asn 65→Gln; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp;

Leu 36→Val; Ala 40→Thr; Ile 41→Ile; Gln 49→Gly; Tyr 52→Asn; Thr 54→Ala; Asn 65→Asp; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp; or

Leu 36→Val; Ala 40→Thr; Ile 41→Ile; Gln 49→Gly; Tyr 52→Asn; Thr 54→Ala; Asn 65→Gln; Ser 68→Asp; Leu 70→Arg; Arg 72→Ile; Lys 73→Arg; Asp 77→His; Trp 79→Tyr; Arg 81→Asp; Cys 87→Ser; Leu 103→Thr; Tyr 106→Gln; Lys 125→Ile; Ser 127→Arg; Tyr 132→Ile; Lys 134→Trp.

In another embodiment the hNGAL mutein comprises an amino acid sequence selected from the group consisting of SEQ ID NOs: 19-37 or a fragment or variant thereof.

In another embodiment said mutein is capable of binding pyoverdine type III complexed with iron with a $K_D$ of about 20 nM or lower when measured by Biacore T200 instrument in an assay essentially described in Example 6.

In another embodiment said hNGAL mutein is capable of binding Pvd type III succinyl, Pvd type III succinamid and Pvd type III a-ketoglutaryl with and without complexed iron, with an affinity measured by an IC50 value of about 200 nM or lower, when measured in an assay essentially described in Example 5.

In another embodiment the hNGAL mutein is capable of inhibiting iron uptake mediated by pyoverdine type III with an IC50 value of about 150 nM or lower in a competition ELISA format essentially described in Example 7.

In another embodiment the hNGAL mutein is capable of inhibiting bacterial growth of Pvd III strain in an assay essentially described in Example 8.

In another embodiment the hNGAL mutein comprises a mutated amino acid residue at one or more positions corresponding to positions 28, 36, 40-42, 45-47, 49, 52, 65, 68, 70, 72-73, 77, 79, 81, 87, 96, 100, 103, 105-106, 125, 127, 132, 134 and 145 of the linear polypeptide sequence of the mature hNGAL (SEQ ID NO: 1).

In another embodiment the amino acid sequence of the hNGAL mutein comprises at least one of the following mutated amino acid residues in comparison with the linear polypeptide sequence of the mature hNGAL: Leu 36→Phe or Glu; Ala 40→Trp, Leu or Arg; Ile 41→Met, Arg, Ala, Leu or Trp; Gln 49→His, Ile, Arg, Lys, Met or Pro; Tyr 52→Asn, Tyr, Arg, Ser or Met; Ser 68→Asp, Asn, Glu or Gln; Leu 70→Lys, Asn or Arg; Arg 72→Leu, Arg, Gln or Tyr; Lys 73→His, Leu, Ala, Pro, Gln or Tyr; Asp 77→Ala, Ile, Lys, Gln or Arg; Trp 79→Ser or Asp; Arg 81→His, Ala, Ser or Val; Asn 96→Met, Ile, Arg, Gly, Leu or Val; Tyr 100→Ala, Ile, Asn, Pro or Asp; Leu 103→Gln, Gly, Phe or Pro; Tyr 106→Glu; Lys 125→Trp or Thr; Ser 127→Val, His, Ile, Phe or Ala; Tyr 132→Phe; and Lys 134→Trp, Gln or Glu.

In another embodiment the amino acid sequence of the hNGAL mutein comprises the following substitution in comparison with the linear polypeptide sequence of the mature hNGAL: Gln 28→His; Leu 42→Arg; Asp 45→Gly; Lys 46→Arg; Asp 47→Asn; Asn 65→Asp; Cys 87→Ser; Ser 105→Pro and Thr 145→Pro.

In another embodiment the hNGAL mutein comprises at least 1, 2, 3, 4, 5, 6, 7, 8, 9, 10, 11, 12, 13, 14, 15, 16, 17, 18, 19, 20 or 21 mutated amino acid residues at the sequence positions 28, 36, 40-42, 45-47, 49, 52, 65, 68, 70, 72-73, 77, 79, 81, 87, 96, 100, 103, 105-106, 125, 127, 132, 134 and 145 of the linear polypeptide sequence of the mature human NGAL (SEQ ID NO: 1)

In another embodiment the hNGAL mutein comprises one of the following sets of amino acid substitutions in comparison with the linear polypeptide sequence of the mature hNGAL:

Gln 28→His; Leu 36→Phe; Ala 40→Trp; Ile 41→Met; Gln 49→His; Tyr 52→Asn; Ser 68→Glu; Leu 70→Lys; Arg 72→Gln; Lys 73→Ala; Asp 77→Ile; Trp 79→Ser; Arg 81→His; Cys 87→Ser; Asn 96→Ile; Tyr 100→Asn; Leu 103→Gly; Tyr 106→Glu; Lys 125→Trp; Ser 127→His; Tyr 132→Phe; Lys 134→Gln;

Gln 28→His; Leu 36→Phe; Ala 40→Arg; Ile 41→Trp; Gln 49→Ile; Tyr 52→Tyr; Ser 68→Gln; Leu 70→Asn; Arg 72→Trp; Lys 73→Leu; Asp 77→Ala; Trp 79→Ser; Arg 81→Ser; Cys 87→Ser; Asn 96→Arg; Tyr 100→Ile; Leu 103→Pro; Tyr 106→Glu; Lys 125→Thr; Ser 127→Ile; Tyr 132→Phe; Lys 134→Glu;

Gln 28→His; Leu 36→Phe; Ala 40→Leu; Ile 41→Leu; Gln 49→Arg; Tyr 52→Arg; Ser 68→Asp; Leu 70→Arg; Arg 72→Leu; Lys 73→Tyr; Asp 77→Ile; Trp 79→Ser; Arg 81→Ala; Cys 87→Ser; Asn 96→Gly; Tyr 100→Ala; Leu 103→Phe; Tyr 106→Glu; Lys 125→Trp; Ser 127→Ala; Lys 134→Glu;

Gln 28→His; Leu 36→Phe; Ala 40→Trp; Ile 41→Arg; Gln 49→Pro; Tyr 52→Ser; Ser 68→Asn; Leu 70→Arg; Arg 72→Trp; Lys 73→Pro; Asp 77→Arg; Trp 79→Ser; Arg 81→Ser; Cys 87→Ser; Asn 96→Met; Tyr 100→Pro; Leu 103→Gly; Tyr 106→Glu; Lys 125→Trp; Ser 127→Phe; Tyr 132→Phe; Lys 134→Glu;

Gln 28→His; Leu 36→Glu; Ala 40→Leu; Ile 41→Ala; Gln 49→Lys; Tyr 52→Met; Ser 68→Glu; Leu 70→Arg; Lys 73→His; Asp 77→Gln; Trp 79→Asp; Arg 81→Ala; Cys 87→Ser; Asn 96→Leu; Tyr 100→Asp; Leu 103→Gln; Tyr 106→Glu; Ser 127→Val; Tyr 132→Phe; Lys 134→Trp;

Gln 28→His; Leu 36→Glu; Ala 40→Leu; Ile 41→Ala; Gln 49→Met; Tyr 52→Met; Ser 68→Glu; Leu 70→Arg; Lys 73→Gln; Asp 77→Lys; Trp 79→Asp; Arg 81→Vla; Cys 87→Ser; Asn 96→Leu; Tyr 100→Asp; Leu 103→Gln; Tyr 106→Glu; Ser 127→Val; Tyr 132→Phe; Lys 134→Trp;

Gln 28→His; Leu 36→Glu; Ala 40→Leu; Ile 41→Thr; Gln 49→Met; Tyr 52→Met; Ser 68→Glu; Leu 70→Arg; Lys 73→Arg; Asp 77→Lys; Trp 79→Asp; Arg 81→Vla; Cys 87→Ser; Asn 96→Vla; Tyr 100→Asp; Leu 103→Gln; Tyr 106→Glu; Ser 127→Val; Tyr 132→Phe; Lys 134→Trp;

Gln 28→His; Leu 36→Glu; Ala 40→Leu; Ile 41→Ala; Gln 49→Met; Tyr 52→Met; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Tyr 106→Glu; Ser 127→Val; Tyr 132→Phe; Lys 134→Trp;

Gln 28→His; Leu 36→Glu; Ala 40→Leu; Ile 41→Ala; Gln 49→Lys; Tyr 52→Met; Ser 68→Glu; Leu 70→Arg; Lys 73→Tyr; Asp 77→Gln; Trp 79→Asp; Arg 81→Vla; Cys 87→Ser; Asn 96→-; Tyr 100→Glu; Leu 103→Gln; Tyr 106→Glu; Ser 127→Val; Tyr 132→Phe; Lys 134→Trp;

Gln 28→His; Leu 36→Glu; Ala 40→Leu; Ile 41→Ala; Leu 42→Arg; Gln 49→Met; Tyr 52→Met; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

Gln 28→His; Leu 36→Glu; Ala 40→Leu; Ile 41→Ala; Asp 47→Asn; Gln 49→Met; Tyr 52→Met; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; Thr 145→Pro;

Gln 28→His; Leu 36→Glu; Ala 40→Leu; Ile 41→Ala; Asp 45→Gly; Lys 46→Arg; Gln 49→Met; Tyr 52→Met; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

Gln 28→His; Leu 36→Glu; Ala 40→Leu; Ile 41→Ala; Leu 42 Arg; Gln 49→Met; Tyr 52→Met; Asn 65→Asp; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp;

Gln 28→His; Leu 36→Glu; Ala 40→Leu; Ile 41→Ala; Asp 47→Asn; Gln 49→Met; Tyr 52→Met; Asn 65→Asp; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; Thr 145→Pro;

Gln 28→His; Leu 36→Glu; Ala 40→Leu; Ile 41→Ala; Asp 45→Gly; Lys 46→Arg; Gln 49→Met; Tyr 52→Met; Asn 65→Asp; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp; or Leu 36→Glu; Ala 40→Leu; Ile 41→Ala; Leu 42→Arg; Gln 49→Met; Tyr 52→Met; Asn 65→Asp; Ser 68→Glu; Leu 70→Arg; Lys 73→His; Asp 77→Lys; Trp 79→Asp; Arg 81→Vla; Cys 87→Ser; Asn 96→Leu; Tyr 100→Asp; Leu 103→Gln; Ser 105→Pro; Tyr 106→Glu; Ser 127→Val; Tyr 132→Phe; Lys 134→Trp.

In another embodiment the polypeptide comprises an amino acid sequence selected from the group consisting of SEQ ID NOs: 38-53 or a fragment or variant thereof.

In another embodiment said hNGAL mutein is capable of binding pyochelin complexed with iron with a $K_D$ of about 20 nM or lower when measured by Biacore T200 instrument in an assay essentially described in Example 6.

In another embodiment said hNGAL mutein is capable of binding pyochelin with complexed iron, with an affinity measured by an IC50 value of about 500 nM or lower, when measured in an assay essentially described in Example 5.

In another embodiment said hNGAL mutein is capable of binding pyochelin without complexed iron, with an affinity measured by an IC50 value of about 200 nM or lower, when measured in an assay essentially described in Example 5.

In another embodiment said hNGAL mutein is capable of binding pyochelin with and without complexed iron, with an affinity measured by an IC50 value of about 200 nM or lower, when measured in an assay essentially described in Example 5.

In another embodiment the hNGAL mutein is capable of inhibiting iron uptake mediated by pyochelin with an IC50 value of about 150 nM or lower in a competition ELISA format essentially described in Example 7.

In another embodiment the hNGAL mutein is capable of inhibiting bacterial growth of Pvd I knock-out (ΔpvdA) in an assay essentially described in Example 8 In another embodiment the hNGAL mutein comprises a mutated amino acid residue at one or more positions corresponding to positions 28, 34, 36, 40-41, 44-46, 49, 52, 54, 65, 68, 70, 72-74, 77, 79-81, 87, 96, 100, 103, 106, 108, 123, 125, 127, 132, 134 and 141 of the linear polypeptide sequence of the mature hNGAL (SEQ ID NO: 1).

In another embodiment the amino acid sequence of the hNGAL mutein comprises at least one of the following mutated amino acid residues in comparison with the linear polypeptide sequence of the mature hNGAL: Leu 36→His, Met or Val; Ala 40→Ile, Gln, Tyr or Phe; Ile 41→Leu, His or Trp; Gln 49→His, Arg, Ser or Ala; Tyr 52→Leu, Trp or Pro; Ser 68→Asp or His; Leu 70→Arg or Trp; Arg 72→His, Ile, Ala, Ser or Gly; Lys 73→Asn, Met, Pro, Phe, Gln or Arg; Asp 77→Arg, Thr, Pro or Asp; Trp 79→Ala, Arg, Lys or Asp; Arg 81→Thr, Ile or Trp; Asn 96→Met, Asn, Pro or Ala; Tyr 100→Gly, His or Glu; Leu 103→Gly, Met, His or Gln; Tyr 106→Met, Gly, Arg or Trp; Lys 125→Trp, Phe, Gly or Leu; Ser 127→Arg, Trp, Asp or Ile; Tyr 132→Ala, Glu or Thr; and Lys 134→Leu, Val, Asn or Phe.

In another embodiment the amino acid sequence of the hNGAL mutein comprises the following substitution in comparison with the linear polypeptide sequence of the mature hNGAL: Gln 28→His; Val 34→Leu; Glu 44→Gly; Asp 45→Gly; Lys→Arg or Tyr; Asn 65→Asp; Ile 80→Thr; Cys 87→Ser; Leu 94→Phe; Val 108→Ala; Phe 123→Ser and Thr 141→Ala.

In another embodiment the hNGAL mutein comprises at least 1, 2, 3, 4, 5, 6, 7, 8, 9, 10, 11, 12, 13, 14, 15, 16, 17, 18, 19, 20 or 21 mutated amino acid residues at the sequence positions 28, 34, 36, 40-41, 44-46, 49, 52, 54, 65, 68, 70, 72-74, 77, 79-81, 87, 96, 100, 103, 106, 108, 123, 125, 127, 132, 134 and 141 of the linear polypeptide sequence of the mature human NGAL (SEQ ID NO: 1).

In another embodiment the hNGAL mutein comprises one of the following sets of amino acid substitutions in comparison with the linear polypeptide sequence of the mature hNGAL:

Gln 28→His; Ala 40→Ile; Ile 41→Leu; Gln 49→His; Tyr 52→Leu; Ser 68→His; Leu 70→Thr; Arg 72→Lys; Lys 73→Trp; Asp 77→Ile; Trp 79→Ser; Arg 81→His; Cys 87→Ser; Asn 96→Met; Tyr 100→Asn; Leu 103→His; Tyr 106→Met; Lys 125→Trp; Ser 127→Asp; Tyr 132→Glu; Lys 134→Leu;

Gln 28→His; Leu 36→His; Ala 40→Gln; Ile 41→Trp; Gln 49→Arg; Tyr 52→Trp; Ser 68→Asp; Leu 70→Asp; Arg 72→Ala; Lys 73→Ile; Asp 77→His; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe;

Gln 28→His; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Arg 81→Ile; Cys 87→Ser; Asn 96→Ala; Tyr 100→Gly; Leu 103→Met; Tyr 106→Trp; Lys 125→Gly; Ser 127→Trp; Tyr 132→Thru; Lys 134→Val;

Gln 28→His; Leu 36→Val; Ala 40→Tyr; Ile 41→Trp; Gln 49→Ala; Ser 68→Asp; Leu 70→Arg; Arg 72→Trp; Lys 73→Arg; Asp 77→Arg; Trp 79→Asp; Arg 81→Trp; Cys 87→Ser; Asn 96→Pro; Tyr 100→Glu; Leu 103→Gln; Tyr 106→Arg; Lys 125→Leu; Ser 127→Arg; Tyr 132→Ala; Lys 134→Asn;

Gln 28→His; Vla 34→Leu; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Ile 80→Thr; Arg 81→Ile; Cys 87→Ser; Asn 96→Ala; Tyr 100→Gly; Leu 103→Met; Tyr 106→Trp; Phe 123→Ser; Lys 125→Gly; Ser 127→Trp; Tyr 132→Thru; Lys 134→Val; Thr 141→Ala;

Gln 28→His; Leu 36→Met; Ala 40→Phe; Ile 41→His; Gln 49→Ser; Tyr 52→Pro; Ser 68→His; Leu 70→Pro; Arg 72→Trp; Lys 73→Ala; Asp 77→Ala; Trp 79→Lys; Ile 80→Thr; Arg 81→Ile; Cys 87→Ser; Asn 96→Ala; Tyr 100→Gly; Leu 103→Met; Tyr 106→Trp; Phe 123→Ser; Lys 125→Gly; Ser 127→Trp; Tyr 132→Thru; Lys 134→Val;

Gln 28→His; Leu 36→His; Ala 40→Gln; Ile 41→Trp; Asp 45→Gly; Lys 46→Arg; Gln 49→Arg; Tyr 52→Trp; Ser 68→Asp; Leu 70→Asp; Arg 72→Ala; Lys 73→Ile; Asp 77→Leu; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe;

Gln 28→His; Leu 36→His; Ala 40→Gln; Ile 41→Trp; Glu 44→Gly; Lys 46→Tyr; Gln 49→Arg; Tyr 52→Trp; Ser 68→Asp; Leu 70→Asp; Arg 72→Ala; Lys 73→Ile; Lys 74→Glu; Asp 77→His; Trp 79→Arg; Arg 81→Thr; Cys 87→Ser; Leu 94→Phe; Tyr 100→His; Leu 103→Gly; Tyr 106→Gly; Val 108→Ala; Lys 125→Phe; Ser 127→Ile; Tyr 132→Ala; Lys 134→Phe; or

Leu 36→His; Ala 40→Gln; Ile 41→Trp; Asp 45→Gly; Lys 46→Arg; Gln 49→Arg; Tyr 52→Trp; Asn 65→Asp; Ser 68→Asp; Leu 70→Asp; Arg 72→Ala; Lys 73→Ile; Asp 77→Leu; Trp 79→Arg; Arg 81→Thr; Cys 87→Ser; Tyr 100→His; Leu 103→Gly; Tyr 106→Gly; Lys 125→Phe; Ser 127→Ile; Tyr 132→Ala; Lys 134→Phe.

In another embodiment the polypeptide comprises an amino acid sequence selected from the group consisting of SEQ ID NOs: 54-63 or a fragment or variant thereof.

In another embodiment the polypeptide comprises an amino acid sequence selected from the group consisting of SEQ ID NOs: 2-63 or a fragment or variant thereof.

In another embodiment said hNGAL mutein comprises one or more non-native cysteine residues substituting one or more amino acids of a wild type hNGAL.

In another embodiment said hNGAL mutein comprises at least one amino acid substitution of a native cysteine residue by another amino acid.

In another embodiment said another amino acid is a serine residue.

In another embodiment the hNGAL mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxins, a metal complex, a metal, and colloidal gold.

In another embodiment the hNGAL mutein is fused at its N-terminus and/or its C-terminus to a fusion partner which is a protein, or a protein domain or a peptide.

In another embodiment the hNGAL mutein is conjugated to a compound that extends the serum half-life of the polypeptide.

In another embodiment the polypeptide comprises a compound that extends the serum half-life is selected from the group consisting of a polyalkylene glycol molecule, hydroethylstarch, a Fc part of an immunoglobulin, a CH3 domain of an immunoglobulin, a CH4 domain of an immunoglobulin, an albumin binding peptide, and an albumin binding protein.

In another embodiment the polyalkylene glycol is polyethylene (PEG) or an activated derivative thereof.

In another embodiment a nucleic acid molecule is encompassed comprising a nucleotide sequence encoding any of the polypeptides mentioned herein.

In another embodiment the nucleic acid molecule is operably linked to a regulatory sequence to allow expression of said nucleic acid molecule.

In another embodiment the nucleic acid molecule is comprised in a vector or in a phagemid vector.

In another embodiment a host cell is encompassed containing a nucleic acid molecule of any one of the ones mentioned herein.

In another embodiment a method of producing any of the polypeptide described herein is encompassed, wherein the polypeptide is produced starting from the nucleic acid coding for the polypeptide by means of genetic engineering methods.

In another embodiment the polypeptide is produced in a bacterial or eucaryotic host organism and is isolated from this host organism or its culture.

In another embodiment a composition is encompassed comprising one or more polypeptides selected from the group consisting of (i) a polypeptide specific for pyoverdine type I, (ii) a polypeptide specific for pyoverdine type II, (iii) a polypeptide specific for pyoverdine type III and (iv) a polypeptide specific for pyochelin.

In another embodiment the composition comprises two or more polypeptides selected from the group consisting of (i) a polypeptide specific for pyoverdine type I, (ii) a polypeptide specific for pyoverdine type II, (iii) a polypeptide specific for pyoverdine type III and (iv) a polypeptide specific for pyochelin.

In another embodiment the composition comprises three or four polypeptides selected from the group consisting of (i) a polypeptide specific for pyoverdine type I, (ii) a polypeptide specific for pyoverdine type II, (iii) a polypeptide specific for pyoverdine type III and (iv) a polypeptide specific for pyochelin.

In another embodiment the composition comprises the polypeptide specific for pyoverdine type I.

In another embodiment the composition comprises the polypeptide specific for pyoverdine type II.

In another embodiment the composition comprises the polypeptide specific for pyoverdine type III.

In another embodiment the composition comprises the polypeptide specific for pyochelin.

In another embodiment said composition further includes at least one pharmaceutically acceptable adjuvant, diluent or carrier.

In another embodiment the method of binding pyoverdine type I, II, III and/or pyochelin in a subject comprises administering to said subject an effective amount of any of the compositions mentioned herein.

In another embodiment a method is encompassed for inhibiting or lessening growth of *P. aeruginosa* in a subject, comprising administering to said subject an effective amount of the composition of any of the ones mentioned herein.

In another embodiment a kit is encompassed comprising one or more containers, separately or in admixture, and the composition of any of the ones mentioned herein.

In another embodiment the use of (i) a polypeptide according to any polypeptide mentioned herein capable of binding to pyoverdine type I, (ii) a polypeptide according to any polypeptide mentioned herein capable of binding to pyoverdine type II, (iii) a polypeptide according to any polypeptide mentioned herein capable of binding to pyoverdine type III and/or (iv) a polypeptide according to any polypeptide mentioned herein capable of binding to pyochelin is encompassed, for the binding of pyoverdine type I, II, III and/or pyochelin in a subject.

In another embodiment the use of (i) a polypeptide according to any polypeptide mentioned herein capable of binding to pyoverdine type I, (ii) a polypeptide according to any polypeptide mentioned herein capable of binding to pyoverdine type II, (iii) a polypeptide according to any polypeptide mentioned herein capable of binding to pyoverdine type III and/or (iv) a polypeptide according to any polypeptide mentioned herein capable of binding to pyochelin is encompassed, for preventing or reducing iron-uptake by *P. aeruginosa* through pyochelin and/or pyoverdine in a subject.

In another embodiment the use of (i) a polypeptide according to any polypeptide mentioned herein capable of binding to pyoverdine type I, (ii) a polypeptide according to any polypeptide mentioned herein capable of binding to pyoverdine type II, (iii) a polypeptide according to any polypeptide mentioned herein capable of binding to pyoverdine type III and/or (iv) a polypeptide according to any polypeptide mentioned herein capable of binding to pyochelin is encompassed, for the treatment or alleviation of *P. aeruginosa* biofilm infection in a subject.

In another embodiment the *P. aeruginosa* biofilm infection is acute or chronic infection.

In another embodiment said first, second, third and/or fourth polypeptides are administered in combination, including concurrently, concomitantly or in series.

In another embodiment said first, second, third and/or fourth polypeptides are administered independent from each other, including at individual intervals at independent points of time.

In another embodiment a combination comprising (i) a polypeptide according to any polypeptide mentioned herein capable of binding to pyoverdine type I, (ii) a polypeptide according to any polypeptide mentioned herein capable of binding to pyoverdine type II, (iii) a polypeptide according to any polypeptide mentioned herein capable of binding to pyoverdine type III and/or (iv) a polypeptide according to any polypeptide mentioned herein capable of binding to pyochelin.

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of the invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

The invention claimed is:

1. A human neutrophil gelatinase-associated lipocalin (hNGAL) mutein polypeptide having binding specificity for pyoverdine type III, wherein the hNGAL mutein comprises 10 or more mutations at positions 36, 40, 41, 42, 49, 52, 65, 68, 70, 73, 77, 79, 81, 87, 96, 100, 103, 105, 106, 127, and 134 of SEQ ID NO: 1.

2. The hNGAL mutein polypeptide of claim 1, wherein the hNGAL mutein comprises ten or more of the following mutations of SEQ ID NO: 1: L36E, A40L, I41A, L42R, Q49M, Y52M, N65D, S68E, L70R, K73H, D77K, W79D, R81V, C87S, N96L, Y100D, L103Q, S105P, Y106E, S127V, K134W.

3. The hNGAL mutein polypeptide of claim 1, wherein the hNGAL mutein comprises SEQ ID NO: 53.

4. The hNGAL mutein polypeptide of claim 1, wherein the hNGAL mutein has binding specificity for pyoverdine type III succinyl, pyoverdine type III succinamid, and/or pyoverdine type III α-ketoglutaryl.

5. The hNGAL mutein polypeptide of claim 1, wherein the hNGAL mutein is capable of binding pyoverdine type III complexed with iron with a $K_D$ of about 200 nM or lower.

6. The hNGAL mutein polypeptide of claim 1, wherein the hNGAL mutein comprises 12 or more mutations at positions 36, 40, 41, 42, 49, 52, 65, 68, 70, 73, 77, 79, 81, 87, 96, 100, 103, 105, 106, 127, and 134 of SEQ ID NO: 1.

7. A human neutrophil gelatinase-associated lipocalin (hNGAL) mutein polypeptide having binding specificity for pyoverdine type III, wherein the hNGAL mutein comprises 15 or more mutations at positions 36, 40, 41, 42, 49, 52, 65, 68, 70, 73, 77, 79, 81, 87, 96, 100, 103, 105, 106, 127, and 134.

8. The hNGAL mutein polypeptide of claim 7, wherein the hNGAL mutein comprises 15 or more of the following mutations of SEQ ID NO: 1: L36E, A40L, I41A, L42R, Q49M, Y52M, N65D, S68E, L70R, K73H, D77K, W79D, R81V, C87S, N96L, Y100D, L103Q, S105P, Y106E, S127V, K134W.

9. The hNGAL mutein polypeptide of claim 7, wherein the hNGAL mutein comprises SEQ ID NO: 53.

10. The hNGAL mutein polypeptide of claim 7, wherein the hNGAL mutein has binding specificity for pyoverdine type III succinyl, pyoverdine type III succinamid, and/or pyoverdine type III α-ketoglutaryl.

11. The hNGAL mutein polypeptide of claim 7, wherein the hNGAL mutein is capable of binding pyoverdine type III complexed with iron with a $K_D$ of about 200 nM or lower.

12. A human neutrophil gelatinase-associated lipocalin (hNGAL) mutein polypeptide having binding specificity for pyoverdine type III, wherein the hNGAL mutein comprises SEQ ID NO: 53.

13. The hNGAL mutein polypeptide of claim 12, wherein the hNGAL mutein consists of SEQ ID NO: 53.

14. The hNGAL mutein polypeptide of claim 12, wherein the hNGAL mutein has binding specificity for pyoverdine type III succinyl, pyoverdine type III succinamid, and/or pyoverdine type III α-ketoglutaryl.

15. The hNGAL mutein polypeptide of claim 12, wherein the hNGAL mutein is capable of binding pyoverdine type III complexed with iron with a $K_D$ of about 200 nM or lower.

16. A composition comprising the hNGAL mutein polypeptide of claim 1, and at least one pharmaceutically acceptable adjuvant, diluent, or carrier.

17. A composition comprising the hNGAL mutein polypeptide of claim 7, and at least one pharmaceutically acceptable adjuvant, diluent, or carrier.

18. A composition comprising the hNGAL mutein polypeptide of claim 12, and at least one pharmaceutically acceptable adjuvant, diluent, or carrier.

* * * * *

SEQUENCE LISTING

<160> NUMBER OF SEQ ID NOS: 133

<210> SEQ ID NO 1
<211> LENGTH: 178
<212> TYPE: PRT
<213> ORGANISM: Artificial Sequence
<220> FEATURE:
<223> OTHER INFORMATION: NGAL wt

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 2
<211> LENGTH: 178
<212> TYPE: PRT
<213> ORGANISM: Artificial Sequence
<220> FEATURE:
<223> OTHER INFORMATION: NGAL mutein Pvd type I binder 1

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Asn Ala Gly Asn Gly Trp Leu Arg Glu Asp Lys Asp Pro
        35                  40                  45

Ile Lys Met Met Ala Thr Ile Tyr Glu Leu Lys Glu Asp Lys Ser Tyr
    50                  55                  60

Asn Val Thr Val Val Gln Phe Trp Asp Lys Lys Cys Leu Tyr Gln Ile
65                  70                  75                  80

Gln Thr Phe Val Pro Gly Ser Gln Pro Gly Glu Phe Thr Leu Gly His
                85                  90                  95

Ile Lys Ser Lys Pro Gly His Thr Ser His Leu Val Arg Val Val Ser
            100                 105                 110

Thr Asn Tyr Asn Gln His Ala Met Val Phe Phe Lys Arg Val Trp Gln
        115                 120                 125

Asn Arg Glu Trp Phe Asp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 3
<211> LENGTH: 178
<212> TYPE: PRT
<213> ORGANISM: Artificial Sequence
<220> FEATURE:
<223> OTHER INFORMATION: NGAL mutein Pvd type I binder 2

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Thr Ala Gly Asn Gly Phe Leu Arg Glu Asp Lys Asp Pro
        35                  40                  45

Leu Lys Met Trp Ala Thr Ile Tyr Glu Leu Lys Glu Asp Lys Ser Tyr
    50                  55                  60

Asn Val Thr Ser Val Trp Phe Ala Leu Lys Lys Cys Tyr Tyr Asp Ile
65                  70                  75                  80

Gly Thr Phe Val Pro Gly Ser Gln Pro Gly Glu Phe Thr Leu Gly Ile
                85                  90                  95

Ile Lys Ser Glu Pro Gly His Thr Ser Gln Leu Val Arg Val Val Ser
            100                 105                 110

Thr Asn Tyr Asn Gln His Ala Met Val Phe Phe Lys Trp Val Asn Gln
        115                 120                 125

Asn Arg Glu Asn Phe Gln Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 4
<211> LENGTH: 178
<212> TYPE: PRT
<213> ORGANISM: Artificial Sequence
<220> FEATURE:
<223> OTHER INFORMATION: NGAL mutein Pvd type I binder 3

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Thr Leu Arg Glu Asp Lys Asp Pro
        35                  40                  45

Pro Lys Met Pro Ala Thr Ile Tyr Glu Leu Lys Glu Asp Lys Ser Tyr
    50                  55                  60

Asn Val Thr Asp Val Gln Phe Ser Glu Lys Lys Cys Ser Tyr Ser Ile
65                  70                  75                  80

Ile Thr Phe Val Pro Gly Ser Gln Pro Gly Glu Phe Thr Leu Gly Gly
                85                  90                  95

```
Ile Lys Ser Asn Pro Gly Lys Thr Ser His Leu Val Arg Val Val Ser
                100                 105                 110

Thr Asn Tyr Asn Gln His Ala Met Val Phe Phe Lys Tyr Val Ala Gln
            115                 120                 125

Asn Arg Glu Gly Phe Asn Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 5
<211> LENGTH: 178
<212> TYPE: PRT
<213> ORGANISM: Artificial Sequence
<220> FEATURE:
<223> OTHER INFORMATION: NGAL mutein Pvd type I binder 4

<400> SEQUENCE: 5

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Phe Ala Gly Asn Asn Arg Leu Arg Glu Asp Lys Asp Pro
        35                  40                  45

Pro Lys Met Met Ala Thr Ile Tyr Glu Leu Lys Glu Asp Lys Ser Tyr
    50                  55                  60

Asn Val Thr Asp Val Thr Phe Glu Ala Lys Lys Cys Arg Tyr Arg Ile
65                  70                  75                  80

Ile Thr Phe Val Pro Gly Ser Gln Pro Gly Glu Phe Thr Leu Gly Tyr
                85                  90                  95

Ile Lys Ser Lys Pro Gly Pro Thr Ser Phe Leu Val Arg Val Val Ser
                100                 105                 110

Thr Asn Tyr Asn Gln His Ala Met Val Phe Phe Lys Ser Val Thr Gln
            115                 120                 125

Asn Arg Glu Trp Phe Gly Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 6
<211> LENGTH: 178
<212> TYPE: PRT
<213> ORGANISM: Artificial Sequence
<220> FEATURE:
<223> OTHER INFORMATION: NGAL mutein Pvd type I binder 5

<400> SEQUENCE: 6

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

Val Val Gly Leu Ala Gly Asn Gly Trp Leu Arg Glu Asp Lys Asp Pro
            35                  40                  45

Val Lys Met Met Ala Thr Ile Tyr Glu Leu Lys Glu Asp Lys Ser Tyr
 50                  55                  60

Asn Val Thr Val Val Asp Phe Glu Leu Lys Lys Cys Arg Tyr Met Ile
 65                  70                  75                  80

Glu Thr Phe Val Pro Gly Ser Gln Pro Gly Glu Phe Thr Leu Gly Asp
                 85                  90                  95

Ile Lys Ser Phe Pro Gly Trp Thr Ser Gln Leu Val Arg Val Val Ser
                100                 105                 110

Thr Asn Tyr Asn Gln His Ala Met Val Phe Phe Lys Gly Val Tyr Gln
                115                 120                 125

Asn Arg Glu Trp Phe His Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 7
<211> LENGTH: 178
<212> TYPE: PRT
<213> ORGANISM: Artificial Sequence
<220> FEATURE:
<223> OTHER INFORMATION: NGAL mutein Pvd type I binder 6

<400> SEQUENCE: 7

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Phe Phe Leu Arg Glu Asp Lys Asp Pro
            35                  40                  45

Ala Lys Met Pro Ala Thr Ile Tyr Glu Leu Lys Glu Asp Lys Ser Tyr
 50                  55                  60

Asn Val Thr Glu Val Trp Phe Leu Asn Lys Lys Cys Gln Tyr Glu Ile
 65                  70                  75                  80

His Thr Phe Val Pro Gly Ser Gln Pro Gly Glu Phe Thr Leu Gly Tyr
                 85                  90                  95

Ile Lys Ser Tyr Pro Gly Tyr Thr Ser His Leu Val Arg Val Val Ser
                100                 105                 110

Thr Asn Tyr Asn Gln His Ala Met Val Phe Phe Lys Val Val His Gln
                115                 120                 125

Asn Arg Asp Lys Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 8
<211> LENGTH: 178
<212> TYPE: PRT
<213> ORGANISM: Artificial Sequence -continued
<220> FEATURE:
<223> OTHER INFORMATION: NGAL mutein Pvd type I binder 7

<400> SEQUENCE: 8

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Thr Leu Arg Glu Asp Lys Asp Pro
        35                  40                  45

Pro Lys Met Pro Ala Thr Ile Tyr Glu Leu Lys Glu Asp Lys Ser Tyr
    50                  55                  60

Asn Val Thr Asp Val Gln Phe Pro Glu Lys Lys Cys Ile Tyr Ser Thr
65              70                  75                  80

Ile Thr Phe Val Pro Gly Ser Gln Pro Gly Glu Phe Thr Leu Gly Gly
                85                  90                  95

Ile Lys Ser Ser Pro Gly Gln Thr Ser His Leu Val Arg Val Val Ser
            100                 105                 110

Thr Asn Tyr Asn Gln His Ala Met Val Phe Phe Lys Tyr Val Ile Gln
        115                 120                 125

Asn Arg Glu Gly Phe Asn Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 9
<211> LENGTH: 178
<212> TYPE: PRT
<213> ORGANISM: Artificial Sequence
<220> FEATURE:
<223> OTHER INFORMATION: NGAL mutein Pvd type I binder 8

<400> SEQUENCE: 9

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Thr Leu Arg Glu Asp Lys Asp Pro
        35                  40                  45

Pro Lys Met Pro Ala Thr Ile Tyr Glu Leu Lys Glu Asp Lys Ser Tyr
    50                  55                  60

Asn Val Thr Asp Val Gln Phe Pro Asp Lys Lys Cys Ile Tyr Ser Ile
65              70                  75                  80

Ile Thr Phe Val Pro Gly Ser Gln Pro Gly Glu Phe Thr Leu Gly Gly
                85                  90                  95

Ile Lys Ser Asn Pro Gly Asp Thr Ser His Leu Val Arg Val Val Ser
            100                 105                 110

Thr Asn Tyr Asn Gln His Ala Met Val Phe Phe Lys Tyr Val Val Gln
        115                 120                 125

Asn Arg Glu Gly Phe Asn Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
            165                 170                 175

Asp Gly

<210> SEQ ID NO 10
<211> LENGTH: 178
<212> TYPE: PRT
<213> ORGANISM: Artificial Sequence
<220> FEATURE:
<223> OTHER INFORMATION: NGAL mutein Pvd type I binder 9

<400> SEQUENCE: 10

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Thr Leu Arg Glu Asp Lys Asp Pro
        35                  40                  45

Pro Lys Met Pro Ala Thr Ile Tyr Glu Leu Lys Glu Asp Lys Ser Tyr
    50                  55                  60

Asn Val Thr Asp Val Gln Phe Pro Glu Lys Lys Cys Thr Tyr Ser Ile
65                  70                  75                  80

Ile Thr Phe Val Pro Gly Ser Gln Pro Gly Glu Phe Thr Leu Gly Asp
                85                  90                  95

Ile Lys Ser Asn Pro Gly Glu Thr Ser His Leu Val Arg Val Met Ser
            100                 105                 110

Thr Asn Tyr Asn Gln His Ala Met Val Phe Phe Lys Tyr Val Asp Gln
        115                 120                 125

Asn Arg Glu Gly Phe Asn Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 11
<211> LENGTH: 178
<212> TYPE: PRT
<213> ORGANISM: Artificial Sequence
<220> FEATURE:
<223> OTHER INFORMATION: NGAL mutein Pvd type I binder 10

<400> SEQUENCE: 11

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Trp Ala Gly Asn Thr Thr Leu Arg Glu Asp Lys Asp Pro
        35                  40                  45

Pro Lys Met Pro Ala Thr Ile Tyr Glu Leu Lys Glu Asp Lys Ser Tyr
    50                  55                  60

Asn Val Thr Asp Val Gln Phe Pro Asp Lys Lys Cys Val Tyr Ser Ile
65                  70                  75                  80

Ile Thr Phe Val Pro Gly Ser Gln Pro Gly Glu Phe Thr Leu Gly Gly
                85                  90                  95

```
Ile Lys Ser Asn Pro Gly Asn Thr Ser His Leu Val Arg Val Val Ser
            100                 105                 110

Thr Asn Tyr Asn Gln His Ala Met Val Phe Phe Lys Tyr Val Val Gln
            115                 120                 125

Asn Arg Glu Gly Phe Asn Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 12
<211> LENGTH: 178
<212> TYPE: PRT
<213> ORGANISM: Artificial Sequence
<220> FEATURE:
<223> OTHER INFORMATION: NGAL mutein Pvd type I binder 11

<400> SEQUENCE: 12

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Gly Trp Leu Arg Glu Asp Lys Asp Pro
        35                  40                  45

Leu Lys Met Met Ala Thr Ile Tyr Glu Leu Lys Glu Asp Lys Ser Tyr
50                  55                  60

Asn Val Thr Val Val Asp Phe Glu Leu Lys Lys Cys Arg Tyr Met Ile
65                  70                  75                  80

Glu Thr Phe Val Pro Gly Ser Gln Pro Gly Glu Phe Thr Leu Gly Asp
                85                  90                  95

Ile Lys Ser Ser Pro Gly Trp Thr Ser Gln Leu Val Arg Val Val Ser
            100                 105                 110

Thr Asn Tyr Asn Gln His Ala Met Val Phe Phe Lys Gly Val Tyr Gln
            115                 120                 125

Asn Arg Glu Trp Phe His Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 13
<211> LENGTH: 178
<212> TYPE: PRT
<213> ORGANISM: Artificial Sequence
<220> FEATURE:
<223> OTHER INFORMATION: NGAL mutein Pvd type I binder 12

<400> SEQUENCE: 13

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30
```

-continued

Val Val Gly Trp Ala Gly Asn Thr Thr Leu Arg Glu Asp Lys Asp Pro
                35                  40                  45

Pro Lys Met Pro Ala Val Ile Tyr Glu Leu Lys Glu Asp Lys Ser Tyr
 50                  55                  60

Asn Val Thr Asp Val Gln Phe Pro Lys Glu Cys Ile Tyr Ser Thr
 65                  70                  75                  80

Ile Thr Phe Val Pro Gly Ser Gln Pro Gly Glu Phe Thr Leu Gly Gly
                 85                  90                  95

Ile Lys Ser Ser Pro Gly Gln Thr Ser His Leu Val Arg Val Val Ser
                100                 105                 110

Thr Asn Tyr Asn Gln His Ala Met Val Phe Phe Lys Tyr Val Thr Gln
                115                 120                 125

Asn Arg Glu Gly Phe Asn Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 14
<211> LENGTH: 178
<212> TYPE: PRT
<213> ORGANISM: Artificial Sequence
<220> FEATURE:
<223> OTHER INFORMATION: NGAL mutein Pvd type I binder 13

<400> SEQUENCE: 14

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Gly Trp Leu Arg Glu Asp Glu Asp Pro
                35                  40                  45

Leu Lys Met Met Ala Ala Val Tyr Glu Leu Arg Glu Asp Lys Ser Tyr
 50                  55                  60

Asn Val Thr Val Val Asp Phe Glu Leu Glu Glu Cys Arg Tyr Met Thr
 65                  70                  75                  80

Glu Thr Phe Val Pro Gly Asn Gln Pro Gly Glu Phe Thr Leu Gly Asp
                 85                  90                  95

Ile Lys Ser Ser Pro Gly Trp Thr Ser Gln Leu Val Arg Val Val Ser
                100                 105                 110

Thr Asn Tyr Asn Gln His Ala Met Val Phe Phe Lys Gly Val Tyr Gln
                115                 120                 125

Asn Arg Glu Trp Phe His Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 15
<211> LENGTH: 178
<212> TYPE: PRT
<213> ORGANISM: Artificial Sequence
<220> FEATURE:
<223> OTHER INFORMATION: NGAL mutein Pvd type I binder 14

<400> SEQUENCE: 15

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asp Thr Thr Leu Arg Glu Asp Lys Asp Pro
        35                  40                  45

Pro Lys Met Pro Ala Val Ile Tyr Glu Leu Lys Glu Asp Lys Ser Tyr
    50                  55                  60

Asp Val Thr Asp Val Gln Phe Pro Glu Lys Glu Cys Ile Tyr Ser Thr
65                  70                  75                  80

Ile Thr Phe Val Pro Gly Ser Gln Pro Gly Glu Phe Thr Leu Gly Gly
                85                  90                  95

Ile Lys Ser Ser Pro Gly Gln Thr Ser His Leu Val Arg Val Val Ser
            100                 105                 110

Thr Asn Tyr Asn Gln His Ala Met Val Phe Phe Lys Tyr Val Thr Gln
        115                 120                 125

Asn Arg Glu Gly Phe Asn Ile Ala Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 16
<211> LENGTH: 178
<212> TYPE: PRT
<213> ORGANISM: Artificial Sequence
<220> FEATURE:
<223> OTHER INFORMATION: NGAL mutein Pvd type I binder 15

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Trp Ala Gly Asn Thr Ala Leu Arg Glu Asp Lys Asp Pro
        35                  40                  45

Pro Lys Met Pro Ala Val Ile Tyr Glu Leu Lys Glu Asp Lys Ser Tyr
    50                  55                  60

Asp Val Thr Asp Val Gln Phe Pro Glu Lys Glu Cys Ile Tyr Ser Thr
65                  70                  75                  80

Ile Thr Phe Val Pro Gly Ser Gln Pro Gly Glu Phe Thr Leu Gly Gly
                85                  90                  95

Ile Lys Ser Ser Pro Gly Gln Thr Ser His Leu Val Arg Val Val Ser
            100                 105                 110

Thr Asn Tyr Asn Gln His Ala Met Val Phe Phe Lys Tyr Val Thr Gln
        115                 120                 125

Asn Arg Glu Gly Phe Asn Ile Ala Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 17
<211> LENGTH: 178
<212> TYPE: PRT
<213> ORGANISM: Artificial Sequence
<220> FEATURE:
<223> OTHER INFORMATION: NGAL mutein Pvd type I binder 16

<400> SEQUENCE: 17

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Gly Trp Leu Arg Glu Asp Glu Asp Pro
        35                  40                  45

Leu Lys Met Met Ala Ala Val Tyr Glu Leu Arg Glu Asp Lys Ser Tyr
    50                  55                  60

Asp Val Thr Val Val Asp Phe Glu Leu Glu Glu Cys Arg Tyr Met Thr
65                  70                  75                  80

Glu Thr Phe Val Pro Gly Asn Gln Pro Gly Glu Phe Thr Leu Gly Asp
                85                  90                  95

Ile Lys Ser Ser Pro Gly Trp Thr Ser Gln Leu Val Arg Val Val Ser
            100                 105                 110

Thr Asn Tyr Asn Gln His Ala Met Val Phe Phe Lys Gly Val Tyr Gln
        115                 120                 125

Asn Arg Glu Trp Phe His Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 18
<211> LENGTH: 178
<212> TYPE: PRT
<213> ORGANISM: Artificial Sequence
<220> FEATURE:
<223> OTHER INFORMATION: NGAL mutein Pvd type I binder 17

<400> SEQUENCE: 18

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Gly Trp Leu Arg Glu Asp Glu Asp Pro
        35                  40                  45

Leu Lys Met Met Ala Ala Val Tyr Glu Leu Arg Glu Asp Lys Ser Tyr
    50                  55                  60

Gln Val Thr Val Val Asp Phe Glu Leu Glu Glu Cys Arg Tyr Met Thr
65                  70                  75                  80

Glu Thr Phe Val Pro Gly Asn Gln Pro Gly Glu Phe Thr Leu Gly Asp
                85                  90                  95

```
Ile Lys Ser Ser Pro Gly Trp Thr Ser Gln Leu Val Arg Val Val Ser
            100                 105                 110

Thr Asn Tyr Asn Gln His Ala Met Val Phe Phe Lys Gly Val Tyr Gln
            115                 120                 125

Asn Arg Glu Trp Phe His Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 19
<211> LENGTH: 178
<212> TYPE: PRT
<213> ORGANISM: Artificial Sequence
<220> FEATURE:
<223> OTHER INFORMATION: NGAL mutein Pvd type II binder 1

<400> SEQUENCE: 19

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Glu Val Leu Arg Glu Asp Lys Asp Pro
        35                  40                  45

Gly Lys Met Pro Ala Thr Ile Tyr Glu Leu Lys Glu Asp Lys Ser Tyr
    50                  55                  60

Asn Val Thr Glu Val Arg Phe His Asn Lys Lys Cys Asn Tyr Ser Ile
65                  70                  75                  80

Glu Thr Phe Val Pro Gly Ser Gln Pro Gly Glu Phe Thr Leu Gly Asn
                85                  90                  95

Ile Lys Ser Asn Pro Gly Gln Thr Ser Met Leu Val Arg Val Val Ser
            100                 105                 110

Thr Asn Tyr Asn Gln His Ala Met Val Phe Phe Lys Lys Val Lys Gln
            115                 120                 125

Asn Arg Glu Gly Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 20
<211> LENGTH: 178
<212> TYPE: PRT
<213> ORGANISM: Artificial Sequence
<220> FEATURE:
<223> OTHER INFORMATION: NGAL mutein Pvd type II binder 2

<400> SEQUENCE: 20

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Thr Ile Leu Arg Glu Asp Lys Asp Pro
```

```
                35                  40                  45
Gly Lys Met Asn Ala Thr Ile Tyr Glu Leu Lys Glu Asp Lys Ser Tyr
             50                  55                  60

Asn Val Thr Asp Val Arg Phe Ile Met Lys Lys Cys His Tyr Tyr Ile
 65                  70                  75                  80

Glu Thr Phe Val Pro Gly Ser Gln Pro Gly Phe Thr Leu Gly Ile
                 85                  90                  95

Ile Lys Ser Asn Pro Gly Thr Thr Ser Gln Leu Val Arg Val Val Ser
                100                 105                 110

Thr Asn Tyr Asn Gln His Ala Met Val Phe Phe Lys Ile Val Arg Gln
            115                 120                 125

Asn Arg Glu Met Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 21
<211> LENGTH: 178
<212> TYPE: PRT
<213> ORGANISM: Artificial Sequence
<220> FEATURE:
<223> OTHER INFORMATION: NGAL mutein Pvd type II binder 3

<400> SEQUENCE: 21

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Ile Ala Gly Asn Thr Val Leu Arg Glu Asp Lys Asp Pro
            35                  40                  45

Gly Lys Met Pro Ala Thr Ile Tyr Glu Leu Lys Glu Asp Lys Ser Tyr
         50                  55                  60

Asn Val Thr Glu Val Arg Phe Ala Pro Lys Lys Cys Ile Tyr Ser Ile
 65                  70                  75                  80

Ser Thr Phe Val Pro Gly Ser Gln Pro Gly Glu Phe Thr Leu Gly Met
                 85                  90                  95

Ile Lys Ser Ser Pro Gly Gly Thr Ser Ala Leu Val Arg Val Val Ser
                100                 105                 110

Thr Asn Tyr Asn Gln His Ala Met Val Phe Phe Lys Lys Val Ser Gln
            115                 120                 125

Asn Arg Glu Val Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 22
<211> LENGTH: 178
<212> TYPE: PRT
<213> ORGANISM: Artificial Sequence
<220> FEATURE:

<223> OTHER INFORMATION: NGAL mutein Pvd type II binder 4

<400> SEQUENCE: 22

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Asn Ile Leu Arg Glu Asp Lys Asp Pro
        35                  40                  45

Ala Lys Met Pro Ala Thr Ile Tyr Glu Leu Lys Glu Asp Lys Ser Tyr
    50                  55                  60

Asn Val Thr Glu Val Arg Phe Ser Gln Lys Lys Cys Met Tyr Ala Ile
65                  70                  75                  80

Tyr Thr Phe Val Pro Gly Ser Gln Pro Gly Glu Phe Thr Leu Gly Arg
                85                  90                  95

Ile Lys Ser Pro Pro Gly Thr Thr Ser Ile Leu Val Arg Val Val Ser
            100                 105                 110

Thr Asn Tyr Asn Gln His Ala Met Val Phe Phe Lys Lys Val Met Gln
        115                 120                 125

Asn Arg Glu Phe Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 23
<211> LENGTH: 178
<212> TYPE: PRT
<213> ORGANISM: Artificial Sequence
<220> FEATURE:
<223> OTHER INFORMATION: NGAL mutein Pvd type II binder 5

<400> SEQUENCE: 23

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn His Ile Leu Arg Glu Asp Lys Asp Pro
        35                  40                  45

Ala Lys Met Pro Ala Thr Ile Tyr Glu Leu Lys Glu Asp Lys Ser Tyr
    50                  55                  60

Asn Val Thr Glu Val Arg Phe Gly Arg Lys Lys Cys His Tyr Trp Ile
65                  70                  75                  80

Glu Thr Phe Val Pro Gly Ser Gln Pro Gly Glu Phe Thr Leu Gly Arg
                85                  90                  95

Ile Lys Ser Asp Pro Gly Met Thr Ser Phe Leu Val Arg Val Val Ser
            100                 105                 110

Thr Asn Tyr Asn Gln His Ala Met Val Phe Phe Lys Ala Val Asp Gln
        115                 120                 125

Asn Arg Glu Asn Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 24
<211> LENGTH: 178
<212> TYPE: PRT
<213> ORGANISM: Artificial Sequence
<220> FEATURE:
<223> OTHER INFORMATION: NGAL mutein Pvd type II binder 6

<400> SEQUENCE: 24

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Asn Ala Gly Asn Gly Arg Leu Arg Glu Asp Lys Asp Pro
        35                  40                  45

Pro Lys Met Trp Ala Thr Ile Tyr Glu Leu Lys Glu Asp Lys Ser Tyr
    50                  55                  60

Asn Val Thr Arg Val Trp Phe Asn Gln Lys Lys Cys Lys Tyr Asp Ile
65                  70                  75                  80

Glu Thr Phe Val Pro Gly Ser Gln Pro Gly Glu Phe Thr Leu Gly Asp
                85                  90                  95

Ile Lys Ser Thr Pro Gly Trp Thr Ser Asn Leu Val Arg Val Val Ser
            100                 105                 110

Thr Asn Tyr Asn Gln His Ala Met Val Phe Phe Lys Asn Val Met Gln
        115                 120                 125

Asn Arg Glu Ile Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 25
<211> LENGTH: 178
<212> TYPE: PRT
<213> ORGANISM: Artificial Sequence
<220> FEATURE:
<223> OTHER INFORMATION: NGAL mutein Pvd type II binder 7

<400> SEQUENCE: 25

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Thr Leu Arg Glu Asp Lys Asp Pro
        35                  40                  45

Gly Lys Met Gly Ala Thr Ile Tyr Glu Leu Lys Glu Asp Lys Ser Tyr
    50                  55                  60

Asn Val Thr Glu Val Arg Phe Gly Arg Lys Lys Cys Gly Tyr Trp Ile
65                  70                  75                  80

Glu Thr Phe Val Pro Gly Ser Gln Pro Gly Glu Phe Thr Leu Gly Ala
                85                  90                  95

Ile Lys Ser Trp Pro Gly Ile Thr Ser Gly Leu Val Arg Val Val Ser

```
                    100                 105                 110
Thr Asn Tyr Asn Gln His Ala Met Val Phe Phe Lys Lys Val Asn Gln
            115                 120                 125

Asn Arg Glu Val Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 26
<211> LENGTH: 178
<212> TYPE: PRT
<213> ORGANISM: Artificial Sequence
<220> FEATURE:
<223> OTHER INFORMATION: NGAL mutein Pvd type II binder 8

<400> SEQUENCE: 26

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Glu Val Leu Arg Asp Asp Lys Asp Pro
        35                  40                  45

Gly Lys Met Pro Ala Thr Ile Tyr Glu Leu Lys Glu Asp Lys Ser Tyr
    50                  55                  60

Asn Val Thr Glu Val Arg Phe His Asn Lys Lys Cys Asn Tyr Ser Ile
65                  70                  75                  80

Glu Thr Phe Val Pro Gly Ser Gln Pro Gly Glu Phe Thr Leu Gly Lys
                85                  90                  95

Ile Lys Ser Asn Pro Gly Val Thr Ser Met Leu Val Arg Val Val Ser
            100                 105                 110

Thr Asn Tyr Asn Gln His Ala Met Val Phe Phe Lys Asn Val Lys Gln
        115                 120                 125

Asn Arg Glu Gly Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 27
<211> LENGTH: 178
<212> TYPE: PRT
<213> ORGANISM: Artificial Sequence
<220> FEATURE:
<223> OTHER INFORMATION: NGAL mutein Pvd type II binder 9

<400> SEQUENCE: 27

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Val Leu Arg Asp Asp Lys Asp Pro
        35                  40                  45
```

```
Gly Lys Met Pro Ala Thr Ile Tyr Glu Leu Lys Glu Asp Lys Ser Tyr
            50                  55                  60

Asn Val Thr Glu Val Arg Phe His Asn Lys Lys Cys Asn Tyr Ser Ile
 65                  70                  75                  80

Glu Thr Phe Val Pro Gly Ser Gln Pro Gly Glu Phe Thr Leu Gly Asn
                85                  90                  95

Ile Lys Ser Tyr Pro Gly Gln Thr Ser Met Leu Val Arg Val Val Ser
                100                 105                 110

Thr Asn Tyr Asn Gln His Ala Met Val Phe Phe Lys Lys Val Lys Gln
                115                 120                 125

Asn Arg Glu Val Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 28
<211> LENGTH: 178
<212> TYPE: PRT
<213> ORGANISM: Artificial Sequence
<220> FEATURE:
<223> OTHER INFORMATION: NGAL mutein Pvd type II binder 10

<400> SEQUENCE: 28

```
Gln Asp Ser Thr Ser Asp Leu Ile Pro Ala Pro Pro Leu Ser Lys Val
 1                   5                  10                  15

Pro Leu Gln Gln Asn Phe Gln Asp Asn Gln Phe His Gly Lys Trp Tyr
                20                  25                  30

Val Val Gly Val Ala Gly Asn Thr Val Leu Arg Asp Asp Lys Asp Pro
            35                  40                  45

Gly Lys Met Pro Ala Thr Ile Tyr Glu Leu Lys Glu Asp Lys Ser Tyr
            50                  55                  60

Asn Val Thr Glu Val Arg Phe His Lys Lys Cys Asn Tyr Phe Ile
 65                  70                  75                  80

Glu Thr Phe Val Pro Gly Ser Gln Pro Gly Glu Phe Thr Leu Gly Lys
                85                  90                  95

Ile Lys Ser His Pro Gly Gln Thr Ser Met Leu Val Arg Val Val Ser
                100                 105                 110

Thr Asn Tyr Asn Gln His Ala Met Val Phe Phe Lys Lys Val Lys Gln
                115                 120                 125

Asn Arg Glu Ala Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 29
<211> LENGTH: 178
<212> TYPE: PRT
<213> ORGANISM: Artificial Sequence
<220> FEATURE:
<223> OTHER INFORMATION: NGAL mutein Pvd type II binder 11

<400> SEQUENCE: 29

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Gln Val Leu Arg Asp Asp Lys Asp Pro
            35                  40                  45

Gly Lys Met Pro Ala Thr Ile Tyr Glu Leu Lys Glu Asp Lys Ser Tyr
    50                  55                  60

Asn Val Thr Glu Val Arg Phe His Asn Lys Lys Cys Asn Tyr Trp Ile
65                  70                  75                  80

Glu Thr Phe Val Pro Gly Ser Gln Pro Gly Glu Phe Thr Leu Gly Asn
                85                  90                  95

Ile Lys Ser Asn Pro Gly His Thr Ser Met Leu Val Arg Val Val Ser
            100                 105                 110

Thr Asn Tyr Asn Gln His Ala Met Val Phe Phe Lys Lys Val Lys Gln
        115                 120                 125

Asn Arg Glu Gly Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 30
<211> LENGTH: 178
<212> TYPE: PRT
<213> ORGANISM: Artificial Sequence
<220> FEATURE:
<223> OTHER INFORMATION: NGAL mutein Pvd type II binder 12

<400> SEQUENCE: 30

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Thr Ile Leu Arg Glu Asp Lys Asp Pro
            35                  40                  45

Gly Lys Met Asn Ala Thr Ile Tyr Glu Leu Lys Glu Asp Lys Ser Tyr
    50                  55                  60

Asn Val Thr Asp Val Arg Phe Ile Phe Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Met Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
```

```
                165                 170                 175
Asp Gly

<210> SEQ ID NO 31
<211> LENGTH: 178
<212> TYPE: PRT
<213> ORGANISM: Artificial Sequence
<220> FEATURE:
<223> OTHER INFORMATION: NGAL mutein Pvd type II binder 13

<400> SEQUENCE: 31

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Thr Ile Tyr Glu Leu Lys Glu Asp Lys Ser Tyr
    50                  55                  60

Asn Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
        115                 120                 125

Asn Arg Glu Ile Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 32
<211> LENGTH: 178
<212> TYPE: PRT
<213> ORGANISM: Artificial Sequence
<220> FEATURE:
<223> OTHER INFORMATION: NGAL mutein Pvd type II binder 14

<400> SEQUENCE: 32

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Glu Val Leu Arg Asp Asp Lys Asp Pro
        35                  40                  45

Gly Lys Met Pro Ala Thr Ile Tyr Glu Leu Lys Glu Asp Lys Ser Tyr
    50                  55                  60

Asp Val Thr Glu Val Arg Phe His Asn Lys Lys Cys Asn Tyr Phe Ile
65                  70                  75                  80

Glu Thr Phe Val Pro Gly Ser Gln Pro Gly Glu Phe Thr Leu Gly Lys
                85                  90                  95

Ile Lys Ser Asn Pro Gly Val Thr Ser Met Leu Val Arg Val Val Ser
            100                 105                 110
```

Thr Asn Tyr Asn Gln His Ala Met Val Phe Phe Lys Asn Val Lys Gln
            115                 120                 125

Asn Arg Glu Gly Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 33
<211> LENGTH: 178
<212> TYPE: PRT
<213> ORGANISM: Artificial Sequence
<220> FEATURE:
<223> OTHER INFORMATION: NGAL mutein Pvd type II binder 15

<400> SEQUENCE: 33

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Glu Val Leu Arg Asp Asp Lys Asp Pro
        35                  40                  45

Gly Lys Met Pro Ala Thr Ile Tyr Glu Leu Lys Glu Asp Lys Ser Tyr
    50                  55                  60

Gln Val Thr Glu Val Arg Phe His Asn Lys Lys Cys Asn Tyr Phe Ile
65                  70                  75                  80

Glu Thr Phe Val Pro Gly Ser Gln Pro Gly Glu Phe Thr Leu Gly Lys
                85                  90                  95

Ile Lys Ser Asn Pro Gly Val Thr Ser Met Leu Val Arg Val Val Ser
            100                 105                 110

Thr Asn Tyr Asn Gln His Ala Met Val Phe Phe Lys Asn Val Lys Gln
        115                 120                 125

Asn Arg Glu Gly Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 34
<211> LENGTH: 178
<212> TYPE: PRT
<213> ORGANISM: Artificial Sequence
<220> FEATURE:
<223> OTHER INFORMATION: NGAL mutein Pvd type II binder 16

<400> SEQUENCE: 34

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

```
Gly Lys Met Asn Ala Ala Ile Tyr Glu Leu Lys Glu Asp Lys Ser Tyr
 50                  55                  60

Asp Val Thr Asp Val Arg Phe Ile Arg Lys Lys Cys His Tyr Tyr Ile
 65                  70                  75                  80

Asp Thr Phe Val Pro Gly Ser Gln Pro Gly Glu Phe Thr Leu Gly Asn
                 85                  90                  95

Ile Lys Ser Tyr Pro Gly Thr Thr Ser Gln Leu Val Arg Val Val Ser
                100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 35
<211> LENGTH: 178
<212> TYPE: PRT
<213> ORGANISM: Artificial Sequence
<220> FEATURE:
<223> OTHER INFORMATION: NGAL mutein Pvd type II binder 17

<400> SEQUENCE: 35

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Val Gly Val Ala Gly Asn Thr Ile Leu Arg Glu Asp Lys Asp Pro
             35                  40                  45

Gly Lys Met Asn Ala Ala Ile Tyr Glu Leu Lys Glu Asp Lys Ser Tyr
 50                  55                  60

Gln Val Thr Asp Val Arg Phe Ile Arg Lys Lys Cys His Tyr Tyr Ile
 65                  70                  75                  80

Asp Thr Phe Val Pro Gly Ser Gln Pro Gly Glu Phe Thr Leu Gly Asn
                 85                  90                  95

Ile Lys Ser Tyr Pro Gly Thr Thr Ser Gln Leu Val Arg Val Val Ser
                100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 36
<211> LENGTH: 178
<212> TYPE: PRT
<213> ORGANISM: Artificial Sequence
<220> FEATURE:
<223> OTHER INFORMATION: NGAL mutein Pvd type II binder 18
```

```
<400> SEQUENCE: 36

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Ala Ile Tyr Glu Leu Lys Glu Asp Lys Ser Tyr
    50                  55                  60

Asp Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 37
<211> LENGTH: 178
<212> TYPE: PRT
<213> ORGANISM: Artificial Sequence
<220> FEATURE:
<223> OTHER INFORMATION: NGAL mutein Pvd type II binder 19

<400> SEQUENCE: 37

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Thr Ile Leu Arg Glu Asp Lys Asp Pro
        35                  40                  45

Gly Lys Met Asn Ala Thr Ile Tyr Glu Leu Lys Glu Asp Lys Ser Tyr
    50                  55                  60

Gln Val Thr Asp Val Arg Phe Ile Arg Lys Lys Cys His Tyr Tyr Ile
65                  70                  75                  80

Asp Thr Phe Val Pro Gly Ser Gln Pro Gly Glu Phe Thr Leu Gly Asn
                85                  90                  95

Ile Lys Ser Tyr Pro Gly Thr Thr Ser Gln Leu Val Arg Val Val Ser
            100                 105                 110

Thr Asn Tyr Asn Gln His Ala Met Val Phe Phe Lys Ile Val Arg Gln
            115                 120                 125

Asn Arg Glu Ile Phe Trp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

Asp Gly

<210> SEQ ID NO 38
<211> LENGTH: 178
<212> TYPE: PRT
<213> ORGANISM: Artificial Sequence
<220> FEATURE:
<223> OTHER INFORMATION: NGAL mutein Pvd type III binder 1

<400> SEQUENCE: 38

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Phe Ala Gly Asn Trp Met Leu Arg Glu Asp Lys Asp Pro
        35                  40                  45

His Lys Met Asn Ala Thr Ile Tyr Glu Leu Lys Glu Asp Lys Ser Tyr
    50                  55                  60

Asn Val Thr Glu Val Lys Phe Gln Ala Lys Lys Cys Ile Tyr Ser Ile
65                  70                  75                  80

His Thr Phe Val Pro Gly Ser Gln Pro Gly Glu Phe Thr Leu Gly Ile
                85                  90                  95

Ile Lys Ser Asn Pro Gly Gly Thr Ser Glu Leu Val Arg Val Val Ser
            100                 105                 110

Thr Asn Tyr Asn Gln His Ala Met Val Phe Phe Lys Trp Val His Gln
        115                 120                 125

Asn Arg Glu Phe Phe Gln Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 39
<211> LENGTH: 178
<212> TYPE: PRT
<213> ORGANISM: Artificial Sequence
<220> FEATURE:
<223> OTHER INFORMATION: NGAL mutein Pvd type III binder 2

<400> SEQUENCE: 39

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Phe Ala Gly Asn Arg Trp Leu Arg Glu Asp Lys Asp Pro
        35                  40                  45

Ile Lys Met Tyr Ala Thr Ile Tyr Glu Leu Lys Glu Asp Lys Ser Tyr
    50                  55                  60

Asn Val Thr Gln Val Asn Phe Trp Leu Lys Lys Cys Ala Tyr Ser Ile
65                  70                  75                  80

Ser Thr Phe Val Pro Gly Ser Gln Pro Gly Glu Phe Thr Leu Gly Arg
                85                  90                  95

Ile Lys Ser Ile Pro Gly Pro Thr Ser Glu Leu Val Arg Val Val Ser
            100                 105                 110
```

```
Thr Asn Tyr Asn Gln His Ala Met Val Phe Phe Lys Thr Val Ile Gln
            115                 120                 125

Asn Arg Glu Phe Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 40
<211> LENGTH: 178
<212> TYPE: PRT
<213> ORGANISM: Artificial Sequence
<220> FEATURE:
<223> OTHER INFORMATION: NGAL mutein Pvd type III binder 2

<400> SEQUENCE: 40

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Phe Ala Gly Asn Leu Leu Leu Arg Glu Asp Lys Asp Pro
        35                  40                  45

Arg Lys Met Arg Ala Thr Ile Tyr Glu Leu Lys Glu Asp Lys Ser Tyr
    50                  55                  60

Asn Val Thr Asp Val Arg Phe Leu Tyr Lys Lys Cys Ile Tyr Ser Ile
65                  70                  75                  80

Ala Thr Phe Val Pro Gly Ser Gln Pro Gly Glu Phe Thr Leu Gly Gly
                85                  90                  95

Ile Lys Ser Ala Pro Gly Phe Thr Ser Glu Leu Val Arg Val Val Ser
            100                 105                 110

Thr Asn Tyr Asn Gln His Ala Met Val Phe Phe Lys Trp Val Ala Gln
            115                 120                 125

Asn Arg Glu Tyr Phe Glu Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 41
<211> LENGTH: 178
<212> TYPE: PRT
<213> ORGANISM: Artificial Sequence
<220> FEATURE:
<223> OTHER INFORMATION: NGAL mutein Pvd type III binder 4

<400> SEQUENCE: 41

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Phe Ala Gly Asn Trp Arg Leu Arg Glu Asp Lys Asp Pro
        35                  40                  45

Pro Lys Met Ser Ala Thr Ile Tyr Glu Leu Lys Glu Asp Lys Ser Tyr
```

```
                  50                  55                  60

Asn Val Thr Asn Val Arg Phe Trp Pro Lys Lys Cys Arg Tyr Ser Ile
 65                  70                  75                  80

Ser Thr Phe Val Pro Gly Ser Gln Pro Gly Glu Phe Thr Leu Gly Met
                     85                  90                  95

Ile Lys Ser Pro Pro Gly Gly Thr Ser Glu Leu Val Arg Val Val Ser
                    100                 105                 110

Thr Asn Tyr Asn Gln His Ala Met Val Phe Phe Lys Trp Val Phe Gln
                    115                 120                 125

Asn Arg Glu Phe Phe Glu Ile Thr Leu Tyr Gly Arg Thr Lys Glu Leu
                    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 42
<211> LENGTH: 178
<212> TYPE: PRT
<213> ORGANISM: Artificial Sequence
<220> FEATURE:
<223> OTHER INFORMATION: NGAL mutein Pvd type III binder 5

<400> SEQUENCE: 42

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                    20                  25                  30

Val Val Gly Glu Ala Gly Asn Leu Ala Leu Arg Glu Asp Lys Asp Pro
                    35                  40                  45

Lys Lys Met Met Ala Thr Ile Tyr Glu Leu Lys Glu Asp Lys Ser Tyr
 50                  55                  60

Asn Val Thr Glu Val Arg Phe Arg His Lys Lys Cys Gln Tyr Asp Ile
 65                  70                  75                  80

Ala Thr Phe Val Pro Gly Ser Gln Pro Gly Glu Phe Thr Leu Gly Leu
                     85                  90                  95

Ile Lys Ser Asp Pro Gly Gln Thr Ser Glu Leu Val Arg Val Val Ser
                    100                 105                 110

Thr Asn Tyr Asn Gln His Ala Met Val Phe Phe Lys Lys Val Val Gln
                    115                 120                 125

Asn Arg Glu Phe Phe Trp Ile Thr Leu Tyr Gly Arg Thr Lys Glu Leu
                    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 43
<211> LENGTH: 178
<212> TYPE: PRT
<213> ORGANISM: Artificial Sequence
<220> FEATURE:
<223> OTHER INFORMATION: NGAL mutein Pvd type III binder 6

<400> SEQUENCE: 43
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ala Leu Arg Glu Asp Lys Asp Pro
            35                  40                  45

Met Lys Met Met Ala Thr Ile Tyr Glu Leu Lys Glu Asp Lys Ser Tyr
 50                  55                  60

Asn Val Thr Glu Val Arg Phe Arg Gln Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Ser Glu Leu Val Arg Val Val Ser
                100                 105                 110

Thr Asn Tyr Asn Gln His Ala Met Val Phe Phe Lys Lys Val Val Gln
            115                 120                 125

Asn Arg Glu Tyr Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 44
<211> LENGTH: 178
<212> TYPE: PRT
<213> ORGANISM: Artificial Sequence
<220> FEATURE:
<223> OTHER INFORMATION: NGAL mutein Pvd type III binder 7

<400> SEQUENCE: 44

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Thr Leu Arg Glu Asp Lys Asp Pro
            35                  40                  45

Met Lys Met Met Ala Thr Ile Tyr Glu Leu Lys Glu Asp Lys Ser Tyr
 50                  55                  60

Asn Val Thr Glu Val Arg Phe Arg Arg Lys Lys Cys Lys Tyr Asp Ile
65                  70                  75                  80

Val Thr Phe Val Pro Gly Ser Gln Pro Gly Glu Phe Thr Leu Gly Val
                85                  90                  95

Ile Lys Ser Asp Pro Gly Gln Thr Ser Glu Leu Val Arg Val Val Ser
                100                 105                 110

Thr Asn Tyr Asn Gln His Ala Met Val Phe Phe Lys Lys Val Val Gln
            115                 120                 125

Asn Arg Glu Tyr Phe Trp Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 45
<211> LENGTH: 178
<212> TYPE: PRT
<213> ORGANISM: Artificial Sequence
<220> FEATURE:
<223> OTHER INFORMATION: NGAL mutein Pvd type III binder 8

<400> SEQUENCE: 45

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ala Leu Arg Glu Asp Lys Asp Pro
        35                  40                  45

Met Lys Met Met Ala Thr Ile Tyr Glu Leu Lys Glu Asp Lys Ser Tyr
    50                  55                  60

Asn Val Thr Glu Val Arg Phe Arg His Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Ser Glu Leu Val Arg Val Val Ser
            100                 105                 110

Thr Asn Tyr Asn Gln His Ala Met Val Phe Phe Lys Lys Val Val Gln
        115                 120                 125

Asn Arg Glu Tyr Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 46
<211> LENGTH: 174
<212> TYPE: PRT
<213> ORGANISM: Artificial Sequence
<220> FEATURE:
<223> OTHER INFORMATION: NGAL mutein Pvd type III binder 9

<400> SEQUENCE: 46

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ala Leu Arg Glu Asp Lys Asp Pro
        35                  40                  45

Lys Lys Met Met Ala Thr Ile Tyr Glu Leu Lys Glu Asp Lys Ser Tyr
    50                  55                  60

Asn Val Thr Glu Val Arg Phe Arg Tyr Lys Lys Cys Gln Tyr Asp Ile
65                  70                  75                  80

Val Thr Phe Val Pro Gly Ser Gln Pro Gly Phe Thr Leu Ser Glu
                85                  90                  95

Pro Gly Gln Thr Ser Glu Leu Val Arg Val Val Ser Thr Asn Tyr Asn
            100                 105                 110

Gln His Ala Met Val Phe Phe Lys Lys Val Gln Asn Arg Glu Phe
```

```
                    115                 120                 125
Phe Trp Ile Thr Leu Tyr Gly Arg Thr Lys Glu Leu Thr Ser Glu Leu
            130                 135                 140
Lys Glu Asn Phe Ile Arg Phe Ser Lys Ser Leu Gly Leu Pro Glu Asn
145                 150                 155                 160
His Ile Val Phe Pro Val Pro Ile Asp Gln Cys Ile Asp Gly
                165                 170

<210> SEQ ID NO 47
<211> LENGTH: 178
<212> TYPE: PRT
<213> ORGANISM: Artificial Sequence
<220> FEATURE:
<223> OTHER INFORMATION: NGAL mutein Pvd type III binder 10

<400> SEQUENCE: 47

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Glu Ala Gly Asn Leu Ala Arg Arg Glu Asp Lys Asp Pro
        35                  40                  45
Met Lys Met Met Ala Thr Ile Tyr Glu Leu Lys Glu Asp Lys Ser Tyr
    50                  55                  60
Asn Val Thr Glu Val Arg Phe Arg His Lys Lys Cys Lys Tyr Asp Ile
65                  70                  75                  80
Val Thr Phe Val Pro Gly Ser Gln Pro Gly Glu Phe Thr Leu Gly Leu
                85                  90                  95
Ile Lys Ser Asp Pro Gly Gln Thr Pro Glu Leu Val Arg Val Val Ser
            100                 105                 110
Thr Asn Tyr Asn Gln His Ala Met Val Phe Phe Lys Lys Val Val Gln
        115                 120                 125
Asn Arg Glu Tyr Phe Trp Ile Thr Leu Tyr Gly Arg Thr Lys Glu Leu
    130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly

<210> SEQ ID NO 48
<211> LENGTH: 178
<212> TYPE: PRT
<213> ORGANISM: Artificial Sequence
<220> FEATURE:
<223> OTHER INFORMATION: NGAL mutein Pvd type III binder 11

<400> SEQUENCE: 48

Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
            20                  25                  30
Val Val Gly Glu Ala Gly Asn Leu Ala Leu Arg Glu Asp Lys Asn Pro
        35                  40                  45
Met Lys Met Met Ala Thr Ile Tyr Glu Leu Lys Glu Asp Lys Ser Tyr
    50                  55                  60
Asn Val Thr Glu Val Arg Phe Arg His Lys Lys Cys Lys Tyr Asp Ile
```

65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
                100                 105                 110

Thr Asn Tyr Asn Gln His Ala Met Val Phe Phe Lys Lys Val Val Gln
                115                 120                 125

Asn Arg Glu Tyr Phe Trp Ile Thr Leu Tyr Gly Arg Thr Lys Glu Leu
    130                 135                 140

Pro Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 49
<211> LENGTH: 178
<212> TYPE: PRT
<213> ORGANISM: Artificial Sequence
<220> FEATURE:
<223> OTHER INFORMATION: NGAL mutein Pvd type III binder 12

<400> SEQUENCE: 49

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Glu Ala Gly Asn Leu Ala Leu Arg Glu Gly Arg Asp Pro
                35                  40                  45

Met Lys Met Met Ala Thr Ile Tyr Glu Leu Lys Glu Asp Lys Ser Tyr
    50                  55                  60

Asn Val Thr Glu Val Arg Phe Arg His Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
                100                 105                 110

Thr Asn Tyr Asn Gln His Ala Met Val Phe Phe Lys Lys Val Val Gln
                115                 120                 125

Asn Arg Glu Tyr Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 50
<211> LENGTH: 178
<212> TYPE: PRT
<213> ORGANISM: Artificial Sequence
<220> FEATURE:
<223> OTHER INFORMATION: NGAL mutein Pvd type III binder 13

<400> SEQUENCE: 50

Gln Asp Ser Thr Ser Asp Leu Ile Pro Ala Pro Pro Leu Ser Lys Val
1               5                   10                  15

```
Pro Leu Gln Gln Asn Phe Gln Asp Asn Gln Phe His Gly Lys Trp Tyr
            20                  25                  30

Val Val Gly Glu Ala Gly Asn Leu Ala Arg Arg Glu Asp Lys Asp Pro
        35                  40                  45

Met Lys Met Met Ala Thr Ile Tyr Glu Leu Lys Glu Asp Lys Ser Tyr
50                  55                  60

Asp Val Thr Glu Val Arg Phe Arg His Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
                100                 105                 110

Thr Asn Tyr Asn Gln His Ala Met Val Phe Phe Lys Lys Val Val Gln
                115                 120                 125

Asn Arg Glu Tyr Phe Trp Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 51
<211> LENGTH: 178
<212> TYPE: PRT
<213> ORGANISM: Artificial Sequence
<220> FEATURE:
<223> OTHER INFORMATION: NGAL mutein Pvd type III binder 14

<400> SEQUENCE: 51

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ala Leu Arg Glu Asp Lys Asn Pro
        35                  40                  45

Met Lys Met Met Ala Thr Ile Tyr Glu Leu Lys Glu Asp Lys Ser Tyr
50                  55                  60

Asp Val Thr Glu Val Arg Phe Arg His Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
                100                 105                 110

Thr Asn Tyr Asn Gln His Ala Met Val Phe Phe Lys Lys Val Val Gln
                115                 120                 125

Asn Arg Glu Tyr Phe Trp Ile Thr Leu Tyr Gly Arg Thr Lys Glu Leu
            130                 135                 140

Pro Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

```
<210> SEQ ID NO 52
<211> LENGTH: 178
<212> TYPE: PRT
<213> ORGANISM: Artificial Sequence
<220> FEATURE:
<223> OTHER INFORMATION: NGAL mutein Pvd type III binder 15

<400> SEQUENCE: 52
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Glu Ala Gly Asn Leu Ala Leu Arg Glu Gly Arg Asp Pro
        35                  40                  45

Met Lys Met Met Ala Thr Ile Tyr Glu Leu Lys Glu Asp Lys Ser Tyr
    50                  55                  60

Asp Val Thr Glu Val Arg Phe Arg His Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
            100                 105                 110

Thr Asn Tyr Asn Gln His Ala Met Val Phe Phe Lys Lys Val Val Gln
        115                 120                 125

Asn Arg Glu Tyr Phe Trp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 53
<211> LENGTH: 178
<212> TYPE: PRT
<213> ORGANISM: Artificial Sequence
<220> FEATURE:
<223> OTHER INFORMATION: NGAL mutein Pvd type III binder 16

<400> SEQUENCE: 53
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Glu Ala Gly Asn Leu Ala Arg Arg Glu Asp Lys Asp Pro
        35                  40                  45

Met Lys Met Met Ala Thr Ile Tyr Glu Leu Lys Glu Asp Lys Ser Tyr
    50                  55                  60

Asp Val Thr Glu Val Arg Phe Arg His Lys Lys Cys Lys Tyr Asp Ile
65                  70                  75                  80

Val Thr Phe Val Pro Gly Ser Gln Pro Gly Glu Phe Thr Leu Gly Leu
                85                  90                  95

Ile Lys Ser Asp Pro Gly Gln Thr Pro Glu Leu Val Arg Val Val Ser
            100                 105                 110

Thr Asn Tyr Asn Gln His Ala Met Val Phe Phe Lys Lys Val Val Gln
        115                 120                 125

Asn Arg Glu Tyr Phe Trp Ile Thr Leu Tyr Gly Arg Thr Lys Glu Leu

```
                    130                 135                 140
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 54
<211> LENGTH: 178
<212> TYPE: PRT
<213> ORGANISM: Artificial Sequence
<220> FEATURE:
<223> OTHER INFORMATION: NGAL mutein Pch binder 1

<400> SEQUENCE: 54

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ile Leu Leu Arg Glu Asp Lys Asp Pro
        35                  40                  45

His Lys Met Leu Ala Thr Ile Tyr Glu Leu Lys Glu Asp Lys Ser Tyr
    50                  55                  60

Asn Val Thr His Val Thr Phe Lys Trp Lys Lys Cys Tyr Tyr Ala Ile
65                  70                  75                  80

Arg Thr Phe Val Pro Gly Ser Gln Pro Gly Glu Phe Thr Leu Gly Met
                85                  90                  95

Ile Lys Ser Glu Pro Gly His Thr Ser Met Leu Val Arg Val Val Ser
            100                 105                 110

Thr Asn Tyr Asn Gln His Ala Met Val Phe Phe Lys Trp Val Asp Gln
        115                 120                 125

Asn Arg Glu Glu Phe Leu Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 55
<211> LENGTH: 178
<212> TYPE: PRT
<213> ORGANISM: Artificial Sequence
<220> FEATURE:
<223> OTHER INFORMATION: NGAL mutein Pch binder 2

<400> SEQUENCE: 55

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly His Ala Gly Asn Gln Trp Leu Arg Glu Asp Lys Asp Pro
        35                  40                  45

Arg Lys Met Trp Ala Thr Ile Tyr Glu Leu Lys Glu Asp Lys Ser Tyr
    50                  55                  60

Asn Val Thr Asp Val Asp Phe Ala Ile Lys Lys Cys His Tyr Arg Ile
65                  70                  75                  80
```

```
Thr Thr Phe Val Pro Gly Ser Gln Pro Gly Glu Phe Thr Leu Gly Asn
                85                  90                  95

Ile Lys Ser His Pro Gly Gly Thr Ser Gly Leu Val Arg Val Val Ser
            100                 105                 110

Thr Asn Tyr Asn Gln His Ala Met Val Phe Phe Lys Phe Val Ile Gln
            115                 120                 125

Asn Arg Glu Ala Phe Phe Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 56
<211> LENGTH: 178
<212> TYPE: PRT
<213> ORGANISM: Artificial Sequence
<220> FEATURE:
<223> OTHER INFORMATION: NGAL mutein Pch binder 3

<400> SEQUENCE: 56

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Phe His Leu Arg Glu Asp Lys Asp Pro
        35                  40                  45

Ser Lys Met Pro Ala Thr Ile Tyr Glu Leu Lys Glu Asp Lys Ser Tyr
    50                  55                  60

Asn Val Thr His Val Pro Phe Trp Ala Lys Lys Cys Ala Tyr Lys Ile
65                  70                  75                  80

Ile Thr Phe Val Pro Gly Ser Gln Pro Gly Glu Phe Thr Leu Gly Ala
                85                  90                  95

Ile Lys Ser Gly Pro Gly Met Thr Ser Trp Leu Val Arg Val Val Ser
            100                 105                 110

Thr Asn Tyr Asn Gln His Ala Met Val Phe Phe Lys Gly Val Trp Gln
            115                 120                 125

Asn Arg Glu Thr Phe Val Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 57
<211> LENGTH: 178
<212> TYPE: PRT
<213> ORGANISM: Artificial Sequence
<220> FEATURE:
<223> OTHER INFORMATION: NGAL mutein Pch binder 4

<400> SEQUENCE: 57

```
Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe His Gly Lys Trp Tyr
            20                  25                  30

Val Val Gly Val Ala Gly Asn Tyr Trp Leu Arg Glu Asp Lys Asp Pro
        35                  40                  45

Ala Lys Met Tyr Ala Thr Ile Tyr Glu Leu Lys Glu Asp Lys Ser Tyr
 50                  55                  60

Asn Val Thr Asp Val Arg Phe Trp Arg Lys Lys Cys Arg Tyr Asp Ile
 65                  70                  75                  80

Trp Thr Phe Val Pro Gly Ser Gln Pro Gly Glu Phe Thr Leu Gly Pro
                85                  90                  95

Ile Lys Ser Glu Pro Gly Gln Thr Ser Arg Leu Val Arg Val Val Ser
                100                 105                 110

Thr Asn Tyr Asn Gln His Ala Met Val Phe Phe Lys Leu Val Arg Gln
                115                 120                 125

Asn Arg Glu Ala Phe Asn Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 58
<211> LENGTH: 178
<212> TYPE: PRT
<213> ORGANISM: Artificial Sequence
<220> FEATURE:
<223> OTHER INFORMATION: NGAL mutein Pch binder 5

<400> SEQUENCE: 58

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Leu Gly Met Ala Gly Asn Phe His Leu Arg Glu Asp Lys Asp Pro
        35                  40                  45

Ser Lys Met Pro Ala Thr Ile Tyr Glu Leu Lys Glu Asp Lys Ser Tyr
 50                  55                  60

Asn Val Thr His Val Pro Phe Trp Ala Lys Lys Cys Ala Tyr Lys Thr
 65                  70                  75                  80

Ile Thr Phe Val Pro Gly Ser Gln Pro Gly Glu Phe Thr Leu Gly Ala
                85                  90                  95

Ile Lys Ser Gly Pro Gly Met Thr Ser Trp Leu Val Arg Val Val Ser
                100                 105                 110

Thr Asn Tyr Asn Gln His Ala Met Val Phe Ser Lys Gly Val Trp Gln
                115                 120                 125

Asn Arg Glu Thr Phe Val Ile Thr Leu Tyr Gly Arg Ala Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 59

```
<211> LENGTH: 178
<212> TYPE: PRT
<213> ORGANISM: Artificial Sequence
<220> FEATURE:
<223> OTHER INFORMATION: NGAL mutein Pch binder 6

<400> SEQUENCE: 59

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Phe His Leu Arg Glu Asp Lys Asp Pro
        35                  40                  45

Ser Lys Met Pro Ala Thr Ile Tyr Glu Leu Lys Glu Asp Lys Ser Tyr
    50                  55                  60

Asn Val Thr His Val Pro Phe Trp Ala Lys Lys Cys Ala Tyr Lys Thr
65                  70                  75                  80

Ile Thr Phe Val Pro Gly Ser Gln Pro Gly Glu Phe Thr Leu Gly Ala
                85                  90                  95

Ile Lys Ser Gly Pro Gly Met Thr Ser Trp Leu Val Arg Val Val Ser
            100                 105                 110

Thr Asn Tyr Asn Gln His Ala Met Val Phe Ser Lys Gly Val Trp Gln
        115                 120                 125

Asn Arg Glu Thr Phe Val Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 60
<211> LENGTH: 178
<212> TYPE: PRT
<213> ORGANISM: Artificial Sequence
<220> FEATURE:
<223> OTHER INFORMATION: NGAL mutein Pch binder 7

<400> SEQUENCE: 60

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly His Ala Gly Asn Gln Trp Leu Arg Glu Gly Arg Asp Pro
        35                  40                  45

Arg Lys Met Trp Ala Thr Ile Tyr Glu Leu Lys Glu Asp Lys Ser Tyr
    50                  55                  60

Asn Val Thr Asp Val Asp Phe Ala Ile Lys Lys Cys Leu Tyr Arg Ile
65                  70                  75                  80

Thr Thr Phe Val Pro Gly Ser Gln Pro Gly Glu Phe Thr Leu Gly Asn
                85                  90                  95

Ile Lys Ser His Pro Gly Gly Thr Ser Gly Leu Val Arg Val Val Ser
            100                 105                 110

Thr Asn Tyr Asn Gln His Ala Met Val Phe Phe Lys Phe Val Ile Gln
        115                 120                 125

Asn Arg Glu Ala Phe Phe Ile Thr Leu Tyr Gly Arg Thr Lys Glu Leu
    130                 135                 140
```

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 61
<211> LENGTH: 178
<212> TYPE: PRT
<213> ORGANISM: Artificial Sequence
<220> FEATURE:
<223> OTHER INFORMATION: NGAL mutein Pch binder 8

<400> SEQUENCE: 61

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly His Ala Gly Asn Gln Trp Leu Arg Gly Asp Tyr Asp Pro
        35                  40                  45

Arg Lys Met Trp Ala Thr Ile Tyr Glu Leu Lys Glu Asp Lys Ser Tyr
50                  55                  60

Asn Val Thr Asp Val Asp Phe Ala Ile Glu Lys Cys His Tyr Arg Ile
65                  70                  75                  80

Thr Thr Phe Val Pro Gly Ser Gln Pro Gly Glu Phe Thr Phe Gly Asn
                85                  90                  95

Ile Lys Ser His Pro Gly Gly Thr Ser Gly Leu Ala Arg Val Val Ser
            100                 105                 110

Thr Asn Tyr Asn Gln His Ala Met Val Phe Phe Lys Phe Val Ile Gln
        115                 120                 125

Asn Arg Glu Ala Phe Phe Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 62
<211> LENGTH: 178
<212> TYPE: PRT
<213> ORGANISM: Artificial Sequence
<220> FEATURE:
<223> OTHER INFORMATION: NGAL mutein Pch binder 9

<400> SEQUENCE: 62

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly His Ala Gly Asn Gln Trp Leu Arg Glu Gly Arg Asp Pro
        35                  40                  45

Arg Lys Met Trp Ala Thr Ile Tyr Glu Leu Lys Glu Asp Lys Ser Tyr
50                  55                  60

Asp Val Thr Asp Val Asp Phe Ala Ile Lys Lys Cys Leu Tyr Arg Ile
65                  70                  75                  80
```

```
Thr Thr Phe Val Pro Gly Ser Gln Pro Gly Glu Phe Thr Leu Gly Asn
            85                  90                  95

Ile Lys Ser His Pro Gly Gly Thr Ser Gly Leu Val Arg Val Val Ser
            100                 105                 110

Thr Asn Tyr Asn Gln His Ala Met Val Phe Phe Lys Phe Val Ile Gln
            115                 120                 125

Asn Arg Glu Ala Phe Phe Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 63
<211> LENGTH: 178
<212> TYPE: PRT
<213> ORGANISM: Artificial Sequence
<220> FEATURE:
<223> OTHER INFORMATION: NGAL mutein Pch binder 10

<400> SEQUENCE: 63

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly His Ala Gly Asn Gln Trp Leu Arg Gly Asp Tyr Asp Pro
            35                  40                  45

Arg Lys Met Trp Ala Thr Ile Tyr Glu Leu Lys Glu Asp Lys Ser Tyr
50                  55                  60

Asp Val Thr Asp Val Asp Phe Ala Ile Glu Lys Cys His Tyr Arg Ile
65                  70                  75                  80

Thr Thr Phe Val Pro Gly Ser Gln Pro Gly Glu Phe Thr Phe Gly Asn
            85                  90                  95

Ile Lys Ser His Pro Gly Gly Thr Ser Gly Leu Ala Arg Val Val Ser
            100                 105                 110

Thr Asn Tyr Asn Gln His Ala Met Val Phe Phe Lys Phe Val Ile Gln
            115                 120                 125

Asn Arg Glu Ala Phe Phe Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                    165                 170                 175

Asp Gly

<210> SEQ ID NO 64
<211> LENGTH: 178
<212> TYPE: PRT
<213> ORGANISM: Artificial Sequence
<220> FEATURE:
<223> OTHER INFORMATION: Expressed protein amino acid sequence

<400> SEQUENCE: 64

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
```

```
            20                  25                  30
Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Cys Asp Tyr Trp Ile
65                  70                  75                  80

Arg Thr Phe Val Pro Gly Ser Gln Pro Gly Glu Phe Thr Leu Gly Asn
                    85                  90                  95

Ile Lys Ser Tyr Pro Gly Leu Thr Ser Tyr Leu Val Arg Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 65
<211> LENGTH: 534
<212> TYPE: DNA
<213> ORGANISM: Artificial Sequence
<220> FEATURE:
<223> OTHER INFORMATION: S0466.12C05

<400> SEQUENCE: 65
caggactcca cctcagacct gatcccagcc ccacctctga gcaaggtccc tctgcagcag    60
aacttccagg acaaccaatt ccatgggaaa tggtatgtcg tgggcaatgc cggaaatgga   120
tggctgcgtg aggataagga tccgatcaaa atgatggcga ccatttacga gttgaaagaa   180
gataaatcat ataacgtcac cgttgtgcaa ttttgggaca agaaatgcct gtaccaaatt   240
caaacctttg tgccggggag ccagccgggc gagtttactt taggccacat taaaagtaaa   300
ccgggccaca catcacactt ggtccgcgtc gtgagcacca actacaacca gcatgccatg   360
gtgttcttca gcgtgtgtg gcagaaccgc gagtggtttg acatcacact gtacgggcgc   420
acgaaagaac tgacaagcga gctgaaggaa aatttttatcc gcttttccaa atctctgggc   480
ctccctgaaa accacatcgt cttccctgtc ccaatcgacc agtgtatcga cggc          534

<210> SEQ ID NO 66
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 66
caggactcca cctcagacct gatcccagcc ccacctctga gcaaggtccc tctgcagcag    60
aacttccagg acaaccaatt ccatgggaaa tggtatgtcg tgggcaccgc cggaaatgga   120
ttcctgcgtg aggataagga tccgctgaaa atgtgggcga ccatttacga gttgaaagaa   180
gataaatcat ataacgtcac cagcgtgtgg tttgcactga gaaatgcta ctacgacatt    240 ggaacctttg tgccggggag ccagccgggc gagtttactt taggcatcat taaaagtgag   300
```

```
ccgggccaca catcacaatt ggtccgcgtc gtgagcacca actacaacca gcatgccatg    360
gtgttcttca agtgggtgaa tcagaaccgc gagaattttc aaatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 67
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 67

```
caggactcca cctcagacct gatcccagcc ccacctctga gcaaggtccc tctgcagcag     60
aacttccagg acaaccaatt ccatgggaaa tggtatgtcg tgggctgggc cggaaatacc    120
accctgcgtg aggataagga tccgcctaaa atgcctgcga ccatttacga gttgaaagaa    180
gataaatcat ataacgtcac cgacgtgcaa tttagcgaga gaaatgcag ctacagcatt     240 atcacctttg tgccggggag ccagccgggc gagtttactt taggcggaat taaaagtaat    300
ccgggcaaaa catcacactt ggtccgcgtc gtgagcacca actacaacca gcatgccatg    360
gtgttcttca agtacgtggc acagaaccgc gagggattta atatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 68
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 68

```
caggactcca cctcagacct gatcccagcc ccacctctga gcaaggtccc tctgcagcag     60
aacttccagg acaaccaatt ccatgggaaa tggtatgtcg tgggcttcgc cggaaataat    120
cgtctgcgtg aggataagga tccgcctaaa atgatggcga ccatttacga gttgaaagaa    180
gataaatcat ataacgtcac cgacgtgacc tttgaggcaa agaaatgccg ttaccgtatt    240
atcacctttg tgccggggag ccagccgggc gagtttactt taggctacat taaaagtaaa    300
ccgggcccta catcattctt ggtccgcgtc gtgagcacca actacaacca gcatgccatg    360
gtgttcttca agagcgtgac ccagaaccgc gagtggtttg aatcacact gtacgggcgc     420 acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 69
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 69

```
caggactcca cctcagacct gatcccagcc ccacctctga gcaaggtccc tctgcagcag     60
```

```
aacttccagg acaaccaatt ccatgggaaa tggtatgtcg tgggcctggc cggaaatgga      120
tggctgcgtg aggataagga tccggttaaa atgatggcga ccatttacga gttgaaagaa      180
gataaatcat ataacgtcac cgttgtggac tttgagctga agaaatgccg ttacatgatt      240
gagacctttg tgccggggag ccagccgggc gagtttactt taggcgacat taaaagtttc      300
ccgggctgga catcacaatt ggtccgcgtc gtgagcacca actacaacca gcatgccatg      360
gtgttcttca agggagtgta ccagaaccgc gagtggtttc acatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534

<210> SEQ ID NO 70
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 70
caggactcca cctcagacct gatcccagcc ccacctctga gcaaggtccc tctgcagcag      60
aacttccagg acaaccaatt ccatgggaaa tggtatgtcg tgggcgttgc cggaaatttc      120
ttcctgcgtg aggataagga tccggcaaaa atgcctgcga ccatttacga gttgaaagaa      180
gataaatcat ataacgtcac cgaggtgtgg tttctgaata agaaatgcca atacgagatt      240
cacacctttg tgccggggag ccagccgggc gagtttactt taggctacat taaaagttac      300
ccgggctaca catcacactt ggtccgcgtc gtgagcacca actacaacca gcatgccatg      360
gtgttcttca aggttgtgca ccagaaccgc gataaatttt ggatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534

<210> SEQ ID NO 71
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 71
caggactcca cctcagacct gatcccagcc ccacctctga gcaaggtccc tctgcagcag      60
aacttccagg acaaccaatt ccatgggaaa tggtatgtcg tgggctgggc cggaaatacg      120
acgctgcgtg aggataagga tccgcctaaa atgcctgcga ccatttacga gttgaaagaa      180
gataaatcat ataacgtcac cgatgtgcag tttcctgaga gaaatgcat ttactctact      240 attacctttg tgccggggag ccagccgggc gagtttactt taggcggtat taaaagtagt      300
ccgggccaga catcacattt ggtccgcgtc gtgagcacca actacaacca gcatgccatg      360
gtgttcttca agtatgtgat tcagaaccgc gaggggttta atatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534

<210> SEQ ID NO 72
<211> LENGTH: 534
<212> TYPE: DNA
```

<213> ORGANISM: Artificial Sequence
<220> FEATURE:
<223> OTHER INFORMATION: DNA encoding an expressed protein amino acid
      sequence

<400> SEQUENCE: 72

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggctgggc | cggaaatacg | 120 |
| acgctgcgtg | aggataagga | tccgcctaaa | atgcctgcga | ccatttacga | gttgaaagaa | 180 |
| gataaatcat | ataacgtcac | cgatgtgcag | tttccggata | agaaatgcat | ttactcgatt | 240 |
| attacctttg | tgccggggag | ccagccgggc | gagtttactt | taggcgggat | taaaagtaat | 300 |
| ccgggcgata | catcacattt | ggtccgcgtc | gtgagcacca | actacaacca | gcatgccatg | 360 |
| gtgttcttca | agtatgtggt | gcagaaccgc | gaggggtttta | atatcacact | gtacgggcgc | 420 |
| acgaaagaac | tgacaagcga | gctgaaggaa | aattttatcc | gcttttccaa | atctctgggc | 480 |
| ctccctgaaa | accacatcgt | cttccctgtc | ccaatcgacc | agtgtatcga | cggc | 534 |

<210> SEQ ID NO 73
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 73

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggctgggc | cggaaatacg | 120 |
| acgctgcgtg | aggataagga | tccgcctaaa | atgcctgcga | ccatttacga | gttgaaagaa | 180 |
| gataaatcat | ataacgtcac | cgatgtgcag | tttcctgaga | agaaatgcac | gtactcgatt | 240 |
| attacctttg | tgccggggag | ccagccgggc | gagtttactt | taggcgatat | taaaagtaat | 300 |
| ccgggcgaga | catcacattt | ggtccgcgtc | atgagcacca | actacaacca | gcatgccatg | 360 |
| gtgttcttca | agtatgtgga | tcagaaccgc | gagggggttta | atatcacact | gtacgggcgc | 420 |
| acgaaagaac | tgacaagcga | gctgaaggaa | aattttatcc | gcttttccaa | atctctgggc | 480 |
| ctccctgaaa | accacatcgt | cttccctgtc | ccaatcgacc | agtgtatcga | cggc | 534 |

<210> SEQ ID NO 74
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 74

| | | | | | |
|---|---|---|---|---|---|
| caggactcca | cctcagacct | gatcccagcc | ccacctctga | gcaaggtccc | tctgcagcag | 60 |
| aacttccagg | acaaccaatt | ccatgggaaa | tggtatgtcg | tgggctgggc | cggaaatact | 120 |
| acgctgcgtg | aggataagga | tccgcctaaa | atgcctgcga | ccatttacga | gttgaaagaa | 180 |
| gataaatcat | ataacgtcac | cgatgtgcag | tttccggata | agaaatgcgt | gtactcgatt | 240 |
| attacctttg | tgccggggag | ccagccgggc | gagtttactt | taggcgggat | taaaagtaat | 300 |
| ccgggcaata | catcacattt | ggtccgcgtc | gtgagcacca | actacaacca | gcatgccatg | 360 |
| gtgttcttca | agtatgtggt | gcagaaccgc | gaggggttta | atatcacact | gtacgggcgc | 420 |

```
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 75
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 75

```
caggactcca cctcagacct gatcccagcc ccacctctga gcaaggtccc tctgcagcag      60
aacttccagg acaaccaatt ccatgggaaa tggtatgtcg tgggccttgc cggaaatggt     120
tggctgcgtg aggataagga tccgcttaaa atgatggcga ccatttacga gttgaaagaa     180
gataaatcat ataacgtcac cgtggtggat tttgagctta agaaatgcag gtacatgatt     240
gagacctttg tgccggggag ccagccgggc gagtttactt taggcgatat taaaagttct     300
ccgggctgga catcacagtt ggtccgcgtc gtgagcacca actacaacca gcatgccatg     360
gtgttcttca agggggtgta tcagaaccgc gagtggtttc atatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

<210> SEQ ID NO 76
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 76

```
caggactcca cctcagacct gatcccagcc ccacctctga gcaaggtccc tctgcagcag      60
aacttccagg acaaccaatt ccatgggaaa tggtatgtcg tgggctgggc cggaaatacg     120
acgctgcgtg aggataagga tccgcctaaa atgcctgcgg tcatttacga gttgaaagaa     180
gataaatcat ataacgtcac cgatgtgcag tttcccgaga aggaatgcat ttactctact     240
attacctttg tgccggggag ccagccgggc gagtttactt taggcggtat taaaagtagt     300
ccgggccaga catcacattt ggtccgcgtc gtgagcacca actacaacca gcatgccatg     360
gtgttcttca agtatgtgac tcagaaccgc gaggggttta atatcacgct gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

<210> SEQ ID NO 77
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 77

```
caggactcca cctcagacct gatcccagcc ccacctctga gcaaggtccc tctgcagcag      60
aacttccagg acaaccaatt ccatgggaaa tggtatgtcg tgggccttgc cggaaatggt     120
tggctgcgtg aggatgagga tccgcttaaa atgatggcgg ccgtttacga gttgagagaa     180
```

```
gataaatcat ataacgtcac cgtggtggat tttgagcttg aggaatgcag gtacatgact      240
gagacctttg tgccggggaa ccagccgggc gagtttactt taggcgatat taaaagttct     300
ccgggctgga catcacagct ggtccgcgtc gtgagcacca actacaacca gcatgccatg     360
gtgttcttca aggggtgta tcagaaccgc gagtggtttc atatcacact gtacgggcgc      420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

<210> SEQ ID NO 78
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 78

```
caggactcca cctcagacct gatcccagcc ccacctctga gcaaggtccc tctgcagcag      60
aacttccagg acaaccaatt ccaagggaaa tggtatgtcg tgggctgggc cggagatacg     120
acgctgcgtg aggataagga tccgcctaaa atgcctgcgg tcatttacga gttgaaagaa     180
gataaatcat atgatgtcac cgatgtgcag tttcccgaga aggaatgcat ttactctact     240
attacctttg tgccggggag ccagccgggc gagtttactt taggcggtat taaaagtagt     300
ccgggccaga catcacattt ggtccgcgtc gtgagcacca actacaacca gcatgccatg     360
gtgttcttca agtatgtgac tcagaaccgc gagggggttta atatcgcgct gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

<210> SEQ ID NO 79
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 79

```
caggactcca cctcagacct gatcccagcc ccacctctga gcaaggtccc tctgcagcag      60
aacttccagg acaaccaatt ccaagggaaa tggtatgtcg tgggctgggc cggaaatacg     120
gctctgcgtg aggataagga tccgcctaaa atgcctgcgg tcatttacga gttgaaagaa     180
gataaatcat atgatgtcac cgatgtgcag tttcccgaga aggaatgcat ttactctact     240
attacctttg tgccggggag ccagccgggc gagtttactt taggcggtat taaaagtagt     300
ccgggccaga catcacattt ggtccgcgtc gtgagcacca actacaacca gcatgccatg     360
gtgttcttca agtatgtgac tcagaaccgc gagggggttta atatcgctct gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

<210> SEQ ID NO 80
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 80

```
caggactcca cctcagacct gatcccagcc ccacctctga gcaaggtccc tctgcagcag    60
aacttccagg acaaccaatt ccatgggaaa tggtatgtcg tgggccttgc cggaaatggt   120
tggctgcgtg aggatgagga tccgcttaaa atgatggcgg ccgtttacga gttgagagaa   180
gataaatcat atgacgtcac cgtggtggat tttgagcttg aggaatgcag gtacatgact   240
gagacctttg tgccggggaa ccagccgggc gagtttactt taggcgatat taaaagttct   300
ccgggctgga catcacagct ggtccgcgtc gtgagcacca actacaacca gcatgccatg   360
gtgttcttca aggggtgta tcagaaccgc gagtggtttc atatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 81
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 81

```
caggactcca cctcagacct gatcccagcc ccacctctga gcaaggtccc tctgcagcag    60
aacttccagg acaaccaatt ccatgggaaa tggtatgtcg tgggccttgc cggaaatggt   120
tggctgcgtg aggatgagga tccgcttaaa atgatggcgg ccgtttacga gttgagagaa   180
gataaatcat atcaggtcac cgtggtggat tttgagcttg aggaatgcag gtacatgact   240
gagacctttg tgccggggaa ccagccgggc gagtttactt taggcgatat taaaagttct   300
ccgggctgga catcacagct ggtccgcgtc gtgagcacca actacaacca gcatgccatg   360
gtgttcttca aggggtgta tcagaaccgc gagtggtttc atatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 82
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 82

```
caggactcca cctcagacct gatcccagcc ccacctctga gcaaggtccc tctgcagcag    60
aacttccagg acaaccaatt ccatgggaaa tggtatgtcg tgggcgttgc cggaaatgag   120
gttctgcgtg aggataagga tccgggaaaa atgcctgcga ccatttacga gttgaaagaa   180
gataaatcat ataacgtcac cgaggtgcgt tttcacaata gaaatgcaa ttacagcatt    240
gagacctttg tgccggggag ccagccgggc gagtttactt taggcaatat taaaagtaat   300
ccgggccaaa catcaatgtt ggtccgcgtc gtgagcacca actacaacca gcatgccatg   360
gtgttcttca agaaagtgaa acagaaccgc gagggatttt ggatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

```
<210> SEQ ID NO 83
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 83
caggactcca cctcagacct gatcccagcc ccacctctga gcaaggtccc tctgcagcag      60
aacttccagg acaaccaatt ccatgggaaa tggtatgtcg tgggcctggc cggaaatacc     120
atcctgcgtg aggataagga tccgggaaaa atgaatgcga ccatttacga gttgaaagaa     180
gataaatcat ataacgtcac cgacgtgcgt tttatcatga gaaatgccca ctactacatt     240
gagacctttg tgccggggag ccagccgggc gagtttactt taggcatcat taaaagtaat     300
ccgggcacca catcacaatt ggtccgcgtc gtgagcacca actacaacca gcatgccatg     360
gtgttcttca agatcgtgcg tcagaaccgc gagatgtttt ggatcacact gtacgggcgc     420
acgaaagaac tgacaagcga gctgaaggaa aattttatcc gctttccaa atctctgggc      480 ctccctgaaa accacatcgt cttccctgtc ccaatcgacc agtgtatcga cggc            534

<210> SEQ ID NO 84
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 84
caggactcca cctcagacct gatcccagcc ccacctctga gcaaggtccc tctgcagcag      60
aacttccagg acaaccaatt ccatgggaaa tggtatgtcg tgggcatcgc cggaaatacc     120
gttctgcgtg aggataagga tccgggaaaa atgcctgcga ccatttacga gttgaaagaa     180
gataaatcat ataacgtcac cgaggtgcgt tttgcaccta gaaatgcat ctacagcatt      240 agcacctttg tgccggggag ccagccgggc gagtttactt taggcatgat taaaagtagc     300
ccgggcggaa catcagcatt ggtccgcgtc gtgagcacca actacaacca gcatgccatg     360
gtgttcttca agaaagtgag ccagaaccgc gaggttttt ggatcacact gtacgggcgc      420
acgaaagaac tgacaagcga gctgaaggaa aattttatcc gctttccaa atctctgggc      480 ctccctgaaa accacatcgt cttccctgtc ccaatcgacc agtgtatcga cggc            534

<210> SEQ ID NO 85
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 85
caggactcca cctcagacct gatcccagcc ccacctctga gcaaggtccc tctgcagcag      60
aacttccagg acaaccaatt ccatgggaaa tggtatgtcg tgggcctggc cggaaataat     120
atcctgcgtg aggataagga tccggcaaaa atgcctgcga ccatttacga gttgaaagaa     180
gataaatcat ataacgtcac cgaggtgcgt tttagccaaa agaaatgcat gtacgcaatt     240
tacacctttg tgccggggag ccagccgggc gagtttactt taggccgtat taaaagtcct     300
ccgggcacca catcaatctt ggtccgcgtc gtgagcacca actacaacca gcatgccatg     360
```

```
gtgttcttca agaaagtgat gcagaaccgc gagttctttt ggatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

```
<210> SEQ ID NO 86
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 86
caggactcca cctcagacct gatcccagcc ccacctctga gcaaggtccc tctgcagcag      60
aacttccagg acaaccaatt ccatgggaaa tggtatgtcg tgggcctggc cggaaatcac     120
atcctgcgtg aggataagga tccggcaaaa atgcctgcga ccatttacga gttgaaagaa     180
gataaatcat ataacgtcac cgaggtgcgt tttggacgta agaaatgcca ctactggatt     240
gagacctttg tgccggggag ccagccgggc gagtttactt taggccgtat taaaagtgac     300
ccgggcatga catcattctt ggtccgcgtc gtgagcacca actacaacca gcatgccatg     360
gtgttcttca aggcagtgga ccagaaccgc gagaattttt ggatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

```
<210> SEQ ID NO 87
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 87
caggactcca cctcagacct gatcccagcc ccacctctga gcaaggtccc tctgcagcag      60
aacttccagg acaaccaatt ccatgggaaa tggtatgtcg tgggcaatgc cggaaatgga    120
cgtctgcgtg aggataagga tccgcctaaa atgtgggcga ccatttacga gttgaaagaa     180
gataaatcat ataacgtcac ccgtgtgtgg tttaatcaaa agaaatgcaa atacgacatt     240
gagacctttg tgccggggag ccagccgggc gagtttactt taggcgacat taaaagtacc     300
ccgggctgga catcaaattt ggtccgcgtc gtgagcacca actacaacca gcatgccatg     360
gtgttcttca agaatgtgat gcagaaccgc gagatctttt acatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

```
<210> SEQ ID NO 88
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 88
caggactcca cctcagacct gatcccagcc ccacctctga gcaaggtccc tctgcagcag      60
aacttccagg acaaccaatt ccatgggaaa tggtatgtcg tgggcgttgc cggaaatacc    120
```

```
acctgcgtg   aggataagga   tccgggaaaa   atgggagcga   ccatttacga   gttgaaagaa       180
gataaatcat   ataacgtcac   cgaggtgcgt   tttggacgta   agaaatgcgg   atactggatt      240
gagacctttg   tgccggggag   ccagccgggc   gagtttactt   taggcgcaat   taaaagttgg      300
ccgggcatca   catcaggatt   ggtccgcgtc   gtgagcacca   actacaacca   gcatgccatg      360
gtgttcttca   agaaagtgaa   tcagaaccgc   gaggtttttt   ggatcacact   gtacgggcgc      420
acgaaagaac   tgacaagcga   gctgaaggaa   aattttatcc   gcttttccaa   atctctgggc      480
ctccctgaaa   accacatcgt   cttccctgtc   ccaatcgacc   agtgtatcga   cggc            534
```

<210> SEQ ID NO 89
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 89

```
caggactcca   cctcagacct   gatcccagcc   ccacctctga   gcaaggtccc   tctgcagcag       60
aacttccagg   acaaccaatt   ccatgggaaa   tggtatgtcg   tgggcgtggc   cggaaatgag      120
gtgctgcgtg   atgataagga   tccggggaaa   atgcctgcga   ccatttacga   gttgaaagaa      180
gataaatcat   ataacgtcac   cgaggtgagg   tttcataata   agaaatgcaa   ttactcgatt      240
gagacctttg   tgccggggag   ccagccgggc   gagtttactt   taggcaagat   taaaagtaat      300
ccgggcgtga   catcaatgtt   ggtccgcgtc   gtgagcacca   actacaacca   gcatgccatg      360
gtgttcttca   agaatgtgaa   gcagaaccgc   gaggggtttt   ggatcacact   gtacgggcgc      420
acgaaagaac   tgacaagcga   gctgaaggaa   aattttatcc   gcttttccaa   atctctgggc      480
ctccctgaaa   accacatcgt   cttccctgtc   ccaatcgacc   agtgtatcga   cggc            534
```

<210> SEQ ID NO 90
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 90

```
caggactcca   cctcagacct   gatcccagcc   ccacctctga   gcaaggtccc   tctgcagcag       60
aacttccagg   acaaccaatt   ccatgggaaa   tggtatgtcg   tgggcgtggc   cggaaatact      120
gtgctgcgtg   atgataagga   tccggggaaa   atgcctgcga   ccatttacga   gttgaaagaa      180
gataaatcat   ataacgtcac   cgaggtgagg   tttcataata   agaaatgcaa   ttactctatt      240
gagacctttg   tgccggggag   ccagccgggc   gagtttactt   taggcaatat   taaaagttat      300
ccgggccaga   catcaatgtt   ggtccgcgtc   gtgagcacca   actacaacca   gcatgccatg      360
gtgttcttca   agaaggtgaa   gcagaaccgc   gaggtgtttt   ggatcacact   gtacgggcgc      420
acgaaagaac   tgacaagcga   gctgaaggaa   aattttatcc   gcttttccaa   atctctgggc      480
ctccctgaaa   accacatcgt   cttccctgtc   ccaatcgacc   agtgtatcga   cggc            534
```

<210> SEQ ID NO 91
<211> LENGTH: 534
<212> TYPE: DNA
<213> ORGANISM: Artificial Sequence
<220> FEATURE:

<223> OTHER INFORMATION: DNA encoding an expressed protein amino acid
      sequence

<400> SEQUENCE: 91

| caggactcca cctcagacct gatcccagcc ccacctctga gcaaggtccc tctgcagcag | 60  |
| aacttccagg acaaccaatt ccatgggaaa tggtatgtcg tgggcgttgc cggaaatacg | 120 |
| gtgctgcgtg acgataagga tccgggtaaa atgcctgcga ccatttacga gttgaaagaa | 180 |
| gataaatcat ataacgtcac cgaggtgcgg tttcataaga agaaatgcaa ttactttatt | 240 |
| gagacctttg tgccggggag ccagccgggc gagtttactt taggcaagat taaaagtcat | 300 |
| ccgggccaga catcaatgtt ggtccgcgtc gtgagcacca actacaacca gcatgccatg | 360 |
| gtgttcttca agaaggtgaa gcagaaccgc gaggcgtttt ggatcacact gtacgggcgc | 420 |
| acgaaagaac tgacaagcga gctgaaggaa aattttatcc gctttccaa atctctgggc | 480 |
| ctccctgaaa accacatcgt cttccctgtc ccaatcgacc agtgtatcga cggc        | 534 |

<210> SEQ ID NO 92
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 92

| caggactcca cctcagacct gatcccagcc ccacctctga gcaaggtccc tctgcagcag | 60  |
| aacttccagg acaaccaatt ccatgggaaa tggtatgtcg tgggcgttgc cggaaatcag | 120 |
| gtgctgcgtg atgataagga tccgggtaaa atgcctgcga ccatttacga gttgaaagaa | 180 |
| gataaatcat ataacgtcac cgaggtgagg tttcataata agaaatgcaa ttactggatt | 240 |
| gagacctttg tgccggggag ccagccgggc gagtttactt taggcaatat taaaagtaat | 300 |
| ccgggccata catcaatgtt ggtccgcgtc gtgagcacca actacaacca gcatgccatg | 360 |
| gtgttcttca agaaggtgaa gcagaaccgc gagggttttt ggatcacact gtacgggcgc | 420 |
| acgaaagaac tgacaagcga gctgaaggaa aattttatcc gctttccaa atctctgggc | 480 |
| ctccctgaaa accacatcgt cttccctgtc ccaatcgacc agtgtatcga cggc        | 534 |

<210> SEQ ID NO 93
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 93

| caggactcca cctcagacct gatcccagcc ccacctctga gcaaggtccc tctgcagcag | 60  |
| aacttccagg acaaccaatt ccatgggaaa tggtatgtcg tgggcgttgc cggaaatacg | 120 |
| attctgcgtg aggataagga tccggggaaa atgaatgcga ccatttacga gttgaaagaa | 180 |
| gataaatcat ataacgtcac cgatgtgagg tttatttta agaaatgcca ttactatatt   | 240 |
| gatacctttg tgccggggag ccagccgggc gagtttactt taggcaatat taaagtttat  | 300 |
| ccgggcatga catcacagtt ggtccgcgtc gtgagcacca actacaacca gcatgccatg | 360 |
| gtgttcttca agattgtgag gcagaaccgc gagattttt ggatcacact gtacgggcgc  | 420 |
| acgaaagaac tgacaagcga gctgaaggaa aattttatcc gctttccaa atctctgggc | 480 |

-continued ctccctgaaa accacatcgt cttccctgtc ccaatcgacc agtgtatcga cggc        534

<210> SEQ ID NO 94
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 94
caggactcca cctcagacct gatcccagcc ccacctctga gcaaggtccc tctgcagcag     60
aacttccagg acaaccaatt ccatgggaaa tggtatgtcg tgggcgtggc cggaaatact   120
attctgcgtg aggataagga tccggggaaa atgaatgcaa ccatttacga gttgaaagaa   180
gataaatcat ataacgtcac cgatgtgagg tttattagga agaaatgcca ttactatatt   240
gatacctttg tgccggggag ccagccgggc gagtttactt taggcaatat taaaagttat   300
ccgggcacta catcacagtt ggtccgcgtc gtgagcacca actacaacca gcatgccatg   360
gtgttcttca agattgtgag gcagaaccgc gagattttt ggatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc        534

<210> SEQ ID NO 95
<211> LENGTH: 534
<212> TYPE: DNA
<213> ORGANISM: Artificial Sequence
<220> FEATURE:
<223> OTHER INFORMATION: S0475.06L06_N65D_S79F

<400> SEQUENCE: 95
caggactcca cctcagacct gatcccagcc ccacctctga gcaaggtccc tctgcagcag     60
aacttccagg acaaccaatt ccatgggaaa tggtatgtcg tgggcgtggc cggaaatgag   120
gtgctgcgtg atgataagga tccggggaaa atgcctgcga ccatttacga gttgaaagaa   180
gataaatcat atgatgtcac cgaggtgagg tttcataata agaaatgcaa ttacttcatt   240
gagacctttg tgccggggag ccagccgggc gagtttactt taggcaagat taaaagtaat   300
ccgggcgtga catcaatgtt ggtccgcgtc gtgagcacca actacaacca gcatgccatg   360
gtgttcttca agaatgtgaa gcagaaccgc gaggggtttt ggatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc        534

<210> SEQ ID NO 96
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 96
caggactcca cctcagacct gatcccagcc ccacctctga gcaaggtccc tctgcagcag     60
aacttccagg acaaccaatt ccatgggaaa tggtatgtcg tgggcgtggc cggaaatgag   120
gtgctgcgtg atgataagga tccggggaaa atgcctgcga ccatttacga gttgaaagaa   180
gataaatcat atcaggtcac cgaggtgagg tttcataata agaaatgcaa ttacttcatt   240
gagacctttg tgccggggag ccagccgggc gagtttactt taggcaagat taaaagtaat   300

-continued

```
ccgggcgtga catcaatgtt ggtccgcgtc gtgagcacca actacaacca gcatgccatg        360
gtgttcttca agaatgtgaa gcagaaccgc gagggggtttt ggatcacact gtacgggcgc        420
acgaaagaac tgacaagcga gctgaaggaa aattttatcc gcttttccaa atctctgggc        480
ctccctgaaa accacatcgt cttccctgtc ccaatcgacc agtgtatcga cggc             534
```

<210> SEQ ID NO 97
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 97

```
caggactcca cctcagacct gatcccagcc ccacctctga gcaaggtccc tctgcagcag        60
aacttccagg acaaccaatt ccatgggaaa tggtatgtcg tgggcgtggc cggaaatact        120
attctgcgtg aggataagga tccggggaaa atgaatgcag ccatttacga gttgaaagaa        180
gataaatcat atgatgtcac cgatgtgagg tttattagga agaaatgcca ttactatatt        240
gatacctttg tgccggggag ccagccgggc gagtttactt taggcaatat taaaagttat        300
ccgggcacta catcacagtt ggtccgcgtc gtgagcacca actacaacca gcatgccatg        360
gtgttcttca agattgtgag gcagaaccgc gagatttttt ggatcacact gtacgggcgc        420
acgaaagaac tgacaagcga gctgaaggaa aattttatcc gcttttccaa atctctgggc        480
ctccctgaaa accacatcgt cttccctgtc ccaatcgacc agtgtatcga cggc             534
```

<210> SEQ ID NO 98
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 98

```
caggactcca cctcagacct gatcccagcc ccacctctga gcaaggtccc tctgcagcag        60
aacttccagg acaaccaatt ccatgggaaa tggtatgtcg tgggcgtggc cggaaatact        120
attctgcgtg aggataagga tccggggaaa atgaatgcag ccatttacga gttgaaagaa        180
gataaatcat atcaggtcac cgatgtgagg tttattagga agaaatgcca ttactatatt        240
gatacctttg tgccggggag ccagccgggc gagtttactt taggcaatat taaaagttat        300
ccgggcacta catcacagtt ggtccgcgtc gtgagcacca actacaacca gcatgccatg        360
gtgttcttca agattgtgag gcagaaccgc gagatttttt ggatcacact gtacgggcgc        420
acgaaagaac tgacaagcga gctgaaggaa aattttatcc gcttttccaa atctctgggc        480
ctccctgaaa accacatcgt cttccctgtc ccaatcgacc agtgtatcga cggc             534
```

<210> SEQ ID NO 99
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 99

```
caggactcca cctcagacct gatcccagcc ccacctctga gcaaggtccc tctgcagcag        60
```

```
aacttccagg acaaccaatt ccaagggaaa tggtatgtcg tgggcgtggc cggaaatact    120
attctgcgtg aggataagga tccggggaaa atgaatgcag ccatttacga gttgaaagaa    180
gataaatcat atgatgtcac cgatgtgagg tttattagga agaaatgcca ttactatatt    240
gatacctttg tgccggggag ccagccgggc gagtttactt taggcaatat taaaagttat    300
ccgggcacta catcacagtt ggtccgcgtc gtgagcacca actacaacca gcatgccatg    360
gtgttcttca agattgtgag gcagaaccgc gagatttttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 100
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 100

```
caggactcca cctcagacct gatcccagcc ccacctctga gcaaggtccc tctgcagcag     60
aacttccagg acaaccaatt ccatgggaaa tggtatgtcg tgggcgtggc cggaaatact    120
attctgcgtg aggataagga tccggggaaa atgaatgcaa ccatttacga gttgaaagaa    180
gataaatcat atcaggtcac cgatgtgagg tttattagga agaaatgcca ttactatatt    240
gatacctttg tgccggggag ccagccgggc gagtttactt taggcaatat taaaagttat    300
ccgggcacta catcacagtt ggtccgcgtc gtgagcacca actacaacca gcatgccatg    360
gtgttcttca agattgtgag gcagaaccgc gagatttttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 101
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 101

```
caggactcca cctcagacct gatcccagcc ccacctctga gcaaggtccc tctgcagcag     60
aacttccagg acaaccaatt ccatgggaaa tggtatgtcg tgggcttcgc cggaaattgg    120
atgctgcgtg aggataagga tccgcacaaa atgaatgcga ccatttacga gttgaaagaa    180
gataaatcat ataacgtcac cgaggtgaaa tttcaagcaa agaaatgcat ctacagcatt    240
cacacctttg tgccggggag ccagccgggc gagtttactt taggcatcat taaaagtaat    300
ccgggcggaa catcagagtt ggtccgcgtc gtgagcacca actacaacca gcatgccatg    360
gtgttcttca agtgggtgca ccagaaccgc gagttctttc aaatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 102
<211> LENGTH: 534
<212> TYPE: DNA

```
<213> ORGANISM: Artificial Sequence
<220> FEATURE:
<223> OTHER INFORMATION: DNA encoding an expressed protein amino acid
      sequence

<400> SEQUENCE: 102
caggactcca cctcagacct gatcccagcc ccacctctga gcaaggtccc tctgcagcag      60
aacttccagg acaaccaatt ccatgggaaa tggtatgtcg tgggcttcgc cggaaatcgt     120
tggctgcgtg aggataagga tccgatcaaa atgtacgcga ccatttacga gttgaaagaa     180
gataaatcat ataacgtcac ccaagtgaat ttttggctga gaaatgcgc atacagcatt      240 agcacctttg tgccggggag ccagccgggc gagtttactt taggccgtat taaaagtatc     300
ccgggcccta catcagagtt ggtccgcgtc gtgagcacca actacaacca gcatgccatg     360
gtgttcttca agaccgtgat ccagaaccgc gagttctttg agatcacact gtacgggcgc     420
acgaaagaac tgacaagcga gctgaaggaa aatttttatcc gcttttccaa atctctgggc    480
ctccctgaaa accacatcgt cttccctgtc ccaatcgacc agtgtatcga cggc           534

<210> SEQ ID NO 103
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 103
caggactcca cctcagacct gatcccagcc ccacctctga gcaaggtccc tctgcagcag      60
aacttccagg acaaccaatt ccatgggaaa tggtatgtcg tgggcttcgc cggaaatctg     120
ctgctgcgtg aggataagga tccgcgtaaa atgcgtgcga ccatttacga gttgaaagaa     180
gataaatcat ataacgtcac cgacgtgcgt tttctgtaca gaaatgcat ctacagcatt      240 gcaacctttg tgccggggag ccagccgggc gagtttactt taggcggaat taaaagtgca     300
ccgggcttca catcagagtt ggtccgcgtc gtgagcacca actacaacca gcatgccatg     360
gtgttcttca agtgggtggc acagaaccgc gagtactttg agatcacact gtacgggcgc     420
acgaaagaac tgacaagcga gctgaaggaa aatttttatcc gcttttccaa atctctgggc    480
ctccctgaaa accacatcgt cttccctgtc ccaatcgacc agtgtatcga cggc           534

<210> SEQ ID NO 104
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 104
caggactcca cctcagacct gatcccagcc ccacctctga gcaaggtccc tctgcagcag      60
aacttccagg acaaccaatt ccatgggaaa tggtatgtcg tgggcttcgc cggaaattgg     120
cgtctgcgtg aggataagga tccgcctaaa atgagcgcga ccatttacga gttgaaagaa     180
gataaatcat ataacgtcac caatgtgcgt ttttggccta gaaatgccg ttacagcatt      240 agcacctttg tgccggggag ccagccgggc gagtttactt taggcatgat taaaagtcct    300
ccgggcggaa catcagagtt ggtccgcgtc gtgagcacca actacaacca gcatgccatg    360
gtgttcttca agtgggtgtt ccagaaccgc gagttctttg agatcacact gtacgggcgc    420
```

```
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 105
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 105

```
caggactcca cctcagacct gatcccagcc ccacctctga gcaaggtccc tctgcagcag    60
aacttccagg acaaccaatt ccatgggaaa tggtatgtcg tgggcgaggc cggaaatctg    120
gcactgcgtg aggataagga tccgaaaaaa atgatggcga ccatttacga gttgaaagaa    180
gataaatcat ataacgtcac cgaggtgcgt tttcgtcaca gaaatgccaa atacgacatt    240
gcaacctttg tgccggggag ccagccgggc gagtttactt taggcctgat taaaagtgac    300
ccgggccaaa catcagagtt ggtccgcgtc gtgagcacca actacaacca gcatgccatg    360
gtgttcttca gaaagtggt tcagaaccgc gagttctttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 106
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 106

```
caggactcca cctcagacct gatcccagcc ccacctctga gcaaggtccc tctgcagcag    60
aacttccagg acaaccaatt ccatgggaaa tggtatgtcg tgggcgaggc cggaaatctt    120
gctctgcgtg aggataagga tccgatgaaa atgatggcga ccatttacga gttgaaagaa    180
gataaatcat ataacgtcac cgaggtgagg tttaggcaga agaaatgcaa gtacgatatt    240
gttacctttg tgccggggag ccagccgggc gagtttactt taggccttat taaaagtgat    300
ccgggccaga catcagagtt ggtccgcgtc gtgagcacca actacaacca gcatgccatg    360
gtgttcttca gaaggtggt tcagaaccgc gagtattttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 107
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 107

```
caggactcca cctcagacct gatcccagcc ccacctctga gcaaggtccc tctgcagcag    60
aacttccagg acaaccaatt ccatgggaaa tggtatgtcg tgggcgaggc cggaaatctt    120
actctgcgtg aggataagga tccgatgaaa atgatggcga ccatttacga gttgaaagaa    180
```

```
gataaatcat ataacgtcac cgaggtgagg tttaggcgta agaaatgcaa gtacgatatt      240
gttacctttg tgccggggag ccagccgggc gagtttactt taggcgtgat taaaagtgat      300
ccgggccaga catcagagtt ggtccgcgtc gtgagcacca actacaacca gcatgccatg      360
gtgttcttca agaaggtggt tcagaaccgc gagtattttt ggatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 108
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 108

```
caggactcca cctcagacct gatcccagcc ccacctctga gcaaggtccc tctgcagcag       60
aacttccagg acaaccaatt ccatgggaaa tggtatgtcg tgggcgaggc cggaaatctt      120
gctctgcgtg aggataagga tccgatgaaa atgatggcga ccatttacga gttgaaagaa      180
gataaatcat ataacgtcac cgaggtgagg tttaggcata agaaatgcaa gtacgatatt      240
gttacctttg tgccggggag ccagccgggc gagtttactt taggccttat taaaagtgat      300
ccgggccaga catcagagtt ggtccgcgtc gtgagcacca actacaacca gcatgccatg      360
gtgttcttca agaaggtggt tcagaaccgc gagtattttt ggatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 109
<211> LENGTH: 522
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 109

```
caggactcca cctcagacct gatcccagcc ccacctctga gcaaggtccc tctgcagcag       60
aacttccagg acaaccaatt ccatgggaaa tggtatgtcg tgggcgaggc cggaaatctt      120
gctctgcgtg aggataagga tccgaagaaa atgatggcga ccatttacga gttgaaagaa      180
gataaatcat ataacgtcac cgaggtgagg tttcggtata agaaatgcca gtacgatatt      240
gttacctttg tgccggggag ccagccgggc gagtttactt taagtgagcc gggccagaca      300
tcagagttgg tccgcgtcgt gagcaccaac tacaaccagc atgccatggt gttcttcaag      360
aaggtggtgc agaaccgcga gttttttggg atcacactgt acgggcgcac gaaagaactg      420
acaagcgagc tgaaggaaaa ttttatccgc ttttccaaat ctctgggcct ccctgaaaac      480
cacatcgtct tccctgtccc aatcgaccag tgtatcgacg gc                         522
```

<210> SEQ ID NO 110
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 110

```
caggactcca cctcagacct gatcccagcc ccacctctga gcaaggtccc tctgcagcag    60
aacttccagg acaaccaatt ccatgggaaa tggtatgtcg tgggcgaggc cggaaatctt   120
gctcggcgtg aggataagga tccgatgaaa atgatggcga ccatttacga gttgaaagaa   180
gataaatcat ataacgtcac cgaggtgagg tttaggcata agaaatgcaa gtacgatatt   240
gttacctttg tgccggggag ccagccgggc gagtttactt taggccttat taaaagtgat   300
ccgggccaga caccagagtt ggtccgcgtc gtgagcacca actacaacca gcatgccatg   360
gtgttcttca agaaggtggt ccagaaccgc gagtattttt ggatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 111
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 111

```
caggactcca cctcagacct gatcccagcc ccacctctga gcaaggtccc tctgcagcag    60
aacttccagg acaaccaatt ccatgggaaa tggtatgtcg tgggcgaggc cggaaatctt   120
gctctgcgtg aggataagaa tccgatgaaa atgatggcga ccatttacga gttgaaagaa   180
gataaatcat ataacgtcac cgaggtgagg tttaggcata agaaatgcaa gtacgatatt   240
gttaccttcg tgccggggag ccagccgggc gagtttactt taggccttat taaaagtgat   300
ccgggccaga cgccagagtt ggtccgcgtc gtgagcacca actacaacca gcatgccatg   360
gtgttcttca agaaggtggt tcagaaccgc gagtattttt ggatcacact gtacgggcgc   420
acgaaagaac tgccaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 112
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 112

```
caggactcca cctcagacct gatcccagcc ccacctctga gcaaggtccc tctgcagcag    60
aacttccagg acaaccaatt ccatgggaaa tggtatgtcg tgggcgaggc cggaaatctt   120
gctctgcgtg agggtaggga tccgatgaaa atgatggcga ccatttacga gttgaaagaa   180
gataaatcat ataacgtcac cgaggtgagg tttaggcata agaaatgcaa gtacgatatt   240
gttacctttg tgccggggag ccagccgggc gagtttactt taggccttat taaaagtgat   300
ccgggccaga caccagagtt ggtccgcgtc gtgagcacca actacaacca gcatgccatg   360
gtgttcttca agaaggtggt tcagaaccgc gagtattttt ggatcacact gtacgggcgc   420
acgaaagaac tgacaagcga gctgaaggaa aattttatcc gcttttccaa atctctgggc   480
ctccctgaaa accacatcgt cttccctgtc ccaatcgacc agtgtatcga cggc         534
```

<210> SEQ ID NO 113
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 113

```
caggactcca cctcagacct gatcccagcc ccacctctga gcaaggtccc tctgcagcag      60
aacttccagg acaaccaatt ccatgggaaa tggtatgtcg tgggcgaggc cggaaatctt     120
gctcggcgtg aggataagga tccgatgaaa atgatggcga ccatttacga gttgaaagaa     180
gataaatcat atgacgtcac cgaggtgagg tttaggcata agaaatgcaa gtacgatatt     240
gttacctttg tgccggggag ccagccgggc gagtttactt taggccttat taaaagtgat     300
ccgggccaga caccagagtt ggtccgcgtc gtgagcacca actacaacca gcatgccatg     360
gtgttcttca agaaggtggt ccagaaccgc gagtattttt ggatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc           534
```

<210> SEQ ID NO 114
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 114

```
caggactcca cctcagacct gatcccagcc ccacctctga gcaaggtccc tctgcagcag      60
aacttccagg acaaccaatt ccatgggaaa tggtatgtcg tgggcgaggc cggaaatctt     120
gctctgcgtg aggataagaa tccgatgaaa atgatggcga ccatttacga gttgaaagaa     180
gataaatcat atgacgtcac cgaggtgagg tttaggcata agaaatgcaa gtacgatatt     240
gttaccttcg tgccggggag ccagccgggc gagtttactt taggccttat taaaagtgat     300
ccgggccaga cgccagagtt ggtccgcgtc gtgagcacca actacaacca gcatgccatg     360
gtgttcttca agaaggtggt tcagaaccgc gagtattttt ggatcacact gtacgggcgc     420
acgaaagaac tgccaagcga gctgaaggaa aattttatcc gcttttccaa atctctgggc     480
ctccctgaaa accacatcgt cttccctgtc ccaatcgacc agtgtatcga cggc           534
```

<210> SEQ ID NO 115
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 115

```
caggactcca cctcagacct gatcccagcc ccacctctga gcaaggtccc tctgcagcag      60
aacttccagg acaaccaatt ccatgggaaa tggtatgtcg tgggcgaggc cggaaatctt     120
gctctgcgtg agggtaggga tccgatgaaa atgatggcga ccatttacga gttgaaagaa     180
gataaatcat atgacgtcac cgaggtgagg tttaggcata agaaatgcaa gtacgatatt     240
gttacctttg tgccggggag ccagccgggc gagtttactt taggccttat taaaagtgat     300
ccgggccaga caccagagtt ggtccgcgtc gtgagcacca actacaacca gcatgccatg     360
```

```
gtgttcttca agaaggtggt tcagaaccgc gagtattttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 116
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 116

```
caggactcca cctcagacct gatcccagcc ccacctctga gcaaggtccc tctgcagcag     60
aacttccagg acaaccaatt ccaagggaaa tggtatgtcg tgggcgaggc cggaaatctt    120
gctcggcgtg aggataagga tccgatgaaa atgatggcga ccatttacga gttgaaagaa    180
gataaatcat atgacgtcac cgaggtgagg tttaggcata agaaatgcaa gtacgatatt    240
gttacctttg tgccggggag ccagccgggc gagtttactt taggccttat taaaagtgat    300
ccgggccaga caccagagtt ggtccgcgtc gtgagcacca actacaacca gcatgccatg    360
gtgttcttca agaaggtggt ccagaaccgc gagtattttt ggatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 117
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 117

```
caggactcca cctcagacct gatcccagcc ccacctctga gcaaggtccc tctgcagcag     60
aacttccagg acaaccaatt ccatgggaaa tggtatgtcg tgggcctggc cggaaatatc    120
ctgctgcgtg aggataagga tccgcacaaa atgctggcga ccatttacga gttgaaagaa    180
gataaatcat ataacgtcac ccacgtgacc tttaaatgag agaaatgcta ctacgcaatt    240
cgtacctttg tgccggggag ccagccgggc gagtttactt taggcatgat taaaagtgag    300
ccgggccaca catcaatgtt ggtccgcgtc gtgagcacca actacaacca gcatgccatg    360
gtgttcttca agtgggtgga ccagaaccgc gaggagtttc tgatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 118
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 118

```
caggactcca cctcagacct gatcccagcc ccacctctga gcaaggtccc tctgcagcag     60
aacttccagg acaaccaatt ccatgggaaa tggtatgtcg tgggccacgc cggaaatcaa    120
```

```
tggctgcgtg aggataagga tccgcgtaaa atgtgggcga ccatttacga gttgaaagaa    180
gataaatcat ataacgtcac cgacgtggac tttgcaatca agaaatgcca ctaccgtatt    240
accacctttg tgccggggag ccagccgggc gagtttactt taggcaatat taaaagtcac    300
ccgggcggaa catcaggatt ggtccgcgtc gtgagcacca actacaacca gcatgccatg    360
gtgttcttca agttcgtgat ccagaaccgc gaggcatttt tcatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc           534
```

<210> SEQ ID NO 119
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 119

```
caggactcca cctcagacct gatcccagcc ccacctctga gcaaggtccc tctgcagcag     60
aacttccagg acaaccaatt ccatgggaaa tggtatgtcg tgggcatggc cggaaatttc    120
cacctgcgtg aggataagga tccgagcaaa atgcctgcga ccatttacga gttgaaagaa    180
gataaatcat ataacgtcac ccacgtgcct ttttgggcaa agaaatgcgc atacaaaatt    240
atcacctttg tgccggggag ccagccgggc gagtttactt taggcgcaat taaaagtgga    300
ccgggcatga catcatggtt ggtccgcgtc gtgagcacca actacaacca gcatgccatg    360
gtgttcttca agggagtgtg gcagaaccgc gagaccttg ttatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc           534
```

<210> SEQ ID NO 120
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 120

```
caggactcca cctcagacct gatcccagcc ccacctctga gcaaggtccc tctgcagcag     60
aacttccagg acaaccaatt ccatgggaaa tggtatgtcg tgggcgttgc cggaaattac    120
tggctgcgtg aggataagga tccggcaaaa atgtacgcga ccatttacga gttgaaagaa    180
gataaatcat ataacgtcac cgacgtgcgt ttttggcgta agaaatgccg ttacgacatt    240
tggacctttg tgccggggag ccagccgggc gagtttactt taggccctat taaaagtgag    300
ccgggccaaa catcacggtt ggtccgcgtc gtgagcacca actacaacca gcatgccatg    360
gtgttcttca agctggtgcg tcagaaccgc gaggcattta atatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc           534
```

<210> SEQ ID NO 121
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 121

```
caggactcca cctcagacct gatcccagcc ccacctctga gcaaggtccc tctgcagcag      60
aacttccagg acaaccaatt ccatgggaaa tggtatgtcc tgggcatggc cggaaatttc     120
cacctgcgtg aggataagga tccgagcaag atgcctgcga ccatttacga gttgaaagaa     180
gataaatcat ataacgtcac ccacgtgcct ttttgggcaa agaaatgcgc atacaaaact     240
atcacctttg tgccggggag ccagccgggc gagtttactt taggcgcaat taaaagtgga     300
ccgggcatga catcatggtt ggtccgcgtc gtgagcacca actacaacca gcatgccatg     360
gtgttctcca agggagtgtg gcagaaccgc gagacctttg ttatcacact gtacgggcgc     420
gcgaaagaac tgacaagcga gctgaaggaa aattttatcc gcttttccaa atctctgggc     480
ctccctgaaa accacatcgt cttccctgtc ccaatcgacc agtgtatcga cggc            534
```

<210> SEQ ID NO 122
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 122

```
caggactcca cctcagacct gatcccagcc ccacctctga gcaaggtccc tctgcagcag      60
aacttccagg acaaccaatt ccatgggaaa tggtatgtcg tgggcatggc cggaaatttc     120
cacctgcgtg aggataagga tccgagcaaa atgcctgcga ccatttacga gttgaaagaa     180
gataaatcat ataacgtcac ccacgtgcct ttttgggcaa agaaatgcgc atacaaaact     240
atcacctttg tgccggggag ccagccgggc gagtttactt taggcgcaat taaaagtgga     300
ccgggcatga catcatggtt ggtccgcgtc gtgagcacca actacaacca gcatgccatg     360
gtgttctcca agggagtgtg gcagaaccgt gagacctttg ttatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534
```

<210> SEQ ID NO 123
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 123

```
caggactcca cctcagacct gatcccagcc ccacctctga gcaaggtccc tctgcagcag      60
aacttccagg acaaccaatt ccatgggaaa tggtatgtcg tgggccacgc cggaaatcaa     120
tggctgcgtg agggtaggga tccgcgtaaa atgtgggcga ccatttacga gttgaaagaa     180
gataaatcat ataacgtcac cgacgtggac tttgcaatca agaaatgcct ctaccgtatt     240
accacctttg tgccagggag ccagccgggc gagtttactt taggcaatat taaaagtcac     300
ccgggcggaa catcaggatt ggtccgcgtc gtgagcacca actacaacca gcatgccatg     360
gtgttcttca agttcgtgat ccagaaccgc gaggcatttt tcatcacact gtacgggcgc     420
```

```
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 124
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 124

```
caggactcca cctcagacct gatcccagcc ccacctctga gcaaggtccc tctgcagcag    60
aacttccagg acaaccaatt ccatgggaaa tggtatgtcg tgggccacgc cggaaatcaa    120
tggctgcgtg gggattacga tccgcgtaaa atgtgggcga ccatttacga gttgaaagaa    180
gataaatcat ataacgtcac cgacgtggac tttgcaatcg agaaatgcca ctaccgtatt    240
accacctttg tgccggggag ccagccgggc gagtttactt ttggcaatat aaaaagtcac    300
ccgggcggaa catcaggatt ggcccgcgtc gtgagcacca actacaacca gcatgccatg    360
gtgttcttca agttcgtgat ccagaaccgc gaggcatttt tcatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 125
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 125

```
caggactcca cctcagacct gatcccagcc ccacctctga gcaaggtccc tctgcagcag    60
aacttccagg acaaccaatt ccaagggaaa tggtatgtcg tgggccacgc cggaaatcaa    120
tggctgcgtg agggtaggga tccgcgtaaa atgtgggcga ccatttacga gttgaaagaa    180
gataaatcat atgacgtcac cgacgtggac tttgcaatca agaaatgcct ctaccgtatt    240
accacctttg tgccagggag ccagccgggc gagtttactt taggcaatat taaaagtcac    300
ccgggcggaa catcaggatt ggtccgcgtc gtgagcacca actacaacca gcatgccatg    360
gtgttcttca agttcgtgat ccagaaccgc gaggcatttt tcatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534
```

<210> SEQ ID NO 126
<211> LENGTH: 534
<212> TYPE: DNA
<213> ORGANISM: Artificial Sequence
<220> FEATURE:
<223> OTHER INFORMATION: DNA encoding an expressed protein amino acid
      sequence

<400> SEQUENCE: 126

```
caggactcca cctcagacct gatcccagcc ccacctctga gcaaggtccc tctgcagcag    60
aacttccagg acaaccaatt ccatgggaaa tggtatgtcg tgggccacgc cggaaatcaa    120
tggctgcgtg gggattacga tccgcgtaaa atgtgggcga ccatttacga gttgaaagaa    180
```

-continued

```
gataaatcat atgacgtcac cgacgtggac tttgcaatcg agaaatgcca ctaccgtatt      240
accacctttg tgccggggag ccagccgggc gagtttactt ttggcaatat aaaaagtcac      300
ccgggcggaa catcaggatt ggcccgcgtc gtgagcacca actacaacca gcatgccatg      360
gtgttcttca agttcgtgat ccagaaccgc gaggcatttt tcatcacact gtacgggcgc      420
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 127
<211> LENGTH: 10
<212> TYPE: PRT
<213> ORGANISM: Artificial Sequence
<220> FEATURE:
<223> OTHER INFORMATION: C-terminal sequence of muteins

<400> SEQUENCE: 127

Ser Ala Trp Ser His Pro Gln Phe Glu Lys
1               5                   10

<210> SEQ ID NO 128
<211> LENGTH: 8
<212> TYPE: PRT
<213> ORGANISM: Artificial Sequence
<220> FEATURE:
<223> OTHER INFORMATION: SA linker and the Strep Tag II

<400> SEQUENCE: 128

Trp Ser His Pro Gln Phe Glu Lys
1               5

<210> SEQ ID NO 129
<211> LENGTH: 200
<212> TYPE: PRT
<213> ORGANISM: Artificial Sequence
<220> FEATURE:
<223> OTHER INFORMATION: Expressed protein amino acid sequence

<400> SEQUENCE: 129

Met Lys His His His His His His Asp Tyr Asp Ile Pro Thr Thr Glu
1               5                   10                  15

Asn Leu Tyr Phe Gln Gly Gln Asp Ser Thr Ser Asp Leu Ile Pro Ala
                20                  25                  30

Pro Pro Leu Ser Lys Val Pro Leu Gln Gln Asn Phe Gln Asp Asn Gln
            35                  40                  45

Phe His Gly Lys Trp Tyr Val Val Gly Val Ala Gly Asn Thr Ile Leu
        50                  55                  60

Arg Glu Asp Lys Asp Pro Gly Lys Met Asn Ala Thr Ile Tyr Glu Leu
65                  70                  75                  80

Lys Glu Asp Lys Ser Tyr Asn Val Thr Asp Val Arg Phe Ile Arg Lys
                85                  90                  95

Lys Cys His Tyr Tyr Ile Asp Thr Phe Val Pro Gly Ser Gln Pro Gly
            100                 105                 110

Glu Phe Thr Leu Gly Asn Ile Lys Ser Tyr Pro Gly Thr Thr Ser Gln
        115                 120                 125

Leu Val Arg Val Val Ser Thr Asn Tyr Asn Gln His Ala Met Val Phe
    130                 135                 140

Phe Lys Ile Val Arg Gln Asn Arg Glu Ile Phe Trp Ile Thr Leu Tyr
145                 150                 155                 160

```
Gly Arg Thr Lys Glu Leu Thr Ser Glu Leu Lys Glu Asn Phe Ile Arg
                165                 170                 175

Phe Ser Lys Ser Leu Gly Leu Pro Glu Asn His Ile Val Phe Pro Val
            180                 185                 190

Pro Ile Asp Gln Cys Ile Asp Gly
        195                 200

<210> SEQ ID NO 130
<211> LENGTH: 4
<212> TYPE: PRT
<213> ORGANISM: Artificial Sequence
<220> FEATURE:
<223> OTHER INFORMATION: positions 95-98 of the WT NGAL

<400> SEQUENCE: 130

Gly Asn Ile Lys
1

<210> SEQ ID NO 131
<211> LENGTH: 6
<212> TYPE: PRT
<213> ORGANISM: Artificial Sequence
<220> FEATURE:
<223> OTHER INFORMATION: examples of albumin binding peptides
<220> FEATURE:
<221> NAME/KEY: MISC_FEATURE
<222> LOCATION: (2)..(2)
<223> OTHER INFORMATION: Xaa can be any of Asp, Asn, Ser, Thr, or Trp
<220> FEATURE:
<221> NAME/KEY: MISC_FEATURE
<222> LOCATION: (3)..(3)
<223> OTHER INFORMATION: Xaa can be any of Asn, Gln, His, Ile, Leu, or
      Lys
<220> FEATURE:
<221> NAME/KEY: MISC_FEATURE
<222> LOCATION: (4)..(4)
<223> OTHER INFORMATION: Xaa can be any of Ala, Asp, Phe, Trp, or Tyr
<220> FEATURE:
<221> NAME/KEY: MISC_FEATURE
<222> LOCATION: (5)..(5)
<223> OTHER INFORMATION: Xaa can be any of Asp, Gly, Leu, Phe, Ser, or
      Thr

<400> SEQUENCE: 131

Cys Xaa Xaa Xaa Xaa Cys
1               5

<210> SEQ ID NO 132
<211> LENGTH: 7
<212> TYPE: PRT
<213> ORGANISM: Artificial Sequence
<220> FEATURE:
<223> OTHER INFORMATION: Linker

<400> SEQUENCE: 132

Asp Tyr Asp Ile Pro Thr Thr
1               5

<210> SEQ ID NO 133
<211> LENGTH: 7
<212> TYPE: PRT
<213> ORGANISM: Artificial Sequence
<220> FEATURE:
<223> OTHER INFORMATION: protease cleavage site

<400> SEQUENCE: 133

Glu Asn Leu Tyr Phe Gln Gly
1               5
```